United States Patent
Piazza

(10) Patent No.: US 10,039,764 B2
(45) Date of Patent: Aug. 7, 2018

(54) TREATMENT AND DIAGNOSIS OF CANCER AND PRECANCEROUS CONDITIONS USING PDE10A INHIBITORS AND METHODS TO MEASURE PDE10A EXPRESSION

(71) Applicant: University of South Alabama, Mobile, AL (US)

(72) Inventor: Gary A. Piazza, Daphne, AL (US)

(73) Assignee: University of South Alabama, Mobile, AL (US)

( * ) Notice: Subject to any disclaimer, the term of this patent is extended or adjusted under 35 U.S.C. 154(b) by 106 days.

(21) Appl. No.: 14/904,632

(22) PCT Filed: Jul. 11, 2014

(86) PCT No.: PCT/US2014/046351
§ 371 (c)(1),
(2) Date: Jan. 12, 2016

(87) PCT Pub. No.: WO2015/006689
PCT Pub. Date: Jan. 15, 2015

(65) Prior Publication Data
US 2016/0143912 A1  May 26, 2016

Related U.S. Application Data

(60) Provisional application No. 61/845,787, filed on Jul. 12, 2013.

(51) Int. Cl.
| | |
|---|---|
| A61K 31/415 | (2006.01) |
| A61K 31/4155 | (2006.01) |
| A61K 31/4709 | (2006.01) |
| A61K 31/4745 | (2006.01) |
| A61K 31/4409 | (2006.01) |
| A61K 31/519 | (2006.01) |
| A61K 31/472 | (2006.01) |
| A61K 31/517 | (2006.01) |
| A61K 45/06 | (2006.01) |
| C12Q 1/6886 | (2018.01) |
| G01N 33/574 | (2006.01) |

(52) U.S. Cl.
CPC .......... *A61K 31/519* (2013.01); *A61K 31/415* (2013.01); *A61K 31/4155* (2013.01); *A61K 31/4409* (2013.01); *A61K 31/472* (2013.01); *A61K 31/4709* (2013.01); *A61K 31/4745* (2013.01); *A61K 31/517* (2013.01); *A61K 45/06* (2013.01); *C12Q 1/6886* (2013.01); *G01N 33/57496* (2013.01); *C12Q 2600/118* (2013.01); *C12Q 2600/158* (2013.01); *G01N 2333/916* (2013.01); *G01N 2800/50* (2013.01)

(58) Field of Classification Search
CPC .............. A61K 31/415; A61K 31/4709; A61K 31/4745; A61K 31/4155; A61K 31/4409
See application file for complete search history.

(56) References Cited

U.S. PATENT DOCUMENTS

| | | |
|---|---|---|
| 5,401,774 A | 3/1995 | Pamukcu et al. |
| 5,965,619 A | 10/1999 | Pamukcu et al. |
| 5,998,477 A | 12/1999 | Sperl et al. |
| 6,063,818 A | 5/2000 | Sperl et al. |
| 6,538,029 B1 | 3/2003 | Thompson et al. |
| 6,930,114 B2 | 8/2005 | Niewohner et al. |
| 6,936,609 B2 | 8/2005 | Ergueden et al. |
| 7,429,665 B2 * | 9/2008 | Verhoest ............ C07D 413/14 546/152 |
| 7,550,465 B2 | 6/2009 | Hoefgen et al. |
| 7,576,080 B2 | 8/2009 | Liu et al. |
| 7,786,139 B2 | 8/2010 | Bergmann et al. |
| 7,825,254 B2 | 11/2010 | Verhoest et al. |
| 7,846,942 B2 | 12/2010 | Nagasawa et al. |
| 7,875,618 B2 | 1/2011 | Malamas et al. |
| 8,017,604 B2 | 9/2011 | Alberati et al. |
| 8,053,438 B2 | 11/2011 | Allen et al. |
| 8,071,595 B2 | 12/2011 | Ripka et al. |
| 8,133,897 B2 | 3/2012 | Ritzen et al. |
| 8,178,538 B2 | 5/2012 | Alberati et al. |
| 8,247,418 B2 | 8/2012 | Allen et al. |
| 8,263,584 B2 | 9/2012 | Allen et al. |
| 8,263,648 B2 | 9/2012 | Balasubramanian et al. |
| 8,278,327 B2 | 10/2012 | Bergmann |
| 8,283,471 B2 | 10/2012 | Proulx-Lafrance et al. |
| 8,318,718 B2 | 11/2012 | Allen et al. |
| 8,329,700 B2 | 12/2012 | Allen et al. |
| 8,338,420 B1 | 12/2012 | Kotera et al. |

(Continued)

FOREIGN PATENT DOCUMENTS

| | | |
|---|---|---|
| EP | 1250923 A2 | 10/2002 |
| WO | 200124781 A2 | 4/2001 |

(Continued)

OTHER PUBLICATIONS

Alberts et al. "Do NSAIDs Exert Their Colon Cancer Chemoprevention Activities Through the Inhibition of Mucosal Prostaglandin Synthetase?" J. Cell. Biochem. Supp. 22(1995):18-23.

Chappie et al. "Discovery of a Series of 6,7-dimethoxy-4-pyrrolidylquinazoline PDE10A Inhibitors." J. Med. Chem. 50.2 '(2007):182-185.

Coskran et al. "Immunohistochemical Localization of Phosphodiesterase 10A in Multiple Mammalian Species." J. Histochem. Cytochem. 54.11(2006):1205-1213.

Cutshall et al. "Novel 2-methoxyacylhydrazones as Potent, Selective PDE10A Inhibitors with Activity in Animal Models of Schizophrenia." Bioorg. Med. Chem. Lett. 22.17(2012):5595-5599.

Giardiello et al. "Treatment of Colonic and Rectal Adenomas with Sulindac in Familiar Adenomatous Polyposis." New England J. Med. 328.18(1993):1313-1316.

(Continued)

*Primary Examiner* — Kara R McMillian

(74) *Attorney, Agent, or Firm* — Burns & Levinson, LLP; Shawn P. Foley

(57) ABSTRACT

Disclosed are methods for treating cancer and precancerous conditions with PDE10A specific inhibitors and diagnosis of neoplastic diseases based on elevated levels of PDE10A.

8 Claims, 15 Drawing Sheets

(56) References Cited

U.S. PATENT DOCUMENTS

| | | |
|---|---|---|
| 8,343,970 B2 | 1/2013 | Cutshall et al. |
| 8,343,973 B2 | 1/2013 | Ripka et al. |
| 8,349,824 B2 | 1/2013 | Flohr et al. |
| 8,349,830 B2 | 1/2013 | Breslin et al. |
| 8,377,930 B2 | 2/2013 | Cutshall et al. |
| 8,404,710 B2 | 3/2013 | Nagasawa |
| 8,410,117 B2 | 4/2013 | Sanchez et al. |
| 8,435,995 B2 | 5/2013 | Taniguchi et al. |
| 2006/0001975 A1 | 1/2006 | Miyata |
| 2006/0110783 A1 | 5/2006 | Golz |
| 2006/0166992 A1 | 7/2006 | Hendrix et al. |

FOREIGN PATENT DOCUMENTS

| | | |
|---|---|---|
| WO | 2008006372 A1 | 1/2008 |
| WO | 2010062559 A1 | 6/2010 |
| WO | 2010138430 A1 | 12/2010 |
| WO | 2011008597 A1 | 1/2011 |
| WO | 2011022213 A1 | 2/2011 |
| WO | 2012007006 A1 | 1/2012 |
| WO | 2013034758 A1 | 3/2013 |

OTHER PUBLICATIONS

Goluboff et al. "Exisulind (Sulindac Sulfone) Suppresses Growth of Human Prostate Cancer in a Nude Mouse Xenograft Model by Increasing Apoptosis." Urol. 53.2(1999):440-445.

Hagihara et al. "Identification of 27 5' CpG Islands Abberantly Methylated and 13 Genes Silences in Human Pancreatic Cancers." Oncogene. 23(2004):8705-8710.

Ho et al. "The SAR Development of Dihydroimidazoisoquinoline Derivatives as Phosphodiesterase 10A Inhibitors for the Treatment of Schizophrenia." Bioorg. Med. Chem. Lett. 22.7(2012):2585-2589.

Jemal et al. "Cancer Statistics, 2003." CA Cancer J. Clin. 53(2003):5-26.

Kahler et al. "Associated Study of PDE3B Gene Variants in Scandinavian Schizophrenia and Bipolar Disorder Multicenter Case-Control Samples." Am. J. Med. Genet. B Neuropsychiatr. Genet. 153B.1(2010):86-96.

Kehrer et al. "Triazoloquinazolines as a Novel Class of Phosphodiesterase 10A (PDE10A) Inhibitors." Bioorg. Med. Chem. Lett. 21.12(2011):378-3742.

Kotera et al. "Subcellular Localization of Cyclic Nucleotide Phosphodiesterase Type 10A Variants, and Alteration of the Localization of cAMP-dependent Protein Kinase-Dependent Phosphorylation." J. Biol. Chem. 279.6(2004):4366-4375.

Kwon et al. "Expression of Cyclic Guanosine Monophosphate-Dependent Protein Kinase in Metastaic Colon Carcinoma Cells Blocks Tumor Tumor Angiogenesis." Cancer. 112.7(2008):1462-1470.

Lundholm et al. "Anti-inflammatory Treatment May Prolong Survival in Undernourished Patients with Metastatic Solid Tumors." Cancer Res. 54(1994):5602-5606.

Malkinson et al. "Inhibition of 4-(methylnitrosamino)-1-(3-pyridyl)-1-butanone-induced Mouse Lung Tumor Formation by FGN-1 (Sulindac Sulfone)." Carcinogenesis. 19.8(1998):1353-1356.

Menniti et al. "Phosphodiesterases in the CNS: Targets for Drug Development." Nat. Rev. Drug Discov. 5.8 (2006):660-670.

Mukherjee. "Selective Cyclooxygenase-s (COX-2) Inhibitors and Potential Risk of Cardiovascular Events." Biochem. Jharmacol. 63(2002):817-821.

Piazza et al. "Exisulind, a Novel Proapoptotic Drug, Inhibits Rat Urinary Bladder Tumorigenesis." Cancer Res. 61 (2001):3961-3968.

Piazza et al. "Sulindac Suflone Inhibits Azoxymethand-induced Colon Carcinogenesis in Rats without Reducting Prostaglandin Levels." Cancer Res. 57(1997):2909-2915.

Raheem et al. "Discovery of Tetrahydropyridopyrimidine Phosphodiesterase 10A Inhibitors for the Treatment of Schizophrenia." Bioorg. Med. Chem. Lett. 22.18(2012):5903-5908.

Saha et al. "Downregulation of Human Colon Carcinoma Cell (COLO-205) Proliferation Through PKG-MAP Kinase Mediated Signaling Cascase by E. coli Heat Stable Enterotoxin (STa), a Potent Anti-angiogenic and Anti-metastatic Molecule." J. Appl. Tech. 28(2008):475-483.

Seeger et al. "Immunohistochemical Localization of PDE10A in the Rat Brain." Brain Res. 985.2(2003):113-126.

Smalley et al. "Use of Nonsteroidal Anti-inflammatory Drugs and Incidence of Colorectal Cancer." Arch. Intern. Med. 159(1999):161-166.

Soh et al. "Celecoxib-Induced Growth Inhibittion in SW480 Colon Cancer Cells is Associated with Activation of Protein Kinase G." Mol. Carcinogenesis. 47(2008):519-525.

Soh et al. "Cyclic GMP Mediates Apoptosis Induced by Sulindac Derivatives via Activation of c-Jun NH2 Terminal Kinase 1." Clin. Cancer Res. 6(2000):4136-4141.

Soh et al. "Role of COX-Independent Targets of NSAIDs and Related Compounds of Cancer Prevention and Treatment." Prog. Exp. Turn. Res. 37(2003):261-283.

Steinbach et al. "The Effect of Celecoxib, a Cyclooxygenase-2 Inhibitor, in Familial Adenomatous Polyposis." New Engl. J. Med. 342.26(2000):1946-1952.

Thompson et al. "Exisulind Induction of Apoptosis Involves Guanosine 3',5'-Cyclic Monophosphate Phosphodiesterase Inhibition, Protein Kinase G Activation, and Attenuated β-Catenin." Cancer Res. 60(2000):3338-3342.

Thompson et al. "Sulfone Metabolite of Sulindac Inhibits Mammary Carcinogenesis." Cancer Res. 57(1997):267-271.

Tinsley et al. "Colon Tumor Cell Growth-Inhibitory Activity of Sulindac Sulfide and Other Nonsteroidal Anti-Inflammatory Drugs is Associated with Phosphodiesterase 5 Inhibition." Cancer Prev. Res. (Phila). 3.10 (2010)1303-1313.

Tinsley et al. "Inhibition of PDE5 by Sulindac Sulfide Selectively Induces Apoptosis and Attenuates Oncogenic Wnt/β-catenin-mediated Transcription in Human Breast Tumor Cells." Cancer Prev. Res. (Phila). 4.8(2011):1275-1284.

Tinsley et al. "Sulindac Sulfide Selectively Inhibits Growth and Induces Apoptosis of Human Breast Tumor Cells by Phosphodiesterase 5 Inhibition, Elevation of Cyclic GMP, and Activation of Protein Kinase G." Mol. Cancer Ther. 8.12 (2009):3331-3340.

Whitt et al. "A Novel Sulindac Derivative that Potently Suppresses Colon Tumor Cell Growth by Inhibiting cGMP Phosphodiesterase and β-catenin Transcriptional Activity." Cancer Prey. Res. (Phila). 5.6(2012):822-833.

Xie et al. "Cellular and Subcellular Localization of PDE10A, a Striatum-Enriched Phosphodiesterase." Neurosci. 139.2 (2006):597-607.

Zhu et al. "The Novel Functions of cGMP-Specific Phosphodiesterase 5 and its Inhibitors in Carcinoma Cells and Pulmonary/Cardiovascular Vessels." Current Topics Med. Chem. 7(2007):437-454.

* cited by examiner

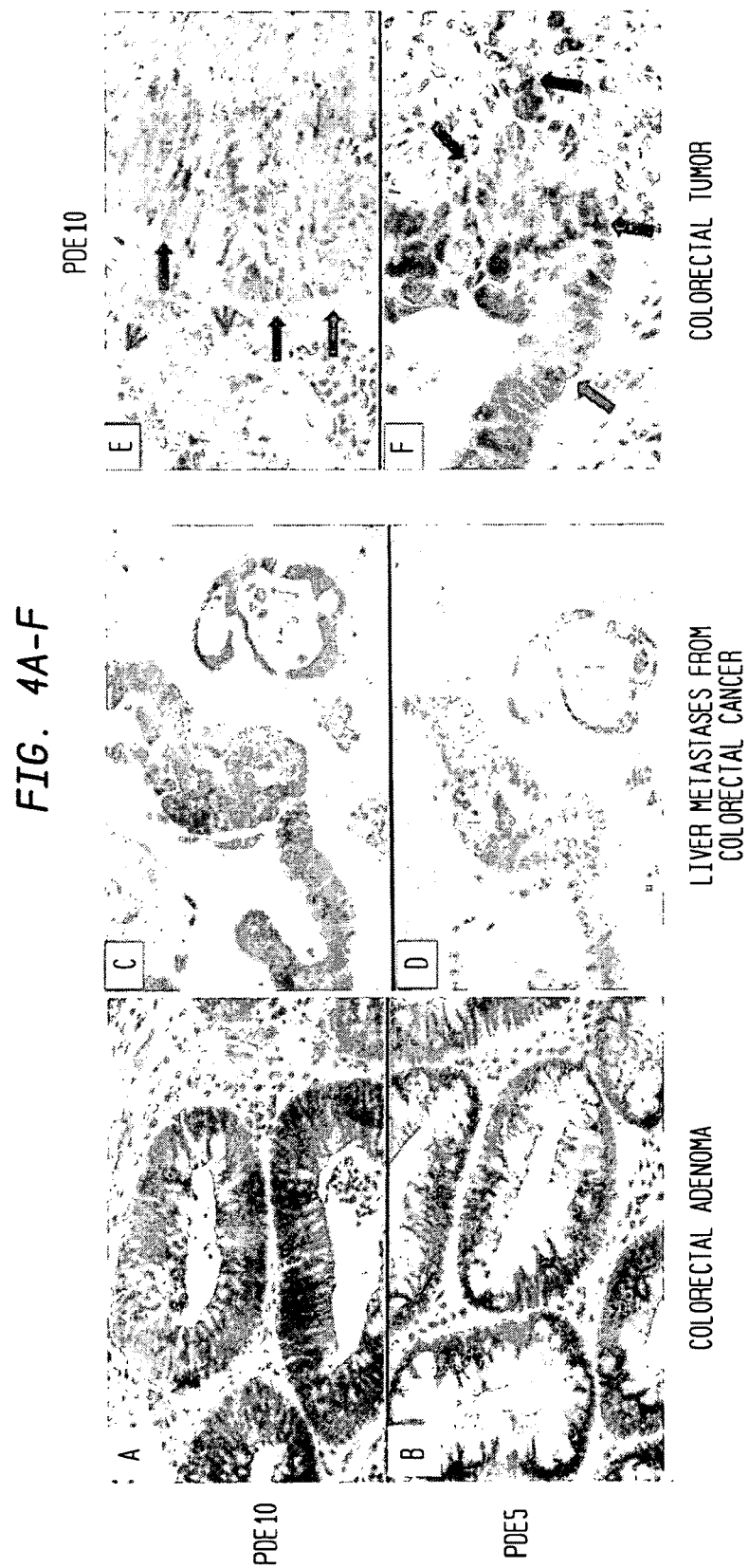
FIG. 4A-F

HCT116 CELLS

N = NORMAL; T = TUMOR; ER = ESTROGEN RECEPTOR

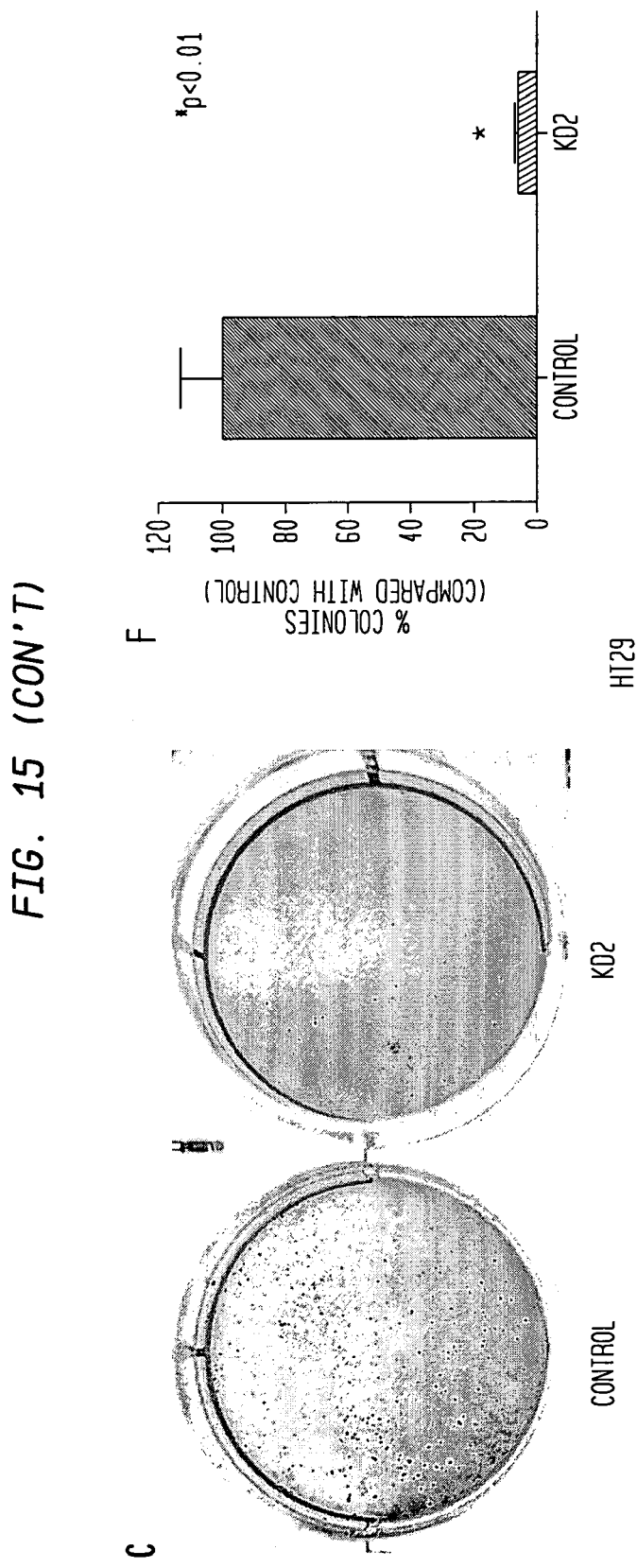
FIG. 15 (CON'T)

TREATMENT AND DIAGNOSIS OF CANCER AND PRECANCEROUS CONDITIONS USING PDE10A INHIBITORS AND METHODS TO MEASURE PDE10A EXPRESSION

CROSS REFERENCE TO RELATED APPLICATION

The present application is a national phase entry under 35 U.S.C. § 371 of International Application No. PCT/US2014/046351 filed Jul. 11, 2014, published in English, which claims priority from U.S. Provisional Application No. 61/845,787, filed Jul. 12, 2013, all of which are incorporated herein by reference.

STATEMENT REGARDING FEDERALLY SPONSORED RESEARCH OR DEVELOPMENT

The invention was made with support under NCI Grant Nos. CA 155638 and 1R01CA148817. Therefore, the Government has certain rights in the invention.

BACKGROUND OF THE INVENTION

Cancer is one of the leading causes of death in the developed world, with over one million people diagnosed with cancer and 500,000 deaths per year in the United States alone. Overall it is estimated that more than one in three people will develop some form of cancer during their lifetime. There are more than 200 different types of cancer, four of which—breast, lung, colorectal (CRC) and prostate—account for over half of all new cases (Jemal et al., Cancer J. Clin. 53:5-26 (2003)). CRC is the most common diagnosed cancer in the United States (Jemal et al., CA Cancer J. Clin. 60(5):277-300 (2010)). Chemoprevention using pharmaceutical agents to treat precancerous conditions is widely believed to be a promising strategy to reduce the incidence of and mortality from CRC and other cancer types, especially in individuals at high risk who develop large numbers of precancerous lesions that cannot be effectively removed by colonoscopy or who develop such lesions sporadically that go undetected and become cancerous. Examples of such high risk individuals include those with familial or sporadic adenomatous polyposis, hereditary non-polyposis colon cancer, and inflammatory bowel diseases, including Chrohn's disease and ulcerative colitis. While numerous mutated genes have been shown to be involved in the development of CRC, few molecular targets have been identified that are critically involved in disease initiation and progression and which are suitable drug targets. As such, few drugs have been developed and approved by the FDA to be safe and effective for cancer chemoprevention. The cyclooxygenase-2 selective inhibitor, celecoxib (Celebrex®) is one example that was approved for the treatment of familial adenomatous polyposis, but was recently withdrawn from the market. As such, there is a significant unmet medical need for new drugs to treat or prevent precancerous and cancerous conditions.

Epidemiological studies have shown that non-steroidal anti-inflammatory drugs (NSAIDs) including cyclooxygenase-2 inhibitors (Coxibs) display promising CRC chemopreventive efficacy (Smalley et al., Arch. Intern. Med. 159(2):161-6 (1999) (this is redundant with the 1$^{st}$ and last sentence in this paragraph) and other cancer types. Clinical studies have reported that certain prescription strength NSAIDs such as sulindac (Clinoril®) also have pronounced benefits for individuals with familial adenomatous polyposis (FAP) by causing the regression of precancerous adenomas, reducing both the number and size of such lesions (Giardiello et al., N. Engl. J. Med. 328(18):1313-6 (1993)). COX-2 selective inhibitors (e.g., celecoxib, Celebrex®) have similar benefits, but tend to be less effective and require higher dosages compared with sulindac(Steinbach et al., N. Engl. J. Med. 342(26):1946-52 (2000)). NSAIDs may also be effective for treating advanced stage malignant disease. For example, a clinical trial involving patients with metastatic disease reported that indomethacin (a sulindac analog) extended survival by approximately 9 months (Lundholm et al., Cancer Res. 54(21):5602-6 (1994)). Despite these promising observations, NSAIDs and COX-2 inhibitors are not recommended for cancer chemoprevention because of potentially fatal gastrointestinal, renal and cardiovascular toxicity that result from COX-1 or COX-2 inhibition and suppression of physiologically important prostaglandins (Mukherjee, Biochem. Pharmacol. 63(5):817-21 (2002)).

Still, in view of the strong cancer chemopreventive activity of NSAIDs, increasing efforts have been made to understand the underlying mechanism of action to develop improved drugs that are safer and more efficacious. While the molecular basis for the antineoplastic activity of NSAIDs is commonly attributed to COX-2 inhibition, multiple investigators have concluded that mechanisms other than COX inhibition may be involved (Alberts et al., J. Cell Biochem. Suppl. 22:18-23 (1995); Soh et al., Prog. Exp. Tumor. Res. 37:261-85 (2003); Williams et al., Cancer Res. 60:6045-6051 (2000)). For example, the sulfone metabolite of sulindac has been shown to inhibit tumorigenesis in various rodent models of CRC and other cancer types, despite its inability to inhibit COX (Goluboff et al., Urology 53(2):440-5 (1999); Malkinson et al., Carcinogenesis 19(8):1353-6 (1998); Piazza et al., Cancer Res. 57(14):2909-15 (1997); Thompson et al., Cancer Res. 57(2):267-71 (1997)). Knowledge of the underlying mechanism could lead to the identification of new molecular targets that will provide insight to the discovery of new drugs for cancer intervention and treatment. Studies have shown that the mechanism responsible for the antineoplastic activity of sulindac sulfone (exisulind) involves cyclic guanosine monophosphate phosphodiesterase (cGMP PDE) inhibition (Piazza et al., Cancer Res. 61(10):3961-8 (2001); Thompson et al., Cancer Res. 60(13):3338-42 (2000). More recently, it has been reported that the COX inhibitory sulfide metabolite of sulindac (SS) and other NSAIDs also inhibit cGMP PDE, and this activity is closely associated with their tumor cell growth inhibitory activity (Tinsley et al., Mol. Cancer Ther. 8(12):3331-40 (2009); Tinsley et al., Cancer Prey. Res. (Phila) 3(10):1303-13 (2010); Whitt et al., Cancer Prey. Res. (Phila) 5(6):822-33 (2012); Zhu et al., Curr. Top. Med. Chem. 7(4):437-54 (2007); Tinsley et al., Cancer Prey. Res. (Phila) 4(8):1275-84 (2011)). Other investigators have also suggested a relationship between cGMP elevation and CRC chemoprevention based on several independent lines of evidence (Soh et al., Mol. Carcinog. 47(7):519-25 (2008); Saha et al., J. Appl. Toxicol. 28(4):475-83 (2008); Soh et al., Clin. Cancer Res. 6(10):4136-41 (2000); Kwon et al., Cancer 112(7):1462-70 (2008)).

Phosphodiesterases (PDEs) are a class of intracellular enzymes involved in signal transduction by catalyzing the hydrolysis of the cylic nucleotides, cyclic adenosine monophosphate (cAMP) and cyclic guanosine monophosphates (cGMP) into their respective, inactive nucleotide monophosphates. The cyclic nucleotides cAMP and cGMP are synthesized by adenylyl and guanylyl cyclases, respectively, and serve as secondary messengers in multiple biochemical pathways that include the activation of cAMP and cGMP-dependent kinases and subsequent phosphorylation of specific proteins that regulate cellular activity and function. For example, cyclic nucleotides in neurons are involved in the acute regulation of synaptic transmission as well as in neuronal differentiation and survival. The complexity of cyclic nucleotide signaling is reflected by the molecular diversity of the enzymes involved in the synthesis and degradation of cAMP and cGMP. There are at least ten families of adenylyl cyclases, two families of guanylyl cyclases, and eleven families of phosphodiesterases. Furthermore, different types of neurons are known to express multiple isozymes of each of these classes, and there is evidence for compartmentalization and specificity of function for different isozymes within a given cell type.

On the basis of substrate specificity, the PDE families can be further classified into three groups: i) the cAMP-PDEs (PDE4, PDE7, PDE8), ii) the cGMP-PDEs (PDE5, PDE6 and PDE9), and iii) the dual-substrate PDEs (PDE1, PDE2, PDE3, PDE10 and PDE11). Furthermore, PDEs are differentially expressed throughout the organism and are generally believed to have distinct physiological functions. As a result of these distinct enzymatic activities and complex tissue localization patterns, different PDE isozyme families can serve as specific targets for distinct therapeutic indications. Furthermore, compounds that can selectively inhibit distinct PDE families or isozymes may offer particular tissue specificity, greater efficacy, and fewer side effects.

Although sulindac can inhibit multiple cGMP degrading isozymes, previous studies have reported that inhibition of the cGMP-specific PDE5 isozyme is closely associated with its anticancer activity (Tinsley et al., Mol. Cancer Ther. 8(12):3331-40 (2009); Tinsley et al., Cancer Prev. Res. (Phila) 3(10):1303-13 (2010); Whitt et al., Cancer Prev. Res. (Phila) 5(6):822-33 (2012); Tinsley et al., Cancer Prev. Res. (Phila) 4(8):1275-84 (2011)). However, highly potent PDE5 selective inhibitors like sildenafil inhibit tumor cell growth with low potency at concentrations that significantly exceed the concentration required for PDE5 inhibition. As such, there is the possibility that additional PDE isozymes may be involved.

PDE10, also known in the art as PDE10A, PDE10A1, or PDE10A2, is identified as a unique PDE isozyme family based on primary amino acid sequence and distinct enzymatic activity. The PDE10 family of polypeptides shows a lower degree of sequence homology as compared to previously identified PDE families and has been reported to be insensitive to certain inhibitors that are known to be specific for other PDE families. PDE10 was first discovered in 1999 (Loughney et al., Gene 234(1):109-17 (1999); Fujishige et al., Eur. J. Biochem. 266(3):1118-27 (1999); Fujishige et al., J. Biol. Chem. 274(26):18438-45 (1999); Soderling et al., Proc. Natl. Acad. Sci. USA 96(12):7071-6 (1999)). Scientific literature has reported that PDE10 is highly expressed in brain striatum, testes, and thyroid but is not or has low expression in most other peripheral tissues. See, Seeger et al., Brain Res. 985(2):113-26 (2003); Kotera et al., J. Biol. Chem. 279(6):4366-75 (2004); Xie et al., Neuroscience 139(2):597-607 (2006); Coskran et al., J. Histochem. Cytochem. 54(11):1205-13 (2006). The high expression of PDE10 in the striatum has suggested a role of this isozyme in various neurological diseases including Parkinson's disease, Huntington's disease, and schizophrenia.

BRIEF SUMMARY OF THE INVENTION

A first aspect of the present invention is directed to a method of treating cancer or a precancerous condition which entails administering to a subject in need thereof, a therapeutically effective amount of a PDE10A inhibitor. In some embodiments, the cancer is colorectal cancer. In some embodiments, the precancerous condition involves presence of pre-cancerous adenomas or polyps.

A second aspect of the present invention is directed to a method of measuring PDE10A expression (PDE10A or PDE10A mRNA) as a tool for the diagnosis or prognosis of precancerous condition or cancer. This is especially useful for analyzing tissue biopsies from individuals who are disease-free and do not show abnormal histopathology.

A further aspect of the present invention is directed to diagnosing cancer, including both early stage development and micro-metastasis and metastasis. The method entails administering to a patient (e.g., a cancer patient or a patient suspected of having cancer) a radiolabeled PDE10 inhibitor, and detecting (e.g., by imaging) differential retention of the label (which becomes indirectly attached to the PDE10 enzyme as a consequence of binding of the enzyme with the inhibitor) in a particular tissue relative to retention of the label in surrounding tissue. The methods may be qualitative or quantitative. In some embodiments, the radiolabel is a radioisotope such as 18F or 11C, and the detecting involves positron emission tomography (PET) imaging, optionally in combination with magnetic resonance imaging (MRI).

BRIEF DESCRIPTION OF THE DRAWINGS

FIGS. 4A-F are photomicrographs showing PDE5A or PDE10A expression by immunohistochemical labeling (brown labeling) in precancerous adenomas and malignant colon tissues obtained from human patients, wherein PDE expression was determined by immunohistochemistry using PDE isozyme specific antibodies, and which show differences in subcellular localization and level of expression between PDE10A and PDE5A (Panels A&C vs. B&D), and that PDE5A and PDE10A were highly expressed in metastatic lesions but not in the surrounding normal liver cells (Panels C&D), and elevated levels of PDE10A in cancer cells (red arrows) compared with adjacent normal appearing cells (blue arrows) (Panels E&F).

DETAILED DESCRIPTION

Figure 1:
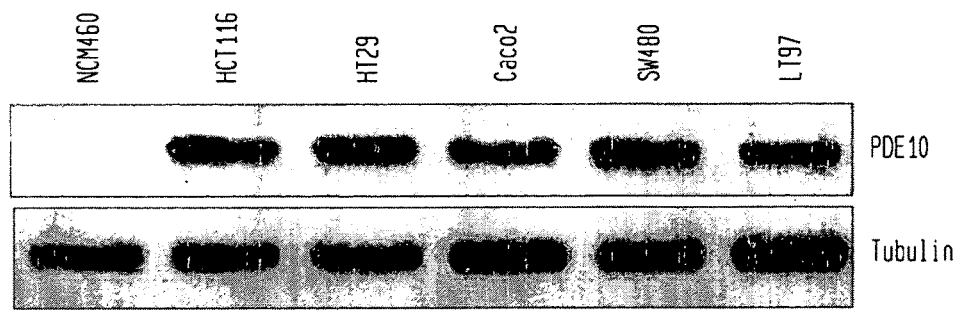
FIG. 1 is a Western blot showing PDE10A expression in a panel of human colon tumor cell lines and a precancerous adenoma cell line (LT97) compared with normal human colonocytes (NCM460), wherein PDE10A protein levels were measured by Western blotting in whole cell lysates using a commercially available PDE10A antibody (GeneTex), and tubulin was used as a control to confirm equal loading of protein in each lane.

In general, a substance is considered to effectively inhibit PDE10A activity if it has a $K_i$ or $IC_{50}$ value of less than or about 1000 nM or more preferably 10 nM. The PDE10A inhibitors of the present invention effectively inhibit PDE10A activity with an $IC_{50}$ value of 20 nM or less, but may also inhibit certain other PDE isozymes such as PDE2, or 5 or have other unidentified targets. The PDE10A inhibitors of the present invention are organic compounds and are non-peptidic and non-biological (i.e., they are not proteins, peptides, nucleic acids, etc.).

The PDE10A inhibitors useful in the practice of the present invention include selective PDE10A inhibitors. As used herein, the term "selective PDE10 inhibitor" refers to an organic molecule that effectively inhibits an enzyme from the PDE10 family to a greater extent than enzymes from the PDE 1-9 families or PDE11 family. In one embodiment, a selective PDE10 inhibitor is a substance, for example an organic molecule, having a $K_i$ or $IC_{50}$ value for inhibition of PDE10A that is less than or about one-tenth the $K_i$ or $IC_{50}$ value that the substance has for inhibition of any other PDE enzyme. In other words, the substance inhibits PDE10A activity to the same degree at a concentration of about one-tenth or less than the concentration required for any other PDE enzyme.

A "selective PDE10A inhibitor" can be identified, for example, by comparing the ability of a substance to inhibit PDE10A activity to its ability to inhibit PDE enzymes from the other PDE families. For example, a substance may be assayed for its ability to inhibit PDE10A activity, as well as PDE1A, PDE1B, PDE1C, PDE2A, PDE3A, PDE3B, PDE4A, PDE4B, PDE4C, PDE4D, PDE5, PDE6, PDE7, PDE8, PDE9, and PDE11 etc.

In some embodiments (e.g., in the context of renal cell carcinoma), the PDE10A inhibitors of the present invention do not contain an indene group. Thus, for example, in these embodiments, the compounds disclosed in U.S. Pat. No. 6,538,029 (and in U.S. Pat. Nos. 5,401,774; 5,965,619; 5,998,477 and 6,063,818 which are referenced therein) are excluded from the scope of the present invention as it pertains to treating renal cancer. In some embodiments (e.g., with respect to "cancer" generally and breast cancer specifically), the PDE10A inhibitors of the present invention also do not contain a pyrrolo-dihydroisoquinoline group (as disclosed in U.S. Pat. No. 6,930,114. In some embodiments (e.g., with respect to "cancer" generally), the PDE10A inhibitors of the present invention also do not contain an imidazotriazine that is unfused to or not part of a larger ring system (e.g., as disclosed in U.S. Patent Application Publication 2006/0166992 A1). The PDE10A inhibitors of the present invention also exclude papaverine.

In some embodiments, the PDE10A inhibitor may be represented by the following structure:

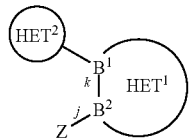

wherein z is

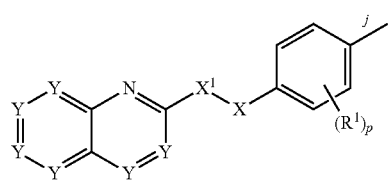

and wherein $R_1$ is each independently selected from a group consisting of hydrogen, halogen, hydroxyl, cyano, $C_1$ to $C_8$ alkyl, $C_2$ to $C_8$ alkenyl, $C_2$ to $C_8$ alkynyl, $C_1$ to $C_8$ alkoxy, $C_1$ to $C_8$ haloalkyl, $C_3$ to $C_8$ cycloalkyl, $C_3$ to $C_8$ cycloalkyl-$C_1$ to $C_8$ alkyl, 4 to 7 membered heterocycloalkyl, $C_1$ to $C_8$ alkylthio, —$NR^3R^3$, —O—$CF_3$, —S(O) n-$R^3$, C(O)—$NR^3R^3$, and $C_1$ to $C_8$ alkyl substituted with a heteroatom wherein the heteroatom is selected from a group consisting of nitrogen, oxygen and sulfur and wherein the heteroatom may be further substituted with a substituent selected from a group consisting of hydrogen, $C_1$ to $C_8$ alkyl, $C_3$ to $C_8$ cycloalkyl, $C_2$ to $C_8$ alkenyl, $C_2$ to $C_8$ alkynyl, and $C_1$ to $C_8$ haloalkyl;

each $R^3$ is independently selected from a group consisting of hydrogen, $C_1$ to $C_8$ alkyl, $C_2$ to $C_8$ alkenyl, $C_2$ to $C_8$ alkynyl, $C_1$ to $C_8$ haloalkyl, $C_3$ to $C_8$ cycloalkyl;

$R^2$ is selected from the group consisting of hydrogen, $C_1$ to $C_8$ alkyl, $C_3$ to $C_8$ cycloalkyl-$C_1$ to $C_8$ alkyl, $C_2$ to $C_8$ alkenyl, $C_2$ to $C_8$ alkynyl, $C_1$ to $C_8$ haloalkyl and $C_3$ to $C_8$ cycloalkyl;

$HET^1$ is selected from a group consisting of a monocyclic heteroaryl and a bicyclic heteroaryl, wherein the monocyclic and bicyclic heteroaryl may be optionally substituted with at least one $R^4$ and;

$R^4$ is selected from a group consisting of halogen, hydroxyl, cyano, $C_1$ to $C_8$ alkyl, $C_2$ to $C_8$ alkenyl, $C_2$ to $C_8$ alkynyl, $C_1$ to $C_8$ alkoxy, $C_3$ to $C_8$ cycloalkyl, $C_3$ to $C_8$ cycloalkyl-$C_1$ to $C_8$ alkyl, $C_1$ to $C_8$ alkylthio, and $C_1$ to $C_8$ alkyl substituted with a substituent is selected from the group consisting of —$OR^8$, —$NR^8R^8$, and —$SR^8$, wherein $R^8$ is independently selected from the group consisting of hydrogen and $C_1$ to $C_8$ alkyl $HET^2$ is a monocyclic or bicyclic heteroaryl, wherein the monocyclic and bicyclic heteroaryl optionally substituted with at least one $R^5$, with the proviso that $HET^2$ is not tetrazole;

$R^5$ is independently selected from a group consisting of halogen, hydroxyl, cyano, $C^1$ to $C_8$ alkyl, $C_2$ to $C_8$ alkenyl, $C_2$ to $C_8$ alkynyl, $C_1$ to $C_8$ alkoxy, $C_3$ to $C_8$ cycloalkyl, $C_3$ to $C_8$ cycloalkyl-$C_1$, to $C_8$ alkyl, $C_1$ to $C_8$ alkylthio, —$NR^7R^7$ and $C_1$ to $C_8$ haloalkyl;

$B^1$ and $B^2$ are adjacent atoms in $Het^1$ which are independently selected from a group consisting of carbon and nitrogen;

bond j is a covalent bond between Z and $B^2$;
bond k is a covalent bond in $Het^1$ between $B^1$ and $B^2$;
X and $X^1$ are each independently selected from the group consisting of oxygen, sulfur, $C(R_2)_2$ and $NR_2$; provided that at least one of X or $X^1$ is carbon;

Y is selected from a group consisting of carbon and nitrogen, provided that when Y is carbon it is substituted with $R^6$;

wherein each $R^6$ is independently selected from a group consisting of hydrogen, halogen, hydroxyl, cyano, $C_1$ to $C_8$ alkyl, $C_2$ to $C_8$ alkenyl, $C_2$ to $C_8$ alkynyl, $C_1$ to $C_8$ alkoxy, $C_1$ to $C_8$ cycloalkyl, $C_3$ to $C_8$ cycloalkyl-$C_1$, to $C_8$ alkyl, $C_1$ to $C_8$ alkylthio, $C_1$ to $C_8$ haloalkyl, —$NR^7R^7$, —O—$CF_3$, —S(O)m-$R^7$, and C(O)—$NR^7R^7$, $C_1$ to $C_8$ alkyl substituted with a heteroatom wherein the heteroatom is selected from a group consisting of nitrogen, oxygen and sulfur and wherein the heteroatom may be further substituted with a substituent selected from the group consisting of hydrogen, $C_1$ to $C_8$ alkyl, $C_3$ to $C_8$ cycloalkyl, $C_2$ to $C_8$ alkenyl, $C_2$ to $C_8$ alkynyl and $C_1$ to $C_8$ haloalkyl;

wherein each $R^7$ is independently selected from the group consisting of hydrogen and $C_1$-$C_8$ alkyl; p is 1, 2 or 3; n is 0, 1 or 2; and m is 0, 1 or 2.

In some embodiments, the PDE10A inhibitor represented by the above formula is 2-[4-(1-methyl-4-pyridin-4-yl-1H-pyrazol-3-yl)-phenoxymethyl]-quinoline, also known as PF-2545920 or MP-10. In some embodiments, the PDE10A inhibitor represented by the above formula is 2-{4-[-Pyridin-4-yl-1-(2,2,2-trifluoro-ethyl)-1H-pyrazol-3-yl]-phenoxymethyl}-quinoline, also known as TP-10. PDE10A inhibitors structurally related to PF-2545920 and TP-10 displaying moderate PDE10A inhibitory activity and selectivity, and which are also represented by the above formula, may also be useful for use in the present invention. Representative examples of such compounds include 2-[-4-(4-Pyridin-4-yl-2H-pyrazol-3-yl)-phenoxymethyl]-quinoline; 2-[4-(2-Methyl-4-pyridin-4-yl-2H-pyrazol-3-yl)-phenoxymethyl]-quinoline; 2-[4-(1-Methyl-4-pyridin-4-yl-1H-pyrazol-3-yl)-phenoxymethyl]-quinoline; 2-[4-(2-Ethyl-4-pyridin-4-yl-2H-pyrazol-3-yl)-phenoxymethyl]-quinoline; 2-[4-(1-Ethyl-4-pyridin-4-yl-1H-pyrazol-3-yl)-phenoxymethyl]-quinoline; dimethyl-(2-{4-pyridin-4-yl-3-[4-(quinolin-2-yl-methoxy)-phenyl]-pyrazol-1-yl}-ethyl)-amine; Dimethyl-(2-{4-pyridin-4-yl-5-[4-(quinolin-2-ylmethoxy)-phenyl]-pyrazol-1-yl}-ethyl)-amine; 2-{4-[-Pyridin-4-yl-2-(2,2,2-trifluoro-ethyl)-2H-pyrazol-3-yl]-phenoxymethyl1-quinoline; 2-{4-[-Pyridin-4-yl-1-(2,2,2-trifluoro-ethyl)-1H-pyrazol-3-yl]-phenoxymethyl}-quinoline; 1-{4-Pyridin-4-yl-3-[4-(quinolin-2-yl-methoxy)-phenyl]-pyrazol-1-yl}-propan--2-ol; 1-{4-Pyridin-4-yl-5-[4-(quinolin-2-yl-methoxy)-phenyl]-pyrazol-1-yl}-propan- 2-ol; 2-[4-(2-Isopropyl-4-pyridin-4-yl-2H-pyrazol-3-yl)-phenoxymethyl]-quinoline; 2-[4-(4-Pyridin-4-yl-isoxazol-5-yl)-phenoxymethyl]-quinoline; 2-[4-(5-Pyridin-4-yl-pyrimidin-4-yl)-phenoxymethyl]-quinoline; 2-[4-(2-Methyl-5-pyridin-4-yl-pyrimidin-4-yl)-phenoxymethyl]-quinoline; 2-[4-(2-Methyl-6-pyridin-4-yl-pyrazolo[1,5-a]pyrimidin-7-yl)-phenoxymethyl-]-quinoline; 2-[4-(2-Methyl-6-pyridin-4-yl-[1,2,4]triazolo[1.5-a]pyrimidin-7-yl)-phenoxymethyl]-quinoline; 2-[4-(4-Pyridazin-4-yl-2H-pyrazol-3-yl)-phenoxymethyl]-quinoline; 2-[4-(1-Methyl-4-pyridazin-4-yl-1H-pyrazol-3-yl)-phenoxymethyl]-quinoline; 2-[4-(2-Methyl-4-pyridazin4-yl-2H-pyrazol-3-yl)-phenoxymethyl]-quinoline; 2-[-4-(4-Pyrimidin-4yl-2H-pyrazol-3-yl)-phenoxymethyl]-quinoline; 2-[4-(4-Pyridazin-3-yl-2H-pyrazol-3-yl)-phenoxymethyl]-quinoline; 2-{4-[4-(3-Methyl-isoxazol-5-yl)-2H-pyrazol-3-yl]-phenoxymethyl]-quinoline; 2-{4-[2-Methyl-4-(3-methyl-isoxazol-5-yl)-2H-pyrazol-3-yl]-phenoxymethyl)-quinoline; 2-{4-[1-Methyl-4-(3-methyl-isoxazol-5-yl)-1H-pyrazol-3-yl]-phenoxymethyl}-quinoline; 2-{4-[2-Methyl-5-(3-methyl-isoxazol-5-yl)-pyrimidin-4-yl]-phenoxymethyl}-quinoline; 2-[4-(2-Pyridin-4-yl-2H-pyrazol-3-yl)-phenoxymethyl]-quinoline; 2-[4-(3-Methyl-5-pyridin-4-yl [1,2,4]triazol-4-yl)-phenoxymethyl]-quinoline; 2-[4-(1-Methyl-4-pyridin-4-yl-1H-pyrazol-3-yl)-phenoxymethyl]-quinoxaline; 7-Chloro-2-[4-(1-methyl-4-pyridin-4-yl-1H-pyrazol-3-yl)-phenoxymethyl]-quinoline hydrogen chloride; 6-Fluoro-2-[4-(1-methyl-4-pyridin-4-yl-1H-pyrazol-3-yl)-phenoxymethyl]-quinoline hydrogen chloride; 2-[2-Fluoro-4-(4-pyridin-4-yl-1H-pyrazol-3-yl)-phenoxymethyl]-quinoline; 2-[2-Fluoro-4-(1-methyl-4-pyridin-4-yl-1H-pyrazol-3-yl)-phenoxymethyl]-quinoline; 2-[2,3-Difluoro-4-(1-methyl-4-pyridin-4-yl-1H-pyrazol-3-yl)-phenoxymethyl]-quinoline; 2-[3-Fluoro-4-(4-pyridin-4-yl-1H-pyrazol-3-yl)-phenoxymethyl]-quinoline; 2-[4-(5-Pyridin-4-yl-1H-pyrazol-4-yl)-phenoxymethyl]-quinoline; 2-[4-(1-Methyl-5-pyridin-4-yl-1H-pyrazol-4-yl)-phenoxymethyl]-quinoline; 2-[4-(1-Methyl-3-pyridin-4-yl-1H-pyrazol-4-yl)-phenoxymethyl]-quinoline; 2-Methyl-1-{4-pyridin-4-yl-3-[4-(quinolin-2-yl-methoxy)-phenyl]-pyrazol-1-yl}-propan-2-ol; 2-Methyl-1-{4-pyridin-4-yl-5-[4-(quinolin-2-yl-methoxy)-phenyl]-pyrazol-1-yl}-propan-2-ol; (R)-1-{4-Pyridin-4-yl-3-[4-(quinolin-2-ylmethoxy)-phenyl]-pyrazol-1-yl}-propan-2-ol; (S)-1-{4-Pyridin-4-yl-3-[4-(quinolin-2-yl-methoxy)-phenyl]-pyrazol-1-yl}-propan-2-ol; 2-[4-(1-Isopropyl-4-pyridin-4-yl-1H-pyrazol-3-yl)-phenoxymethyl]-quinoline; 2-[4-(1-Isobutyl-4-pyridin-4-yl-1H-pyrazol-3-yl)-phenoxymethyl]-quinoline; 2-[4-(1-Methyl-4-pyridin-4-yl-1H-pyrazol-3-yl)-phenoxymethyl]-[1.8]Naphthyridine; 2-{2-[4-(4-Pyridin-4-yl-2H-pyrazol-3-yl)-phenyl]-ethyl}-quinoline; 2-(2-[4-(1-Methyl-4-pyridin-4-yl-1H-pyrazol-3-yl)-phenyl]-ethyl]-quinoline; 2-{4-[4-(2-Chloro-pyridin-4-yl)-1H-pyrazol-3-yl]-phenoxymethyl}-quinoline; 2-{4-[4-(2-Chloro-pyridin-4-yl)-1-methyl-1H-pyrazol-3-yl]-phenoxymethyl}-quinoline; 2-{4-[1-Methyl-4-(2-methyl-pyridin-4-yl)-1H-pyrazol-3-yl]-phenoxymethyl}-quinoline; Dimethyl-(4-{1-methyl-3-[4-(quinolin-2-yl-methoxy)-phenyl]-1H-pyrazol-4-yl}-pyridin-2-yl)-amine; 2-[4-(5-Pyridin-4-yl-pyrazol-1-yl)-phenoxymethyl]-quinoline; 2-[4-(3-Methyl-5-pyridin-4-yl-pyrazol-1-yl)-phenoxymethyl]-quinoline; 2-[2-Chloro-4-(4-pyridin-4-yl-1H-pyrazol-3-yl)-phenoxymethyl]-quinoline; 2-[2-Chloro-4-(1-methyl-4-pyridin-4-yl-1H-pyrazol-3-yl)-phenoxymethyl]-quinoline; 2-[4-(4-Pyridin-4-yl-4H-[1,2,4]triazol-3-yl)-phenoxymethyl]-quinoline; 2-[4-(5-Pyridin-4-yl-[1,2,4]triazol-1-yl)-phenoxymethyl]-quinoline; 2-[4-(3-Methyl-5-pyridin-4-yl-[1,2,4]triazol-1-yl)-phenoxymethyl]-quinoline; 2-[4-(2-Pyridin-4-yl-2H-[1,2,4]triazol-3-yl)-phenoxymethyl]-quinoline; 2-[4-(5-Methyl-2-pyridin-4-yl-2H-[1,2,4]triazol-3-yl)-phenoxymethyl]-quinoline; 2-{4-[4-Pyridin-4-yl-1-(2,2,2-trifluoro-ethyl)-1H-pyrazol-3-yl]-phenoxymethyl}-quinoxaline; 8-Methoxy-2-[4-(1-methyl-4-pyridin-4-yl-1H-pyrazol-3-yl)-phenoxymethyl]-quinoline; 2-[4-(1-Methyl-4-pyridin-4-yl-1H-pyrazol-3-yl)-phenoxymethyl]-pyrido[1,2-a-]pyrimidin-4-one; 2-[4-(1-Methyl-4-pyridin-4-yl-1H-pyrazol-3-yl)-phenoxymethyl]-quinazoline; 2-[3-Fluoro-4-(1-methyl-4-pyridin-4-yl-1H-pyrazol-3-yl)-phenoxymethyl]-quinoline; 2-(3-Fluoro-4-[4-pyridin-4-yl-1-(2,2,2-trifluoro-ethyl)-1H-pyrazol-3-yl]-p-henoxymethyl}-quinoline; 2-{3-Fluoro-4-[4-pyridin-4-yl-1-(2,2,2-trifluoro-ethyl)-1H-pyrazol-3-yl]-p-henoxymethyl}-quinoxaline; 4-Chloro-2-[4-(1-methyl4-pyridin-4-yl-1H-pyrazol-3-yl)-phenoxymethyl]-quinoline; 4-Methoxy-2-[4-(1-methyl-4-pyridin-4-yl-1H-pyrazol-3-yl)-phenoxymethyl]-quinoline; Dimethyl-{2-[4-(1-methyl-4-pyridin-4-yl-1H-pyrazol-3-yl)-phenoxymethyl]-quinolin-4-yl}-amine; 2-[4-(1-Methyl-4-pyridin-4-yl-1H-pyrazol-3-yl)-benzyloxy]-quinoline disuccinic acid; 2-((4-(5-(pyridin-4-yl)oxazol-4-yl)phenoxy)methyl)quinoline; 2-((4-(2-methyl-5-(pyridin-4-yl)oxazol-4-yl)phenoxy)methyl)quinoline; 2-((4-(3-Methyl-4-(pyridin-4-yl)-1H-pyrazol-5-yl)phenoxy)methyl)quinoline; 2-((4-(1,3-dimethyl-4-(pyridin-4-yl)-1H-pyrazol-5-yl)phenoxy)methyl)quinoline; 2-((4-(1,5-dimethyl-4-(pyridin-4-yl)-1H-pyrazol-3-yl)phenoxy)methyl)quinoline; 2-(1-(4-(1-methyl-4-(pyridin-4-yl)-1H-pyrazol-3-yl)phenoxy)ethyl)quinoline; 2-((4-(5-(pyridin-4-yl)-1,2,3-triazol-4-yl)phenoxy)methyl)quinoline; 2-((4-(2-methyl-5-(pyridin-4-yl)-2H-1,2,3-triazol-4-yl)phenoxy)methyl)quinoline; 2-((4-(3-methyl-5-(pyridin-4-yl)-3H-1,2,3-triazol-4-yl) phenoxy)methyl)quinoline; 2-((4-(1-(pyridin-4-yl)-1H-imidazol-2-yl)phenoxy)methyl) quinoline; 2-((4-(5-(pyridin-4-yl)-1H-imidazol-1-yl) phenoxy)methyl)quinoline; 2-((4-(2-methyl-5-(pyridin-4-yl)-1H-imidazol-1-yl)phenoxy)methyl)quinoline; 2-((4-(2-ethyl-5-(pyridin-4-yl)-1H-imidazol-1-yl)phenoxy)methyl) quinoline; and 2-((4-(2-(pyridin-4-yl)-1H-imidazol-1-yl) phenoxy)methyl)quinoline.

Methods of making PF-2545920 and TP-10 and the structurally related compounds (including the compounds listed above) are described in U.S. Pat. No. 7,429,665.

In some embodiments of the present invention, the PDE10A inhibitors are represented by the following formula:

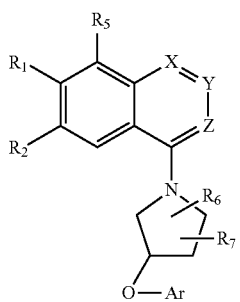

wherein X, Y and Z are each independently CH or N with the proviso that at least one or two of X, Y and Z are N, but not all three, and with the proviso that Y and Z are not both N;

wherein $R_1$, $R_2$ and $R_5$ are independently H, halogen, C≡N, —COOH, —COOR$_3$, —CON R$_3$R$_4$, COR$_3$, —NR$_3$R$_4$, —NHCOR$_3$, —OH, ($C_6$-$C_{10}$)aryl, 5 to 7 membered heteroaryl, ($C_1$-$C_6$)alkyl, ($C_1$-$C_6$)haloalkyl ($C_2$-$C_6$)alkenyl, ($C_2$-$C_6$)alkynyl, —O—($C_1$-$C_6$)alkyl, —o—($C_2$-$C_6$)alkenyl or ($C_3$-$C_8$) cycloalkyl; or, when $R_1$, $R_2$ and $R_5$ are independently —O—($C_1C_6$)alkyl, —O—($C_2$-$C_6$)alkenyl, ($C_1$-$C_6$) alkyl, ($C_2$-$C_6$) alkenyl or ($C_2$-$C_6$)alkynyl, $R_1$ and $R_2$ or $R_1$ and $R_5$ may optionally be connected to form a 5 to 8 membered ring;

wherein $R_3$ and $R_4$ are independently H, ($C_1$-$C_6$)alkyl or ($C_6$-$C_{10}$)aryl said aryl optionally substituted with one or more ($C_1$-$C_6$)alkyl groups;

wherein $R_6$ and $R_7$ are each independently H, halogen, —COOR$_3$, —CONR$_3$R$_4$, —COR$_4$, NR$_3$R$_4$, —NHCOR$_3$, —OH, —($C_1$-$C_6$)alkylene-OH, —HNCOOR$_3$, —CN, —HNCONHR$_4$, ($C_1$-$C_6$)alkyl, ($C_2$-$C_6$)alkoxy, $C_6$-$C_{10}$ aryl or

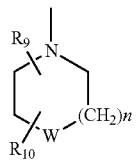

wherein n is 0 or 1;

W is carbon, oxygen or NR$_8$, wherein $R_8$ is hydrogen or ($C_1C_6$)alkyl, and when W is carbon, it may be optionally substituted by halogen, —C≡N, —COOH, —COOR$_3$, —CONR$_3$R$_4$, —COR$_3$, —NR$_3$R$_4$, —NHCOR$_3$, —OH, ($C_6$-$C_{10}$) aryl, 5 to 7 membered heteroaryl, ($C_1$-$C_6$)alkyl, ($C_1$-$C_6$)haloalkyl ($C_2$-$C_6$)alkenyl, ($C_2$-$C_6$)alkynyl, —O—($C_1$-$C_6$)alkyl, —O—($C_2$-$C_6$)alkenyl or ($C_3$-$C_8$)cycloalkyl;

wherein $R_9$ and $R_{10}$ are independently hydrogen or ($C_1$-$C_8$)alkyl;

or $R_9$ and $R_{10}$ may optionally combine to form a cyclic ring;

wherein Ar is phenyl, naphthyl, or a 5- to 6-membered heteroaryl ring, which heteroaryl is optionally fused to a benzo group, and which heteroaryl contains from one to four heteroatoms selected from oxygen, nitrogen and sulfur, with the proviso that said heteroaryl ring cannot contain two adjacent oxygen atoms or two adjacent sulfur atoms, and wherein each of the foregoing phenyl, naphthyl, heteroaryl, or benzo-fused heteroaryl rings may optionally be substituted with from one to three substituents independently selected from ($C_1$-$C_8$)alkyl, chloro-, bromo-, iodo, fluoro-, ($C_1C_8$) hydroxyalkyl-, ($C_1$-$C_8$) alkoxy- ($C_1$-$C_8$) alkyl-, ($C_3$-$C_8$)hydroxycycloalkyl-, ($C_3$-$C_8$)cycloalkyl, ($C_3$-$C_8$)cycloalkoxy-, ($C_1$-$C_8$)alkoxy-($C_3$-$C_8$)cycloalkyl-, (3-8 membered) heterocycloalkyl, hydroxyl(3-8 membered)heterocycloalkyl, and ($C_1$-$C_8$)alkoxy(3-8 membered)heterocycloalkyl, wherein said alkyl, alkoxy and cycloalkyl may be optionally substituted with 1 to 3 halos and wherein each ($C_3$-$C_8$)cycloalkyl or heterocycloalkyl moiety may be independently substituted with from one to three ($C_1$-$C_8$)alkyl or benzyl groups; or wherein Ar is a 5- to 6-membered heteroaryl ring, which heteroaryl is fused to an imidazo, pyrido, pyrimido, pyrazo, pyridazo, or pyrrolo group, and which heteroaryl contains from one to four heteroatoms selected from oxygen, nitrogen and sulfur, with the proviso that said heteroaryl ring cannot contain two adjacent oxygen atoms or two adjacent sulfur atoms, and wherein each of the foregoing fused heteroaryl rings may optionally be substituted with from one to three substituents independently selected from ($C_1$-$C_8$)alkyl, chloro-, bromo-, iodo, fluoro-, halo($C_1$-$C_8$)alkyl, ($C_1$-$C_8$)hydroxyalkyl-, ($C_1$-$C_8$)alkoxy-($C_1$-$C_8$)alkyl-, —O—($C_1$-$C_8$)alkyl-halo, ($C_3$-$C_8$)hydroxycycloalkyl-, ($C_3$-$C_8$)cycloalkyl, ($C_3$-$C_8$)cycloalkoxy-, ($C_1$-$C_8$) alkoxy-($C_3$-$C_8$)cycloalkyl-, (3-8 membered) heterocycloalkyl, hydroxyl(3-8 membered) heterocycloalkyl, and ($C_1$-$C_8$)alkoxy-(3-8 membered)heterocycloalkyl, wherein each ($C_3$-$C_8$)cycloalkyl or heterocycloalkyl moiety may be independently substituted with from one to three ($C_1$-$C_6$)alkyl or benzyl groups; or when Ar is phenyl, naphthyl, or heteroaryl ring, each ring may be optionally substituted with one to three substituents independently selected from (a) lactone formed from —($CH_2$)$_t$H with an ortho —COOH, wherein t is one, two or three; (b) —CONR$_{14}$R$_{15}$, wherein $R_{14}$ and $R_{15}$ are independently selected from ($C_1$-$C_8$)alkyl and benzyl, or $R_{14}$ and $R_{15}$ together with the nitrogen to which they are attached form a 5- to 7-membered heteroalkyl ring that may contain from zero to three heteroatoms selected from nitrogen, sulfur and oxygen in addition to the nitrogen of the —CONR$_{14}$R$_{15}$ group, wherein when any of said heteroatoms is nitrogen it may be optionally substituted with ($C_1$-$C_8$)alkyl or benzyl, with the proviso that said ring cannot contain two adjacent oxygen atoms or two adjacent sulfur atoms; or (c) —($CH_2$)$_v$NCOR$_{14}$R$_{15}$ wherein v is zero, one, two or three and —COR$_{14}$R$_{15}$ taken together with the nitrogen to which they are attached form a 4- to 6-membered lactam ring.

Specific PDE10A inhibitors that are represented by the formula above and which may be suitable for use in the present invention include the following:

4-[3-Allyl-4-(quinoxalin-2-yloxy)-pyrrolidin-1-yl]-6, 7-dimethoxy-quinazoline;

6,7-Dimethoxy-4-[3-propyl-4-(quinoxalin-2-yloxy)-pyrrolidin-1-yl]-quinazoline;

1-(6,7-Dimethoxy-quinazolin-4-yl)-3-methyl-4-(quinoxalin-2-yloxy)-pyrrolidine-3-carboxylic acid ethyl ester;

6,7-Dimethoxy-4-[3-methyl-3-(quinoxalin-2-yloxy)-pyrrolidin-1-yl]-quinazoline;

[1-(6,7-Dimethoxy-quinazolin-4-yl)-4-(quinoxalin-2-yloxy)-pyrrolidin-3-yl]-isopropylmethyl-amine;

[1-(6,7-Dimethoxy-quinazolin-4-yl)-4-(quinoxalin-2-yloxy)-pyrrolidin-3-yl]-diethylamine;

[1-(6,7-Dimethoxy-quinazolin-4-yl)-4-(quinoxalin-2-yloxy)-pyrrolidin-3-yl]-ethyl-methyl-amine;
[1-(6,7-Dimethoxy-quinazolin-4-yl)-4-(quinoxalin-2-yloxy)-pyrrolidin-3-yl]-dimethyl-amine;
[1-(6,7-Dimethoxy-quinazolin-4-yl)-4-(quinolin-2-yloxy)-pyrrolidin-3-yl]-dimethyl-amine;
[1-(6,7-Dimethoxy-quinazolin-4-yl)-4-(quinolin-3-yloxy)-pyrrolidin-3-yl]-dimethyl-amine;
6,7-Dimethoxy-4-[4'-(quinoxalin-2-yloxy)-[1,3']bipyrrolidinyl-1'-yl]-quinazoline;
6,7-Dimethoxy-4-[3-morpholin-4-yl-4-(quinoxalin-2-yloxy)-pyrrolidin-1-yl]-quinazoline;
6,7-Dimethoxy-4-[3-(4-methyl-piperazin-1-yl)-4-(quinoxalin-2-yloxy)-pyrrolidin-1-yl]-quinazoline;
[1-(6,7-Dimethoxy-quinazolin-4-yl)-4-(quinoxalin-2-yloxy)-pyrrolidin-3-yl]-methyl-amine;
N-[1-(6,7-Dimethoxy-quinazolin-4-yl)-4-(quinoxalin-2-yloxy)-pyrrolidin-3-yl]-N-methylacetamide;
6,7-Dimethoxy-4-[3-(quinoxalin-2-yloxy)-pyrrolidin-1-yl]-quinazoline;
4-[3-(4-Ethoxy-phenoxy)-pyrrolidin-1-yl]-6,7-dimethoxy-quinazoline;
6,7-Dimethoxy-4-[3-(naphthalen-2-yloxy)-pyrrolidin-1-yl]-quinazoline;
4-[3-(4-tert-Butyl-phenoxy)-pyrrolidin-1-yl]-6,7-dimethoxy-quinazoline;
4-[1-(6,7-Dimethoxy-quinazolin-4-yl)-pyrrolidin-3-yloxy]-benzonitrile;
6,7-Dimethoxy-4-[3-(4-trifluoromethoxy-phenoxy)-pyrrolidin-1-yl]-quinazoline;
4-[3-(3-Ethoxy-phenoxy)-pyrrolidin-1-yl]-6,7-dimethoxy-quinazoline;
4-[3-(3,4-Dimethoxy-phenoxy)-pyrrolidin-1-yl]-6,7-dimethoxy-quinazoline;
4-[3-(3-isopropoxy-phenoxy)-pyrrolidin-1-yl]-6,7-dimethoxy-quinazoline;
4-[3-(indan-5-yloxy)-pyrrolidin-1-yl]-6,7-dimethoxy-quinazoline;
6,7-Dimethoxy-4-[3-(quinolin-6-yloxy)-pyrrolidin-1-yl]-quinazoline;
N4-[3-(Biphenyl-3-yloxy)-pyrrolidin-1-yl]-6,7-dimethoxy-quinazoline;
6,7-Dimethoxy-4-[3-(2-methyl-quinolin-6-yloxy)-pyrrolidin-1-yl]-quinazoline;
6,7-Dimethoxy-4-[3-(7-methoxy-naphthalen-2-yloxy)-pyrrolidin-1-yl]-quinazoline;
6,7-Dimethoxy-4-[3-(6-methoxy-naphthalen-2-yloxy)-pyrrolidin-1-yl]-quinazoline;
6,7-Dimethoxy-4-[3-(quinolin-7-yloxy)-pyrrolidin-1-yl]-quinazoline;
6,7-Dimethoxy-4-[3-(naphthalen-1-yloxy)-pyrrolidin-1-yl]-quinazoline;
4-[3-(isoquinolin-3-yloxy)-pyrrolidin-1-yl]-6,7-dimethoxy-quinazoline;
4-[3-(isoquinolin-7-yloxy)-pyrrolidin-1-yl]-6,7-dimethoxy-quinazoline;
6,7-Dimethoxy-4-[3-(pyridin-2-yloxy)-pyrrolidin-1-yl]-quinazoline;
6,7-Dimethoxy-4-[3-(pyridin-3-yloxy)-pyrrolidin-1-yl]-quinazoline;
6,7-Dimethoxy-4-[3-(pyridin-4-yloxy)-pyrrolidin-1-yl]-quinazoline;
4-[3-(5-Chloro-pyrimidin-2-yloxy)-pyrrolidin-1-yl]-6,7-dimethoxy-quinazoline;
3-[1-(6,7-Dimethoxy-quinazolin-4-yl)-pyrrolidin-3-yloxy]-quinoxaline-6-carbonitrile acid tert-butyl ester;
6,7-Dimethoxy-4-[3-methoxy-4-(quinoxalin-2-yloxy)-pyrrolidin-1-yl]-quinazoline;
1-(6,7-Dimethoxy-quinazolin-4-yl)-4-(quinoxalin-2-yloxy)-pyrrolidin-3-ol;
[4-Benzyl-1-(6,7-dimethoxy-quinazolin-4-yl)-pyrrolidin-3-yl]-dimethyl-amine;
6,7-Dimethoxy-4-[3-(quinoxalin-2-yloxy)-pyrrolidin-1-yl]-cinnoline;
6,7-Dimethoxy-4-[4'-(quinoxalin-2-yloxy)-[1,3']bipyrrolidinyl-1'-yl]-cinnoline;
[1-(6,7-Dimethoxy-cinnolin-4-yl)-4-(quinolin-2-yloxy)-pyrrolidin-3-yl]-ethyl-methyl-amine
[1-(6,7-Dimethoxy-cinnolin-4-yl)-4-(quinolin-2-yloxy)-pyrrolidin-3-yl]-diethyl-amine;
6,7-Dimethoxy-4-[3-morpholin-4-yl-4-(quinoxalin-2-yloxy)-pyrrolidin-1-yl]-cinnoline;
[1-(6,7-Dimethoxy-cinnolin-4-yl)-4-(quinoxalin-2-yloxy)-pyrrolidin-3-yl]-diethyl-amine;
[1-(6,7-Dimethoxy-cinnolin-4-yl)-4-(quinoxalin-2-yloxy)-pyrrolidin-3-yl]-ethyl-methyl-amine
[1-(6,7-Dimethoxy-cinnolin-4-yl)-4-(quinolin-2-yloxy)-pyrrolidin-3-yl]-dimethyl-amine;
6,7-Dimethoxy-4-[3-morpholin-4-yl-4-(quinolin-2-yloxy)-pyrrolidin-1-yl]-cinnoline;
6,7-Dimethoxy-4-[4'-(quinolin-2-yloxy)-[1,3']bipyrrolidinyl-1'-yl]-cinnoline;
4-[3-(4a,5,6,7,8,8a-Hexahydro-quinoxalin-2-yloxy)-pyrrolidin-1-yl]-6,7-dimethoxyquinazoline;
1-(6,7-Dimethoxy-quinazolin-4-yl)-4-(quinoxalin-2-yloxy)-pyrrolidine-2-carboxylic acid dimethylamide;
[1-(6,7-Dimethoxy-quinazolin-4-yl)-4-(quinoxalin-2-yloxy)-pyrrolidin-2-yl]-methanol hydrochloride; and
2-[1-(6,7-Dimethoxy-quinazolin-4-yl)-4-(quinoxalin-2-yloxy)-pyrrolidin-2-yl]-propan-2-ol hydrochloride.

These compounds are disclosed in WO 2006/070284. In some embodiments the PDE10A inhibitor represented by the above formula is 6,7-Dimethoxy-4-[3-(quinoxalin-2-yloxy)-pyrrolidin-1-yl]-quinazoline or 6,7-dimethoxy-4-[(3R)-3-(2-quinoxalinyloxy)-1-pyrrolidinyl]quinazoline, also known as PQ-10. PQ-10 is also described in Kähler et al., Am. J. of Med. Gen. B: Neuropsychiatric Genetics 1538(1): 86-96 (2010); Menniti et al., Nature Rev. Drug Discov. 5:660-670 (2006); and Chappie, et al., J. Med. Chem. 50:182-7 (2007) (PQ-10 is described therein as compound no. 29). Other structurally related compounds that may be suitable for use in the present invention are disclosed in WO 2008/006372 and U.S. Patent Application Publication 2006/001975 A1.

In some embodiments, the PDE10A inhibitor is represented by the formula:

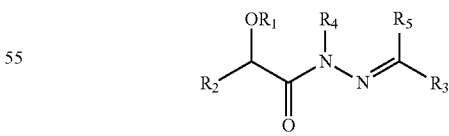

wherein $R_1$ is $C_{1-6}$ alkyl, $C_{1-6}$ haloalkyl, $-(CH_2)_n O(CH_2)_m CH_3$ or $-(CH_2)_n N(CH_3)_2$; $R_2$ is substituted or unsubstituted heterocyclyl, substituted phenyl, or substituted or unsubstituted naphthyl; $R_3$ is substituted or unsubstituted heterocyclyl, or substituted or unsubstituted aryl; and $R_4$ and $R_5$ are the same or different and independently hydrogen, $C_{1-6}$ alkyl or $C_{1-6}$ haloalkyl; n is 1, 2, 3, 4, 5 or 6; and m is 0, 1, 2, 3, 4, 5 or 6. These compounds and methods of making them are disclosed in U.S. Pat. No. 8,377,930. In some embodiments, the PDE10 inhibitor represented by the above formula is (E)-2-{4-(1H-pyrazol-1-yl)phenyl}-N'-(4-bromo-3,5-dimethoxybenzylidene)-2-methoxyacetohydrazide (compound 12-104 in the '930 Patent, and compound no. 55 in Cutshall, et al., Bioorg. Med. Chem. Lett. 22:5595-9 (2012)).

In some embodiments, the PDE10A inhibitor may be represented by the following formula:

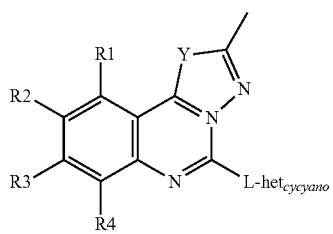

wherein R1-R4 are selected from the group consisting of H; $C_1$-$C_6$ alkyl such as methyl; halogen such as chlorine and bromine; cyano; halo($C_1$-$C_6$)alkyl such as trifluoromethyl; aryl such as phenyl; alkoxy, such as methoxy, dimethoxy, ethoxy, methoxy-ethoxy and ethoxy-methoxy; and $C_1$-$C_6$ hydroxyalkyl such as $CH_2CH_2OH$; and wherein het is cyano (—C≡N—) or is selected from the group consisting of

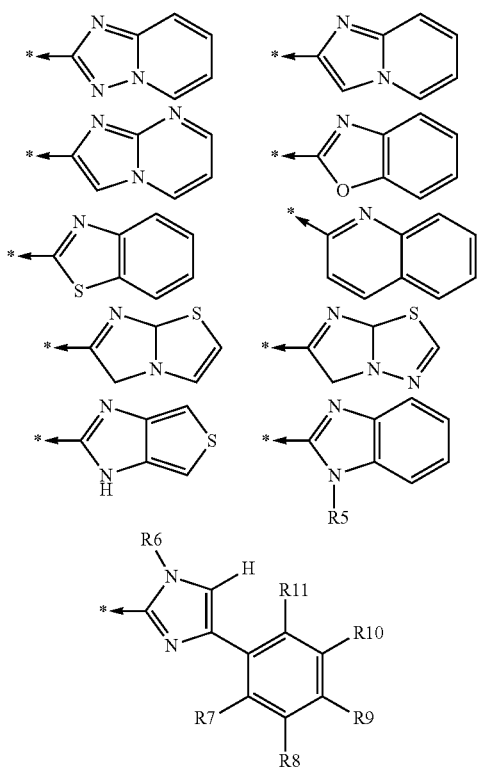

wherein * denotes the attachment point;, and wherein R5 and R6 are selected from the group consisting of H; $C_1$-$C_6$ alkyl such as methyl, ethyl, 1-propyl, 2-propyl, isobutyl, n-butyl, sec-butyl or tert-butyl; $C_1$-$C_6$ alkyl($C_3$-$C_8$)cycloalkyl such as cyclopropylmethyl; $C_1$-$C_6$ hydroxyalkyl such as hydroxyethyl; $CH_2CN$; $CH_2C(O)NH_2$; $C_1$-$C_6$ aryl-alkyl such as benzyl and 4-chlorobenzyl; and C1-C5 alkyl-heterocycloalkyl such as tetrahydropyran-4-yl-methyl and 2-morpholin-4-yl-ethyl; and wherein R7-R11 are selected from the group consisting of H; $C_1$-$C_6$ alkoxy such as methoxy; and halogen such as chlorine or fluorine;

wherein further L is a linker selected from the group consisting of —S—$CH_2$—, —$CH_2$—S—, and —$CH_2$—$CH_2$—; and wherein Y is selected from the group consisting of CH, N or C—CN.

In some embodiments, the compound represented by the above formula is 5-(1H-benzoimidazol-2-ylmethylsulfanyl)-2-methyl-[1,2,4]triazolo[1,5-C]quinazoline. These compounds and methods of making them are disclosed in WO 2013/034758. Other compounds represented by the above formula are listed in pages 9-12 of the '758 Publication.

In some embodiments, the PDE10A inhibitor represented by the above formula is 2-{(9-bromo-2-methyl-[1,2,4]triazolo[1,5-c]quinazolin-5-yl)thio1acetonitrile, as described in Kehler, et al., Bioorganic & Medicinal Chemistry Letters 21:3738-3742 (2011) (e.g., compound 33 therein). Other structurally related PDE10A inhibitors that may be useful in the practice of the present invention are disclosed in WO 2012/007006 A1 and WO 2013/034758 A1, both in the name of H. Lundbeck A/S.

In some embodiments, the PDE10A inhibitor is {2-(6-chloropyridin-3-yl)-4-(2-methoxyethoxy)-7,8-dihydropyrido[4,3-d]pyrimidin-6(5H)-yl)(1-neio-1H-imidazol-4-yl)}methanone. This compound is disclosed in Raheem, et al., Bioorg. Med. Chem. Lett. 22:5903-8 (2012) (compound no. 5 therein). Structurally related PDE10A inhibitors that may be useful in the practice of the present invention are disclosed in WO 2010/138430 A1 and WO 2011/022213 A1 (both in the name of Merck, Sharp & Dohme).

In some embodiments, the PDE10A inhibitor is 8,9-dimethoxy-1-(pyridin-3-yl)-5,6-dihydroimidazo[5,1-a]isoquinoline. This compound is disclosed in WO 2011/008597 A1 (compound I-M), and in Ho, et al., Bioorg. Med. Chem. Lett. 22:2585-9 (2012) (compound no. 35). The '597 Publication as well as WO 2010/062559 (both in the names of Schering Plough and Organon) teach structurally related PDE10A inhibitors that may be useful in the practice of the present invention.

Yet other PDE10A inhibitors that may be suitable for use in the present invention are known in the art. See, e.g., U.S. Pat. Nos. 6,936,609; 7,550,465; 7,576,080; 7,786,139; ,7,825,254; 7,846,942; 7,875,618; 8,017,604; 8,053,438; 8,071,595; 8,133,897; 8,178,538; 8,247,418; 8,263,584; 8,263,648; 8,278,327; 8,283,471; 8,318,718; 8,329,700; 8,338,420; 8,343,970; 8,343,973; 8,349,824; 8,349,830; 8,404,710; 8,410,117; and 8,435,995.

All possible tautomeric forms of the PDE10A inhibitors may be used. The diastereomer mixtures can be separated into the individual isomers by chromatographic processes. The racemates can be resolved into the respective enantiomers either by chromatographic processes on chiral phases or by resolution.

The PDE10A inhibitors of the present invention may be formulated and administered in the form of a pharmaceutically acceptable salt, which according to the invention, includes non-toxic salts which in general are accessible by reaction of the PDE10A inhibitors with an inorganic or organic base or acid conventionally used for this purpose. Representative examples of pharmaceutically acceptable salts include the alkali metal salts, e.g., lithium, potassium and sodium salts, the alkaline earth metal salts such as the magnesium and calcium salts, the quaternary ammonium salts such as, for example, the triethyl ammonium salts, acetates, benzene sulphonates, benzoates, dicarbonates, disulphates, ditartrates, borates, bromides, carbonates, chlorides, citrates, dihydrochlorides, fumarates, gluconates, glutamates, hexyl resorcinates, hydrobromides, hydrochlorides, hydroxynaphthoates, iodides, isothionates, lactates, laurates, malates, maleates, mandelates, mesylates, methylbromides, methylnitrates, methylsulphates, nitrates, oleates, oxalates, palmitates, pantothenates, phosphates, diphosphates, polygalacturonates, salicylates, stearates, sulphates, succinates, tartrates, tosylates, valerates, and other salts used for medicinal purposes, as well as solvates and prodrugs of the inhibitors as is well known in the art. Thus, for purposes of the present invention, the PDE10A inhibitor is meant to embrace and include the individual enantiomers or diastereomers and the corresponding racemates and diastereomer mixtures, and salts, solvates and prodrugs of the active pharmaceutical ingredient (API).

The invention further provides a pharmaceutical composition comprising a PDE10A inhibitor, and a pharmaceutically acceptable vehicle, e.g., inert solids, sterile, aqueous solutions, various organic solvents, propellants and gases. The composition may be formulated for any medically acceptable and efficacious route of administration, including oral, parenteral (e.g., intravenous, intraperitoneal, infusion, intraarterial, intramuscular, subcutaneous), topical (which includes transmucosal and transdermal), and pulmonary administration (intranasal and inhalation). The pharmaceutical composition of the invention may be formulated in a variety of ways, including for example, liquid, semi-solid and solid dosage forms, such as liquid solutions (e.g., injectable and infusible solutions), solutions, syrups, elixirs, dispersions or suspensions, emulsions, tablets, pills, capsules, lozenges, powders (including sterile powders that are reconstituted immediately before use), and suppositories. The composition may be formulated as an immediate, controlled, extended or delayed release composition.

Representative examples of solid pharmaceutically acceptable vehicles e.g., for oral delivery, include binding agents (e.g., pregelatinized maize starch, polyvinylpyrrolidone and hydroxypropyl methylcellulose); fillers (e.g., lactose, microcrystalline cellulose and calcium phosphate); lubricants (e.g., magnesium stearate, talc and silica); and disintegrants (e.g., potato starch, croscarmellose, and sodium starch glycolate).

Preparations for parenteral, oral and other modes of administration may include liquid vehicles such as sterile aqueous or non-aqueous solutions, suspensions, and emulsions. Examples of non-aqueous solvents are ethyl alcohol, propylene glycol, glycerol, sorbitol, mannitol, polyethylene glycol, vegetable oils such as peanut oil, cotton seed oil, safflower oil, sesame oil, corn oil, almond oil, olive oil, and injectable organic esters such as ethyl oleate and ethyl laurate. Aqueous vehicles include water, alcoholic/aqueous solutions, emulsions, suspensions, including saline and buffered media (e.g., including phosphate, citrate or other organic salts), e.g., 0.01-0.1 M and preferably 0.05 M phosphate buffer or 0.8% saline. Other common parenteral vehicles include sodium phosphate solutions, pyrogen-free water, Ringer's dextrose, dextrose and sodium chloride, lactated Ringer's, and fixed oils. Examples of emulsifying agents include lecithin and acacia. Examples of suspending agents include sorbitol sryup, methyl cellulose hydrogenated edible fats, microcrystalline cellulose, and ethoxylated isostearyl alcohols.

Pharmaceutically acceptable vehicles may further include isotonic agents such as sugars and sodium chloride; antioxidants including ascorbic acid and methionine; preservatives (e.g., sorbic acid, methyl and propyl p-hydroxy methylbenzoates, octadecyldimethylbenzyl ammonium chloride, hexamethonium chloride, benzalkonium chloride, benzethonium chloride, phenol, butyl or benzyl alcohol, alkyl parabens such as methyl or propyl paraben, catechol, resorcinol, cyclohexanol, 3-pentanol, and m-cresol); low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosacchandes, disaccharides, glucose, mannose, or dextrins; chelating agents such as citric acid and EDTA; sugars such as sucrose, mannitol, trehalose or sorbitol; wetting agents (e.g., sodium lauryl sulfate) salt-forming counter-ions such as sodium; absorption-delaying agents such as aluminum monostearate and gelatin; metal complexes (e.g., Zn-protein complexes); and non-ionic surfactants such as TWEEN or polyethylene glycol (PEG). Compositions may also contain coloring agents, sweetening agents, flavoring agents, perfuming agents, etc.

The pharmaceutical composition can be formulated in a unit dosage form, e.g., in ampules or multi-dose containers. Such formulations include tablets, pills, lozenges, capsules, powders, granules, solutions or suspensions in water or non-aqueous media, or suppositories for oral, parenteral, or rectal administration, or for administration by inhalation. In solid compositions such as tablets the PDE10A inhibitor is mixed with a solid vehicle e.g., corn starch, lactose, sucrose, sorbitol, talc, stearic acid, magnesium stearate, dicalcium phosphate or gums, optionally with a liquid vehicle (e.g., water) to form a solid preformulation composition. The solid preformulation composition is then subdivided into unit dosage forms of the type described above. Tables are typically made by compression or molding. Compressed tablets may be prepared using a binder, lubricant, diluent, preservative, disintegrant and surface-active or dispersing agent. Molded tablets may be made by molding in a suitable machine a mixture of the PDE10A inhibitor moistened with an inert liquid diluent. The tablets, pills, etc., can be coated or otherwise compounded to provide a dosage form affording the advantage of prolonged action. For example, the tablet or pill may include an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials including a number of polymeric acids and mixtures of polymeric acids with such materials as shellac, cetyl alcohol and cellulose acetate. The PDE10A inhibitor may also be micro-encapsulated.

Suitable examples of sustained-release preparations include semipermeable matrices of solid hydrophobic polymers containing the PDE10A inhibitor, which matrices are in the form of shaped articles (e.g., films, or microcapsules). Examples of sustained release matrices include polyesters, hydrogels such as poly(2-hydroxyethyl-methacrylate) or poly(vinylalcohol), polylactides (U.S. Pat. No. 3,773,919), copolymers of L-glutamic acid and 7-ethyl-L-glutamate, non-degradable ethylene vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

Sterile injectable solutions can be prepared by incorporating the PDE10A inhibitor and the vehicle, in the required amount followed by filtered sterilization. Generally, dispersions are prepared by incorporating the PDE10A inhibitor into a sterile vehicle including a basic dispersion medium. In the case of sterile powders for the preparation of sterile injectable solutions, one method of preparation is vacuum drying and freeze-drying, which yields a powder of the antibody from a previously sterile-filtered solution thereof. The preparations for injections are processed, filled into containers such as ampoules, bags, bottles, syringes or vials, and sealed under aseptic conditions according to methods known in the art.

The PDE10A inhibitor may also be formulated in rectal compositions such as suppositories or retention enemas, e.g., containing conventional suppository bases such as cocoa butter or other glycerides.

For intranasal administration or administration by inhalation, the PDE10A inhibitor may be delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, e.g., from gelatin) for use in an inhaler or insulator may be formulated containing a powder mix of a compound of the invention and a suitable powder base such as lactose or starch.

Further, the preparations may be packaged and sold in the form of a kit. Such articles of manufacture may also have labels or package inserts indicating that the associated compositions are useful for therapeutic purposes.

The invention further provides methods of treating cancer or a pre-cancerous condition. The methods entail administering to a subject in need thereof a therapeutically effective amount of a PDE10A inhibitor of the invention. As used herein, the term "subject" refers to any animal (e.g., a mammal), including, but not limited to humans, non-human primates, domestic animals, pets), and the like, which is to be the recipient of a particular treatment or protocol described herein. Typically, the terms "subject" and "patient" are used interchangeably herein in reference to a human subject.

As used herein, the terms "treat" and "treatment" refer to therapeutic treatment, wherein the object is to prevent or slow down (lessen) an undesired physiological change or symptom associated with cancer or a pre-cancerous condition. Beneficial or desired clinical results may include alleviation of symptoms, diminishment of the extent of the disease or condition, stabilization of the disease or condition (i.e., where the disease or condition does not worsen), delay or slowing of onset or the progression of the disease or condition, amelioration or palliation of the disease or pain or discomfort from the condition, and remission (whether partial or total) of the disease or condition, whether detectable or undetectable. "Treatment" can also mean prolonging survival as compared to expected survival if not receiving treatment. Those in need of treatment include those already with the disease or condition as well as those prone to having the disease or condition (e.g., as in the case of subjects with a pre-cancerous condition, family history, genetic predisposition, mutation in an oncogene or tumor suppressor gene, or having elevated PDE10A levels.

As used herein, the term "cancer" refers to or describes diseases in which abnormal cells divide without control and are able to invade other tissues. Cancers to be treated include primary tumors and secondary or metastatic tumors (including those metastasized from lung, breast, or prostate), as well as recurrent or refractory tumors. Recurrent tumors encompass tumors that appear to be inhibited by treatment with such agents, but recur up to five years, sometimes up to ten years or longer after treatment is discontinued. Refractory tumors are tumors that have failed to respond or are resistant to treatment with one or more conventional therapies for the particular tumor type. Refractory tumors include those that are hormone-refractory (e.g., androgen-independent prostate cancer; or hormone-refractory breast cancer, such as breast cancer that is refractory to tamoxifen); those that are refractory to treatment with one or more chemotherapeutic agents; those that are refractory to radiation; and those that are refractory to combinations of chemotherapy and radiation, chemotherapy and hormone therapy, or hormone therapy and radiation.

Therapy may be "first-line", i.e., as an initial treatment in patients who have undergone no prior anti-cancer treatment regimens, either alone or in combination with other treatments; or "second-line", as a treatment in patients who have undergone one prior anti-cancer treatment regimen, either alone or in combination with other treatments; or as "third-line", "fourth-line", etc. treatments, either alone or in combination with other treatments.

Therapy may also be given to patients who have had previous treatments that have only been partially successful but the disease remains intolerant or resistant to the particular treatment. Therapy may also be given as an adjuvant treatment, i.e., to prevent reoccurrence of cancer in patients with no currently detectable disease or after surgical removal of tumor.

Types of cancers to be treated with the PDE10A inhibitors of the invention include carcinomas, blastomas, and sarcomas, tumors, and hematological malignancies. Adult tumors/cancers and pediatric tumors/cancers are included. The cancers may be vascularized, or not yet substantially vascularized, or non-vascularized tumors. The cancers may be characterized by non-solid tumors (e.g., hematopoietic cancers such as such as leukemias (e.g., ALL, AML, CLL, and CML) and lymphomas (Hodgkins and non-Hodgkins, including B-cell and T-cell NHL) or solid tumors.

Examples of cancers characterized by solid tumors which may be treated include breast (including HER2+ and metastatic), colorectal (colon and rectal), pancreatic, prostate, gastrointestinal (e.g., gastric or stomach), throat cancer, esophageal (e.g., squamous cell cancer), bile duct, lung (including small cell and non-small cell lung tumors, adenocarcinoma of the lung and squamous carcinoma of the lung), liver, epidermoid carcinomas, head and neck cancers, epithelial carcinomas, testicular cancer, thyroid (papillary, follicular, medullary and anaplastic), vaginal, cervical, ovarian, neuroendocrine tumors, cancer of the peritoneum, bladder cancer, uterine cancer (e.g., endometrial cancer)urethral cancer, salivary gland cancer, bone cancer (e.g., Ewing's sarcoma and osteosarcoma), soft tissue sarcoma, gallbladder carcinoma, myeloma, vulval cancer, penile carcinoma, androgen-dependent tumors (e.g., early prostate cancer), androgen-independent tumors (e.g., advanced prostate cancer), Kaposi's sarcoma, synovial sarcoma, CNS metastasis, hemangiosarcomas, brain cancer (e.g., glioblastomas, meningiomas, ependymoma, cerebral metastases, and medulloblastoma), skin cancer (e.g., basal cell carcinoma, squamous cell carcinoma, and melanoma), rhabdomyosarcoma, Wilm's cancer, rhabdomyosarcoma, retinoblastoma, adrenal cancer, (e.g., adrenal cortical cancer and pheochromocytoma), and leiomyosarcoma.

The invention also provides methods of treating subjects who are at risk or predisposed to cancer. These subjects have pre-cancerous conditions which are known in the art as a group of disorders that have a malignant predisposition. Representative examples of pre-cancerous conditions of the colon that may be treated in accordance with the present invention include adenomas/polyps in subjects with familial adenomatous polyposis (Gardner's syndrome), sporadic adenomatous polyposis, or precancerous conditions associated with hereditary non-polyposis colon cancer (Lynch syndrome), inflammatory bowel disease, or Chrohn's disease. Examples of precancerous conditions of other tissues include cervical dysplasia or squamous intraepithelial lesion (e.g., diagnosed by pap smear), prostatic intraepithelial neoplasia (PIN); superficial bladder cancer, also known as transitional cell carcinoma in situ, precancerous lesions of the breast, precancerous lesions of the lung, actinic keratosis, Barrett's esophagus; precancerous melanoma moles, precancerous conditions of the uterus/vulva, precancerous conditions of the ovary, atrophic gastritis, precancerous conditions of the oral cavity, general dysplastic conditions, squamous metaplasia, intraepithelial neoplasia, and precancerous conditions in the head or neck. Subjects having such a condition may also exhibit abnormally high PDE10A mRNA or protein expression in the respective tissue relative to normal appearing tissues.

The PDE10A inhibitor may be administered only once but more typically may be administered over a series of treatments lasting from several days, months or years until cure, remission, or a diminution in disease state (e.g., reduction in tumor size). For multiple dosages, the PDE10A inhibitor may be, for example, administered three times a day, twice a day, once a day, once every two days, twice a week, weekly, once every two weeks, or monthly.

The PDE10A inhibitors of the invention are administered in a "therapeutically effective amount". A "therapeutically effective amount" refers to an amount effective, at dosages and for periods of time necessary, to "treat" the cancer as that term is used herein. For example, the therapeutically effective amount of the drug can reduce the number of cancer cells, reduce the tumor size; inhibit or stop cancer cell infiltration into peripheral organs including, for example, the spread of cancer into soft tissue and bone, inhibit and stop tumor metastasis, inhibit and stop tumor growth, relieve or reduce one or more of the symptoms associated with the cancer, reduce morbidity and mortality, improve quality of life, or a combination thereof. A therapeutically effective amount of the PDE10A inhibitor may vary according to factors such as the disease state, age, sex, and weight and overall health of the individual, any previous treatment, patient's clinical history, and the ability of the PDE10A inhibitor to elicit a desired response in the subject. A therapeutically effective amount is also one in which any toxic or detrimental effects of the PDE10A inhibitor are outweighed by the therapeutically beneficial effects.

In some embodiments of the present invention, the PDE10A inhibitor may be used to treat subjects who are not diagnosed with colon cancer, but who are pre-disposed to the disease as determined by having elevated PDE10A mRNA level in apparently normal colon mucosa. Subjects who are amenable to such treatment fall into two categories, namely subjects whose APC (i.e., adenomatous polyposis coli) gene is mutated and who otherwise do not show any other precancerous condition (e.g., they do not have adenomas or polyps), and subjects who do exhibit precancerous legions. This may include patients with HNPCC who typically do not present with polyps as do patients with APC mutations. In these embodiments, a "therapeutically effective amount" of the PDE10A inhibitor may inhibit (or even prevent) progression of the condition into colon cancer, and refers to an amount effective, at dosages and for periods of time necessary, to achieve the desired result. Typically, since this dose is used in subjects prior to or at an earlier stage of disease, the actual dosage amount might be less than the therapeutically effective amount administered to a cancer patient. Such treatments would reduce the number of polyps that otherwise need to be removed by colonoscopy, which is associated with significant discomfort and even death.

A therapeutically or prophylactically effective amount of a PDE10A inhibitor of the invention may vary from about 0.001 mg to about 2000 mgs, and in some embodiments from about 10 to about 1,000 mg per day.

The methods of treatment described herein can be used to treat any subject in need thereof, e.g., mammals, including primates, such as monkeys and humans, horses, cows, cats, dogs, or other livestock or pets. In another embodiment, the treatment can be used for laboratory rodents such as rats and mice or cultured cancer cells in vitro or vivo for the screening or testing of PDE10A inhibitors for cancer. In one embodiment, the mammal to be treated is human.

More than one PDE10A inhibitor may be administered, either incorporated into the same composition or administered as separate compositions.

The PDE10A inhibitor may be administered alone (monotherapy), or in combination with one or more therapeutically effective active agents (e.g., anti-cancer agents) or treatments (combination therapy) or chemopreventive agent (e.g., NSAID or COX-2 inhibitor).

For instance, in some embodiments, the PDE10A inhibitor is co-administered with a PDE5 inhibitor to improve efficacy or reduce the effective dose range of the PDE10A inhibitory. Representative examples of PDE5 inhibitors that may be useful in the practice of the present invention include sildenafil, tadalafil, vardenafil, udenafil, and avanafil or others such as MY5445 or compounds that increase intracellular cGMP levels (e.g., nitric oxide donors or releasing drugs). Examples of yet other PDE5 inhibitors that may be suitable for use in the practice of the present invention are disclosed in WO 1994/028902, WO 1996/016644, and WO 2001/019802. Also included are peptides and hormones that can activate guanylyl cyclases such as uroguanylin and naturetic peptides as well as related peptides.

Other anti-cancer therapeutically effective agents/treatments include surgery, radiation chemotherapeutic agents, cytokines, chemokines and biological agents such as antibodies to other targets, and various molecular targeted drugs such as EGFR or other kinase inhibitors, or other, such as proteasomal inhibitors.

The anti-neoplastic agent also includes radiation. When the anti-neoplastic agent is radiation, the source of the radiation can be either external (external beam radiation therapy—EBRT) or internal (brachytherapy—BT) to the patient being treated. The dose of anti-neoplastic agent administered depends on numerous factors, including, for example, the type of agent, the type and severity of tumor being treated and the route of administration of the agent. It should be emphasized, however, that the present invention is not limited to any particular dose. Radiation may also be used in conjunction with other anti-neoplastic agents.

Examples of chemotherapeutic agents (which are typically small molecules) include topoisomerase inhibitors (e.g., inhibitors of topoisomerase I or topoisomerase II. Topoisomerase I inhibitors such as irinotecan (CPT-II), aminocamptothecin, camptothecin, DX-8951f, topotecan. Topoisomerase II inhibitors include etoposide (VP-16), and teniposide (VM-26)), cyclophosphamide, thiotepa, bysulfan, melphalan, dacarbazine, cytosine arabinoside, cyclophosphamide, actinomycin-D, methotrexate, gemcitabine, oxyplatin, fluorouracil (5-FU), leucourin (LU), cisplatin, irinotecan (CPT-II), paclitaxel, docetaxel, vinblastine, epothilone, carboplatin, pegylated adriamycin, anthracyclines (e.g., daunomycin and doxorubicin), vindesine, neocarzinostatin, cis-platinum, chlorambucil, cytosine arabinoside, 5-fluorouridine, and calicheamicin.

A chemotherapeutic agent may be administered as a prodrug. The term "prodrug" refers to a precursor or derivative form of a pharmaceutically active substance that is less cytotoxic to tumor cells compared to the parent drug and is capable of being enzymatically activated or converted into the more active parent form. Examples of prodrugs include phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug.

"Cytokines" refer to proteins and derivatives thereof released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -δ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; IL-15, tumor necrosis factor such as TNF-α and TNF-β; and other polypeptide factors including LIF and kit ligand (KL).

Chemokines include MIP-1α, MIP-1β, RANTES, SDF-1, MCP-1, MCP-2, MCP-3, MCP-4, eotaxin, eotaxin-2, I-309/TCA3, ATAC, HCC-1, HCC-2, HCC-3, LARC/MIP-3α, PARC, TARC, CKβ, CKβ6, CKβ7, CKβ8, CKβ9, CKβ11, CKβ12, C10, IL-8, GROα, GROβ, ENA-78, GCP-2, PBP/CTAβIIIβ-TG/NAP-2, Mig, PBSF/SDF-1, and lymphotactin.

Therapeutic antibodies may be useful, including antibodies specific to TrkB, TrkC, CD19, CD20, CD33, CD44, CD45, CD46, CD59, EGFR, EGF, VEGF, VEGFR-1, VEGFR-2, VEGFR-3, PDGFR, PDGF, IGFR, IGF, NGFR, NGF, FGFR, FGF, RON, gp75, Flt-3, Fas, AFP, PDFG, CA 125, CEA, T cell receptor α/β, $GD_2$. $GD_3$, GM1, GM2, Her-2/Neu, Ep-CAM (KSA), endothelin receptor, IL-2 receptor, Lewis-Y, Lewis-X (CD 15), melanoma-associated proteoglycan MCSP, PSA, cadherin, and the transferrin receptor.

For example, an antibody against EGFR, such as Erbitux® (cetuximab), may also be administered, particularly when treating colon or head and neck cancer. Other antibodies for combination use include Herceptin (trastuzumab) (an antibody the inhibits the growth of breast cancer cells that express HER2) and Avastin® (bevacizumab) (an antibody that inhibits angiogenesis). Other anti-cancer antibodies specifically bind human insulin-like growth factor-1 (IGFR). See, e.g., WO 2005/016970 and U.S. Pat. No. 7,241,444.

Enzymatically active toxins or fragments thereof that may be useful as a conjugate to PDE10 inhibitors or administered in combination include diphtheria A chain, nonbinding active fragments of diphtheria toxin, exotoxin A chain (from *Pseudomonas aeruginosa*), ricin A chain, abrin A chain, modeccin A chain, α-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes.

Representative examples of other therapeutic agents (which are not necessarily anti-cancer agents) include antibiotics that target gram-negative bacteria, including broad spectrum antimicrobials that cover both gram-positive and gram-negative organisms, including quinolones (e.g., Baytril, ciprofloxacin), cephalosporins (e.g., cefepime, ceftazidine) and aminoglycosides (e.g., gentamicin, amikacin).

The administration of the PDE10A inhibitors with other agents and/or treatments (which may be referred to herein as "co-administration") may occur simultaneously, or separately, via the same or different route, at the same or different times. Dosage regimens may be adjusted to provide the optimum desired response.

The present invention further provides a method for screening or identifying subjects at risk of or predisposed to a precancerous condition or cancer. The method may be semi-quantitative or quantitative and entails measuring the amount of PDE10A protein or PDE10A messenger RNA (mRNA) in a tissue sample or biopsy obtained from a subject, relative to a control (i.e., the amount of PDE10A mRNA or protein from a normal tissue sample obtained from a statistically significant group of subjects that do not have the relevant oncogene (e.g., APC, BRCA1, or BRCA2 genes), wherein an elevated amount of PDE10A or PDE10A mRNA relative to the control is indicative of a predisposition to a precancerous condition or cancer.

Tissue samples or biopsies may be obtained in accordance with standard medical procedures (e.g., bone marrow biopsy, endoscopic, needle, skin, surgical, etc.). For example, colon biopsies may be routinely obtained during the course of a colonoscopy. The sample may be lysated or homogenized for purposes of detecting or quantifying the PDE10A or PDE10A mRNA. Bodily fluids such as blood (and serum or plasma) and urine which contain circulating or excreted amounts of cyclic nucleotides (cAMP or cGMP) that are indicative of PDE10A activity may also be considered as tissue samples for purposes of the present invention.

Methods for detecting PDE10A protein levels in tissue samples can be performed based on known techniques including, for example, immunoassays. Certain preferred immunoassays are enzyme linked immunoadsorbent assays (ELISAs) and radioimmunoassays (RIA). Antibodies (e.g., monoclonal antibodies) that specifically bind PDE10A are known in the art. Alternatively, they can be made using standard techniques. Contacting the chosen biological sample with the antibody under conditions effective and for a period of time sufficient to allow the formation of immune complexes primary immune complexes) is generally a matter of adding the antibody composition to the sample and incubating the mixture for a period of time long enough for the antibodies to form immune complexes with, i.e., to bind to, PDE10A. The sample-antibody composition may be washed to remove any non-specifically bound antibody species, allowing only those antibodies specifically bound within the primary immune complexes to be detected. In general, the detection of immunocomplex formation is well known and may be achieved through the application of numerous approaches. These methods are based upon the detection of a detectable label such as a radioactive, fluorescent, chemiluminescent or chromogenic tag. The PDE10A antibody used in the detection may itself be conjugated to a detectable label, wherein one would then simply detect this label. The amount of the primary immune complexes in the composition would thereby be determined.

Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are washed to remove any non-specifically bound labeled secondary antibodies or ligands, and the remaining label in the secondary immune complex is detected.

An enzyme linked immunoadsorbent assay (ELISA) is a type of binding assay. In one type of ELISA, the PDE10A antibodies are immobilized onto a selected surface exhibiting protein affinity, such as a well in a polystyrene microtiter plate. Then, a tissue sample is added to the wells. After binding and washing to remove non-specifically bound immune complexes, the bound PDE10A may be detected. Detection is generally achieved by the addition of another anti-PDE10A antibody that is linked to a detectable label. This type of ELISA is a simple "sandwich ELISA." Detection may also be achieved by the addition of a second anti-PDE10A antibody, followed by the addition of a third antibody that has binding affinity for the second antibody, with the third antibody being linked to a detectable label.

In another type of ELISA, the tissue samples are immobilized onto the well surface and then contacted with the PDE10A antibodies. After binding and washing to remove non-specifically bound immune complexes, the bound PDE10A antibodies are detected. Where the initial PDE10A antibodies are linked to a detectable label, the immune complexes may be detected directly. Alternatively, the immune complexes may be detected using a second antibody that has binding affinity for the PDE10A antibody, with the second antibody being linked to a detectable label.

Irrespective of the format employed, ELISAs have certain features in common, such as coating, incubating or binding, washing to remove non-specifically bound species, and detecting the bound immune complexes.

The radioimmunoassay (RIA) is an analytical technique which depends on the competition (affinity) of an antigen for antigen-binding sites on antibody molecules. Standard curves are constructed from data gathered from a series of samples each containing the same known concentration of labeled antigen, and various, but known, concentrations of unlabeled antigen. Antigens are labeled with a radioactive isotope tracer. The mixture is incubated in contact with an antibody. Then the free antigen is separated from the antibody and the antigen bound thereto. Then, by use of a suitable detector, such as a gamma or beta radiation detector, the percent of either the bound or free labeled antigen or both is determined. This procedure is repeated for a number of samples containing various know concentrations of unlabeled antigens and the results are plotted as a standard graph. The percent of bound tracer antigens is plotted as a function of the antigen concentration. Typically, as the total antigen concentration increases the relative amount of the tracer antigen bound to the antibody decreases. After the standard graph is prepared, it is thereafter used to determine the concentration of antigen in samples undergoing analysis.

In an analysis, the sample in which the concentration of antigen is to be determined is mixed with a known amount of tracer antigen. Tracer antigen is the same antigen known to be in the sample but which has been labeled with a suitable radioactive isotope. The sample with tracer is then incubated in contact with the antibody. Then it can be counted in a suitable detector that measures the free antigen remaining in the sample. The antigen bound to the antibody or immunoabsorbent may also be similarly counted. Then, from the standard curve, the concentration of antigen in the original sample is determined.

Aside from immunassays, immunohistochemical detection using tissue sections is also particularly useful. However, it will be readily appreciated that detection is not limited to such techniques, and Western blotting, dot and slot blotting, FACS analyses, and the like may also be used.

In other embodiments, the method entails detecting or quantifying PDE10A mRNA in a tissue sample using hybridization techniques such as slot and northern blots or in amplification techniques such as reverse transcriptase polymerase chain reaction (RT-PCR). The presence of elevated levels of PDE10A mRNA in a tissue relative to normal tissue can indicate that the subject is predisposed to precancer or cancer. The RNA isolated from a tissue sample can be further fractionated to isolate mRNA by selecting for poly-adenylated RNA (poly-A RNA). Then the mRNA can be converted into complementary DNA (cDNA) suitable for PCR.

Briefly, in PCR, two oligonucleotide primers are synthesized whose sequences are complementary to sequences that are on opposite strands of the template DNA and flank the segment of DNA that is to be amplified. The template DNA is denatured by heating in the presence of an excess of the two primers, the four deoxynucleotide triphosphates, and magnesium. As the reaction is cooled, the primers anneal to their target sequences. Then the annealed primers are extended with DNA polymerase. The initial round can potentially double the product and each successive round of amplification can potentially lead to a logarithmic increase in amount of the amplification product because the product of one round can serve as template in the next round. Multiple rounds of amplification (denaturation, annealing, and DNA synthesis) are conducted until a sufficient amount of amplification product is produced. Finally, the amplification product is detected, usually by visual means or indirectly through chemiluminescence, or detection of a radioactive label or fluorescent label, or the like.

There are a number of template-dependent amplification processes, e.g., PCR, which is described in detail in U.S. Pat. Nos. 4,683,195, 4,683,202, and 4,800,159. The thermostable Taq DNA polymerase is most commonly used in the PCR process because it remains active at the high temperatures used in the amplification process. Reverse transcriptase PCR (RT-PCR) can be used to estimate semiquantitative levels of mRNA of PDE isozyme family members in neoplastic tissue samples. Methods of reverse transcribing RNA into cDNA are well known and are described in Sambrook, et al., 1989.

The amounts of the PDE10A protein or the PDE10A mRNA are compared to a control or normal appearing tissue, which may be prepared from a statistically significant number of normal subjects (who also may be known to lack activating mutations in oncogenes or disabling mutations in tumor suppressor genes. Amounts of PDE10A protein or PDE10A mRNA that are elevated relative to a control may be indicative of a predisposition to precancer or cancer.

In view of the teachings herein indicating that PDE10 has limited expression in peripheral tissues, but is elevated in early and late stage tumors where it may provide not only a therapeutic advantage for inhibitors, but also a marker of disease to aid in diagnosis or prognosis, PDE10 inhibitors may be used as a diagnostic aid in methods to detect the onset of (e.g., early stage) disease or staging. Accordingly, another aspect of the present invention is directed to a method for detecting cancer or the stage of the disease (such as micro-metastasis or metastasis). The methods entail administration of a radiolabeled PDE10 inhibitor to a patient who has been diagnosed with cancer or to a patient who is suspected of having cancer. Representative radiolabels include radioisotopes (e.g., $^{18}F$, $^{11}C$, $^{13}N$, $^{15}O$). An effective amount of the radiolabel for cancer diagnostic purposes (as the term cancer is described herein) will range generally from about 100 to about 500 microCi. Thus, the PDE10 inhibitor, labeled with a radioisotope, may be used as a radiopharmaceutical for positron emission tomography (PET) imaging to detect early stage disease or micro-metastasis. These studies may be complemented with other analysis of PDE10, such as by immunohistochemistry using tissue biopsies or other imaging modalities such as magnetic resonance imaging (MRI). A common imaging test is PET-MRI. These tests typically involve administration (e.g., oral, iv, or subcutaneous) of a diagnostically effective amount of the labeled PDE10 inhibitor to a patient. By way of example, radiolabeled Pf-2545920 can be synthesized by methylation of a N-desmethyl precursor with [$^{11}C$]- methyl iodide (MeI) in the presence of NaH as described in Tu, et al., Bioorg. Med. Chem. 19:1666-73 (2011). [$^{11}C$]Pf-2545920 can be purified by HPLC and identity confirmed by co-eluting with unlabeled drug. The synthesis including the production of [$^{11}C$]MeI, HPLC purification, and formulation of the radiolabel can be completed, typically within 50-55 minutes, to allow for imaging, despite the short half-life of the isotope. A solution of [$^{11}C$]Pf-2545920 (100-150 µCi) can be diluted in saline at a suitable volume and administered to patients immediately prior to PET imaging. In view of the differential expression of PDE10 in cancer, a positive diagnosis may be based on the differential retention or concentration of the radiolabel (which becomes indirectly attached to the PDE10 enzyme as a consequence of binding of the enzyme with the inhibitor) in a particular tissue relative to retention or concentration in surrounding tissue.

The present invention will now be described in terms of the following non-limiting examples.

Materials and Methods
Drugs and Reagents

PDE inhibitors, papaverine, 8-MeoM-IBMX, EHNA, cilostazol, and rolipram were purchased from Sigma-Aldrich. MY5445 was purchased from EMD Millipore. PF-2545920 was purchased from Selleck Chemicals, while other PDE10A inhibitors were synthesized as described herein. Recombinant PDE enzymes were purchased from BPS Biosciences. DMSO was used as the vehicle for testing effects of all compounds.

Cells and Cell Culture

The human colon tumor cell lines, HCT116, HT29, SW480, SW620, colo741, Caco-2, DLD-1, LS174T, and RKO and human breast tumor cell lines, MCF7, T47D, ZR75, MDA-MB-231, HS578T, and MDA-MB-468 were purchased from ATCC and grown under standard cell culture conditions in RPMI 1640 medium containing 5% fetal bovine serum (FBS) at 37° C. in a humidified atmosphere with 5% $CO_2$. All cell lines comprising the NCI-60 cancer cell panel were obtained from the NCI Developmental Therapeutics Program and maintained under the same standard conditions. The human normal colonocyte (NCM460) cell line was purchased from Incell (San Antonio, Tex.) and grown according to the manufacturer's specifications. The human colon adenoma cell line, LT97, was a gift from Dr. Brigitte Marian (Medical University Vienna, Austria) and grown according to the provider's specifications. Human mammary epithelial cells (HMEC) were purchased from Lonzo and grown using culture conditions as recommended by the supplier.

siRNA Transfection

One sequence of siRNA targeting human PDE10A (siPDE10-1) and scrambled control siRNA were purchased from Qiagen. Another sequence of siRNA targeting human PDE10A (siPDE10-2) was purchased from Dharmacon. The siRNA target sequences were as follows: siPDE10-1, 5'-GACCGGATCACTAAACCTTAA-3' (SEQ ID NO:1); siPDE10-2, 5'-GGAGTTATATTCAGACCTT-3' (SEQ ID NO:2). The scrambled control siRNA, contains nonspecific sequences that do not have homology in the human genome. siRNA duplexes were transfected into cells by using RNAiMAX transfection reagent (Life Technologies) according to manufacturer's specifications and incubated at 37° C. for 72 hours.

PDE Enzymatic Assays

PDE enzymatic activity was measured using IMAP fluorescence polarization assay (Molecular Devices. Inc.). The assay was modified as described previously [Tinsley, et al., Mol. Cancer Ther. 8(12):3331-40 (2009)], to use fluorescein-cAMP and tetramethylrhodamine (TAMRA)-cGMP as substrates, allowing for simultaneous measurement of cAMP and cGMP hydrolysis. For experiments involving cell extracts, $2 \times 10^5$ cells per well were plated on a six-well tissue culture plate 72 hours prior to cell lysis.

Growth Assays

Ninety-six (96)-well microtiter plates were seeded at a density of 5,000 cells per well. For drug treatment, cells were treated with compounds or vehicle control, and incubated at 37° C. for 72 hours. For siRNA assays, cells were transfected with siRNA under the same conditions described above. The effect of treatment with inhibitors or siRNA knockdown of PDE10A on growth was measured using the Cell Titer Glo Assay (Promega), which measures viable cell number based on ATP content.

Apoptosis Assay

Ninety-six (96)-well microtiter plates were seeded at a density of 10,000 cells per well. For drug treatment, cells were treated with compounds or vehicle as a control, and incubated at 37° C. for 6 hours. For siRNA knockdown experiments, cells were transfected with siRNA under the same conditions as described above. The induction of apoptosis caused by treatment with PDE10A inhibitors and PDE10A siRNA knockdown was determined using the Caspase 3/7 Glo Assay (Promega), which measures cleavage of a substrate by either caspase-3 or caspase-7.

Proliferation Assay

Cells were plated at a density of $2 \times 10^5$ cells per well in 6-well tissue culture plate and transfected with siRNA. Cells were then incubated at 37° C. for 54 hours prior to the addition of 10 μM EdU. After 18 hours of incubation with EdU, cells were harvested and analyzed using the Click-iT EdU Alexa Fluor 488 Proliferation Assay (Life Technologies) according to the manufacturer's specifications. The percentage of proliferating cells was quantified using a Guava EasyCyte Plus flow cytometer. A minimum of 5,000 events were collected for each treatment group with use of minimal electronic compensation.

Cell Cycle Analysis

Cells were fixed and permeabilized with ice-cold 70% ethanol at 4° C. overnight. After washing with PBS, cells were treated with RNase at 37° C. for 20 minutes, and then stained with propidium iodide (PI) at a concentration of 40 μg/ml. Samples were analyzed by flow cytometry and cell cycle distribution determined with CellQuest software.

Quantitative Real-time PCR

TissueScan™ tissue qPCR arrays (Origene) were used according to the manufacturer's protocol. The panel consisted of cDNA derived from normal colon (n=8) or patients with malignant disease (e.g. adenocarcinoma of the colon) and grouped as: Stage I (n=5), Stage II (n=9), Stage III (n=16), and Stage IV (n=10) based on pathological assessments. The primers used to detect PDE10A and PDE5A were from SABiosciences. Expression levels of β-actin were used to normalize relative PDE5A and PDE10A expression levels in the tissue samples.

Cell Lysis

Cells were lysed and protein concentrations determined as described previously (Tinsley, et al., supra).

Western Blotting

Western blot analysis was performed as described previously (Tinsley, et al., supra). The following antibodies were used to detect specific proteins: PDE2 (GeneTex, 1:1000), PDE3 (Abcam, 1:1000), PDE5 (Cell Signaling, 1:1000), PDE10 (GeneTex, 1:1000), survivin (Cell Signaling, 1:1000), GAPDH (Cell Signaling, 1:5000).

Luciferase Reporter Assay

Cells were plated at a density of $5 \times 10^4$ cells per well in 24-well tissue culture plate and allowed to grow overnight. The cells were then transfected with 0.1 μg TOPFlash construct (Upstate Biotechnology) and 0.1 μg β-galactosidase-expressing vector (Promega). After 24 hours of transfection, cells were treated with compounds or vehicle for 24 hours. For siRNA knockdown experiments, the cells were transfected with siRNA and, after 24 hours, were transfected again with a β-galactosidase-expressing vector as described above, and then incubated for another 48 hours. At the end of treatment, cells were lysed and luciferase and β-galactosidase activities were measured using assay systems from Promega. Luciferase activity was normalized to β-galactosidase activity.

Immunohistochemistry

Paraffin sections of colorectal cancer obtained from patients were prepared using standard procedures. Antigens were processed by incubating with Tris-EDTA buffer (pH9.0) in a scientific pressure cooker for 10 min after deparaffinization. Endogenous peroxidase activity was inactivated in 3% hydrogen peroxide solution for 5 min. After blocking with 3% goat serum for 20 min, sections were incubated with either PDE5A primary antibody or PDE10A primary antibody for 1 hour in a humidity chamber at room temperature. After rinsing with Tris buffer, sections were incubated at room temperature for 1 hour with HRP-conjugated anti-rabbit antibody. Labeling (DAB) reactions were performed following 3 times washes in Tris buffer. Sections were counterstained with hematoxylin for one minute, dehydrated and mounted with permount mounting medium.

Statistic Analysis

Statistical analysis was performed by using Prism5 software (Graphpad). All of the data are expressed as the mean±S.E.M. from at least three separate experiments. Effects of compounds on cell growth and PDE activity were measured and the potency expressed as an $IC_{50}$ value that was also determined using Prism5. Comparisons of data among groups were performed with student's t test. A p value of <0.05 was considered statistically significant.

EXAMPLE 1

PDE10A is Over-expressed in Human Colon Tumor Cells Compared to Normal Colonocytes PDE10A expression was examined in a panel of human colon cell lines and found to be elevated in cells derived from colon adenocarcinomas (HCT116, HT29, Caco2, SW480) and adenomas (LT97) compared with normal colonocytes (NCM460) as shown in FIG. 1 by Western blotting using a PDE10A specific antibody. The band was confirmed to be PDE10 based on a similar molecular weight as recombinant PDE10.

Figure 2:
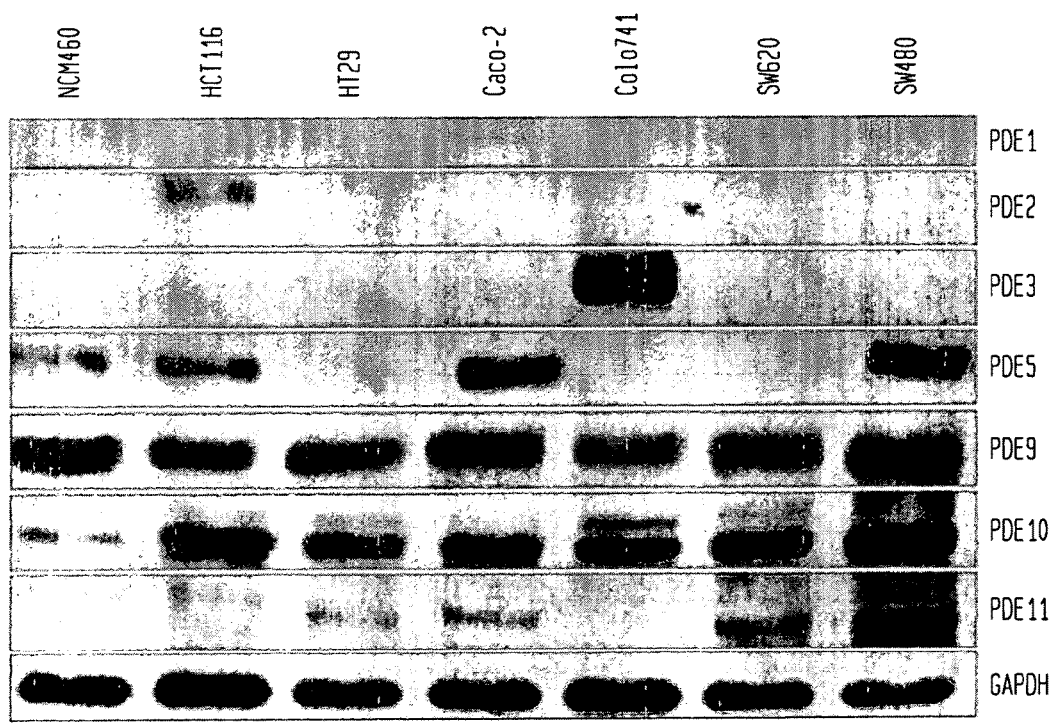
FIG. 2 is a Western blot showing the expression of PDE10 and other cyclic guanosine monophosphate (cGMP) degrading PDE isoenzymes in human colon tumor cells compared with normal human colonocytes (NCM460), wherein PDE isozymes were measured by Western blotting in whole cell lysates using commercially available PDE isozyme specific antibodies and GAPDH was used as a loading control.

The expression of all known cyclic guanosine monophosphate degrading isozymes (with the exception of PDE6 that is commonly known to be restricted to the retina) including PDE1, PDE2, PDE3, PDE5, PDE9, PDE10, and PDE11 were measured in human colon tumor cells and normal colonocytes by Western blotting using isozyme-specific antibodies. As shown in FIG. 2, PDE10A levels were high in all colon tumor cell lines examined compared with normal colonocytes, while all other PDE isozymes were either not expressed or not uniformly elevated in colon tumor cells. These observations point to a unique role of PDE10A in both early and late stages of colon cancer progression and illustrate the use of methods for detection as a tool for disease diagnosis and prognosis.

EXAMPLE 2

PDE10A Expression Increases During Progression of Colorectal Cancer

Figure 3A:
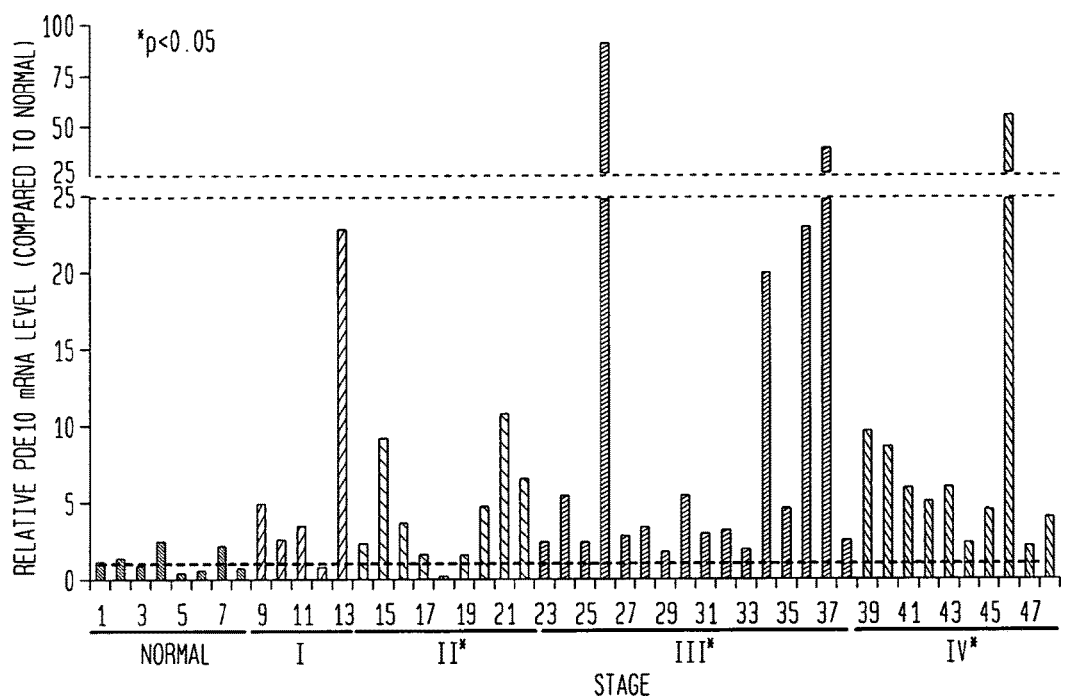
FIGS. 3A-B are graphs showing expression of PDE10A mRNA in samples from clinical specimens of normal colon mucosa or colon adenocarcinomas from various stages of malignant progression, wherein PDE10A mRNA levels were measured in tissue cDNA arrays by real-time PCR (Origene).
Figure 3B:
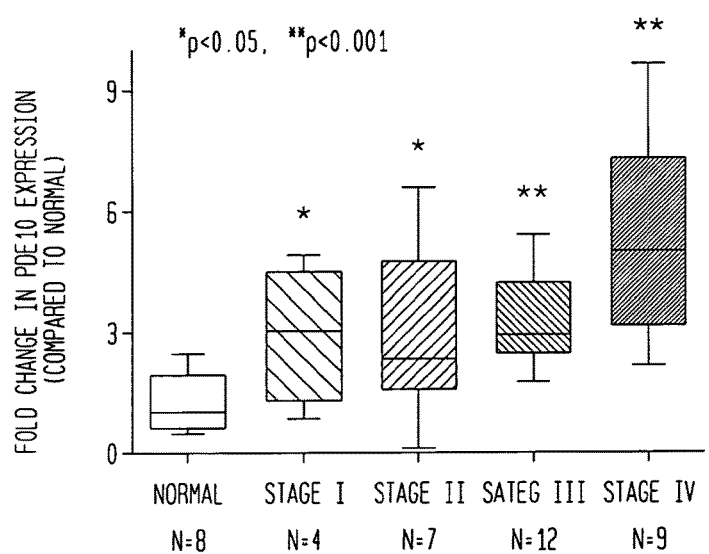

To evaluate the relationship of PDE10A expression to the progression of colorectal cancer using human clinical specimens, PDE10A mRNA levels were measured by quantitative real-time PCR using cDNA arrays obtained from normal human colonic mucosa and from colon adenocarcinomas covering four distinct stages of malignant progression as assessed by standard pathological grading. As shown in FIG. 3A, PDE10A levels were low in normal colonic mucosa but were increased in most disease specimens. As shown in FIG. 3B, PDE10A mRNA levels from each stage were grouped and analyzed in a box-and whisker plot. A statistically significant increase in PDE10A mRNA levels was measured in all adenocarcinoma specimens compared to normal colonic mucosa (p<0.05). These observations provide evidence that PDE10A mRNA levels are elevated in colon tumor cells and patient-derived clinical specimens as compared to normal colonocytes and colonic mucosa and that the relative levels positively correlates with the severity of the disease.

EXAMPLE 3

PDE10A Expression in Adenomas, Adenocarcinomas and Metastatic Liver Lesions

Immunohistochemical analysis of patient specimens (as described in "Material and Methods") demonstrated that PDE10A and PDE5A protein are expressed in adenomas, adenocarcinomas, and metastatic lesions (FIGS. 4A-F). Note that PDE10A levels were low in normal liver and adjacent uninvolved colon tissue. These data provide evidence that PDE10A protein levels are elevated in early lesions and that levels remain elevated throughout late stages of colorectal cancer progression.

EXAMPLE 4

Cancer Diagnosis and Monitoring of Progression of Colon Cancer by Measuring PDE10A mRNA Levels Relative levels of PDE10A and PDE5A expression in mRNA obtained from tissue samples of a murine genetic model of colorectal cancer (APC/Min) were analyzed by quantitative real time PCR as described in "Materials and Methods."

Figure 5A:
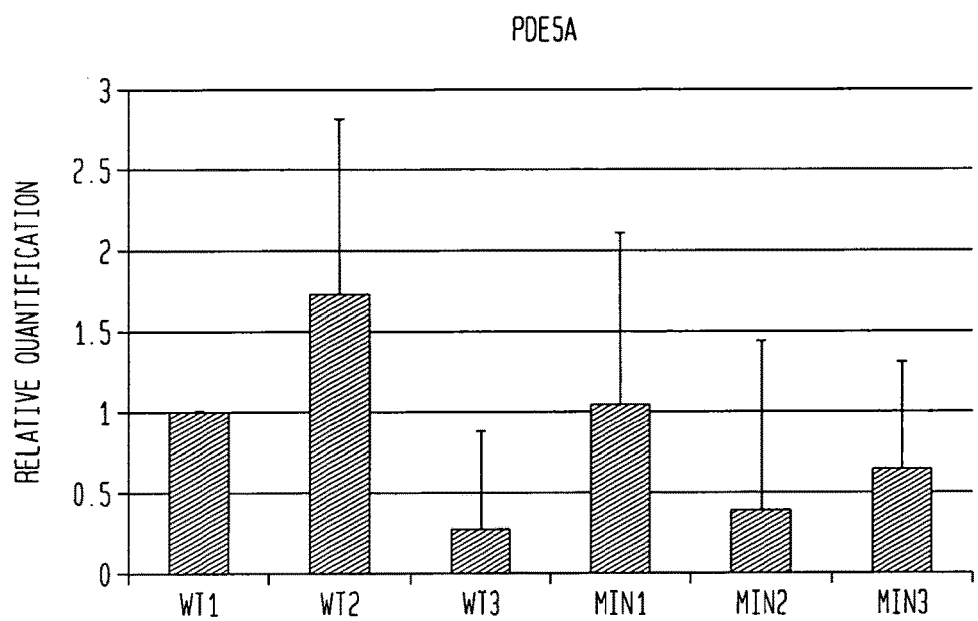
FIGS. 5A-B are graphs of quantitative real time-PCR measurements showing relative PDE5A and PDE10A mRNA expression in normal intestine from wild type mice (WT) compared with intestinal tumors from mice with APC mutations (Min), wherein PDE5A and PDE10A levels were measured in the same sample (by real-time PCR) in which three mice from the WT and MIN groups were analyzed, and which show that PDE10A levels were elevated in tumors compared with normal mucosa, while PDE5A levels were not significantly different.
Figure 5B:
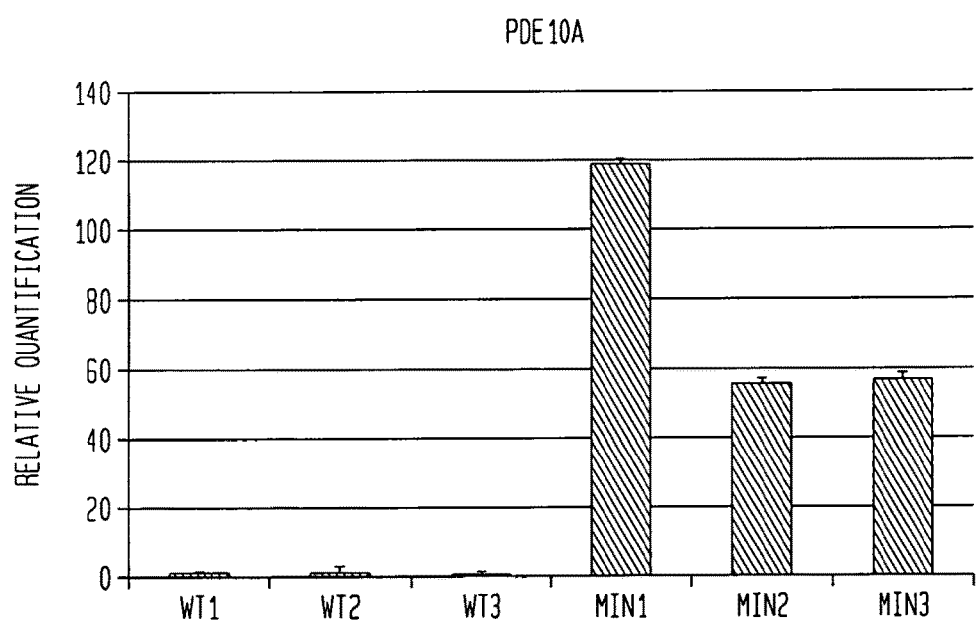
Figure 6:
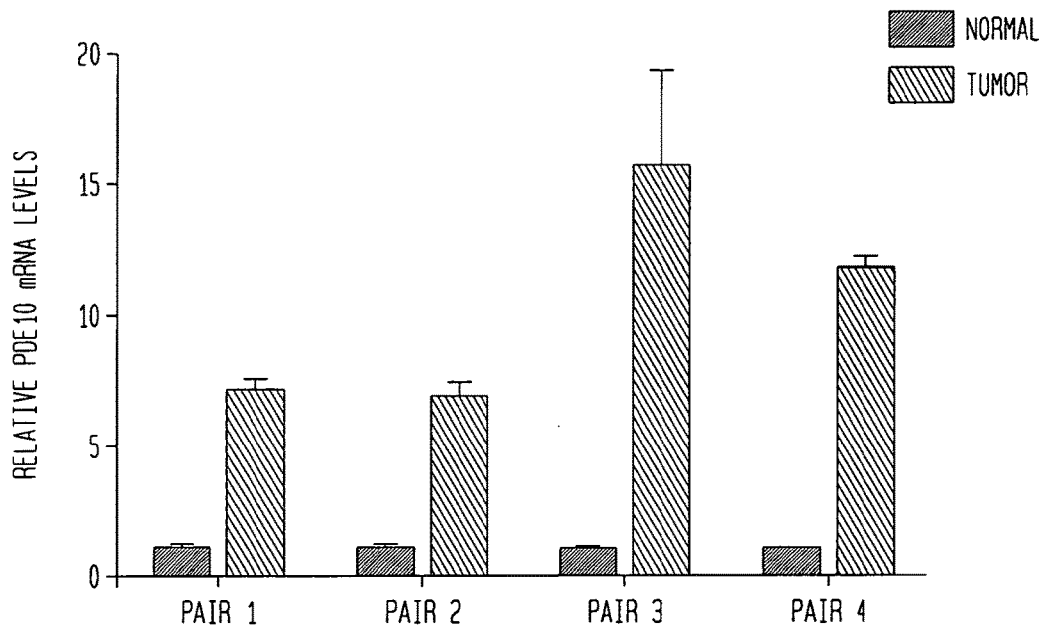
FIG. 6 is a graph showing PDE10A mRNA levels in paired specimens from normal intestine or intestinal tumors obtained from mice with APC mutations (MIN), wherein PDE10 mRNA was measured by real-time PCR, and which show that PDE10A mRNA levels were elevated in tumor specimens compared with normal intestine using samples obtained from the same mouse.
Figure 7:
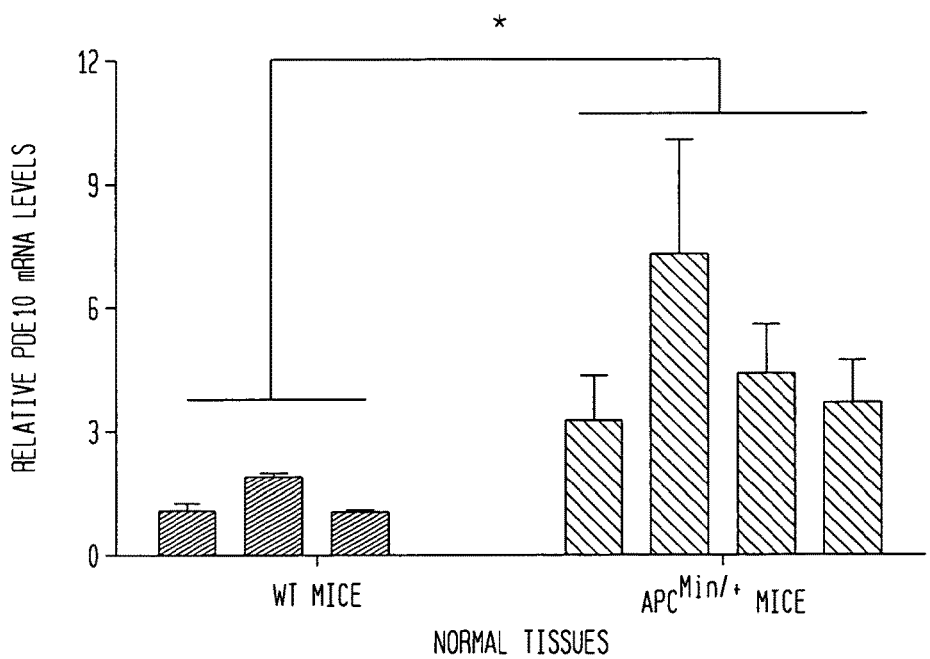
FIG. 7 is a graph showing PDE10A mRNA expression in normal appearing intestine from WT mice compared with mice harboring APC mutations (MIN), wherein PDE10A mRNA was measured by real-time PCR, and wherein * indicates p<0.05.

These observations provide support for the predictive ability of PDE10A mRNA in mice with APC mutations that develop spontaneous intestinal tumors and which represent a model of human colon cancer development. The data show that PDE10 mRNA levels are elevated in tumors from mice with APC mutations compared with normal intestine from mice without APC mutations (FIG. 5A-B). The levels of PDE5A were not significantly different. Elevation of PDE10A was also evident by comparing paired specimens from normal intestine with tumors from mice with APC mutations (FIG. 6). It was an unexpected finding that PDE10A mRNA levels were elevated in "normal" appearing intestine samples from mice with APC mutations compared with the same tissue from mice that do not harbor APC mutations (FIG. 7).

Collectively, these observations demonstrate the utility of methods that measure PDE10A mRNA or proteins levels to predict disease risk, onset, progression, and recurrence using biopsies from normal tissues or precancerous lesions from individuals at low to high risk of developing colorectal cancer. Such diagnostic testing may be especially useful for individuals who do not yet show symptoms of precancerous or cancerous disease, nor have abnormal histopathology as determined by standard analysis of tissue biopsies.

EXAMPLE 5

PDE10 Knockdown Selectively Suppresses Growth of Colon Tumor Cells

Figure 8A:
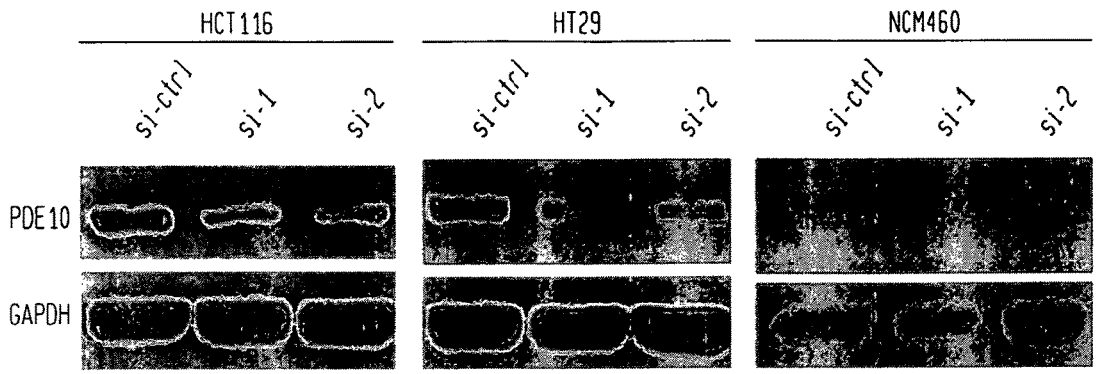
FIG. 8A is a Western blot and FIGS. 8B-C are graphs showing the effect of PDE10A siRNA knockdown on growth, apoptosis, and cell cycle progression of human colon tumor cell lines (HCT116 and HT29) and normal human colonocytes (NCM460), wherein PDE10A knockdown by PDE10A siRNA was confirmed in the two colon tumor cell lines, HT29 and HCT116, and the normal colonocyte cell line, NCM460 (A). PDE10A levels were measured by Western blotting after 72 hours of transfection. Effects of two different PDE10A siRNA (si-1 & si-2) are shown in comparison to the control scrambled siRNA (si-ctrl). Growth suppression by PDE10A siRNA was determined using the CellTiter Glo cell viability assay (B). Apoptosis induction by PDE10A siRNA was determined using the Caspase Glo apoptosis assay (C). Normal colonocytes were insensitive to the growth inhibitory and pro-apoptotic affects from siRNA knockdown of PDE10A, despite efficient knockdown of the protein. Effects of two different PDE10A siRNA (siPDE10-1 & siPDE10-2) are shown in comparison to control scrambled siRNA (siCtrl).
Figure 8B:
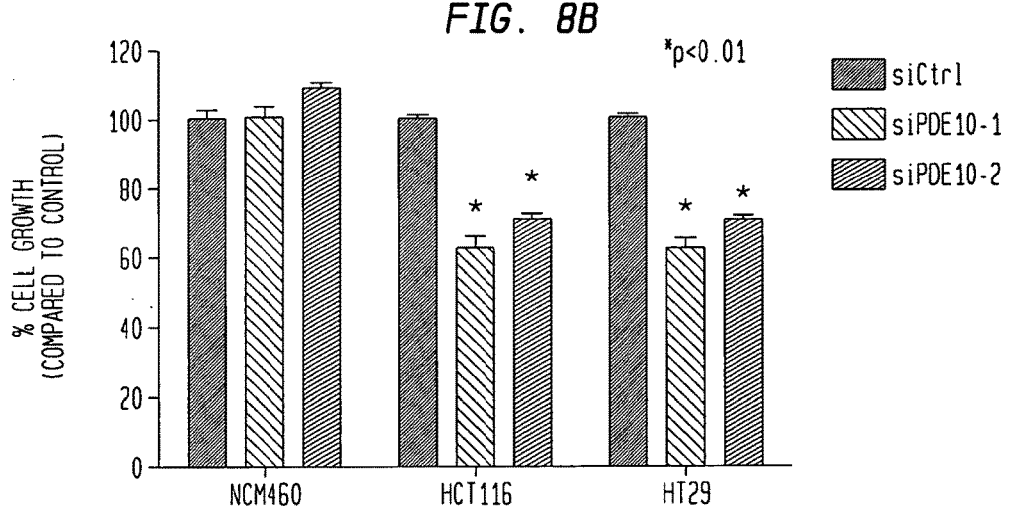
Figure 8C:
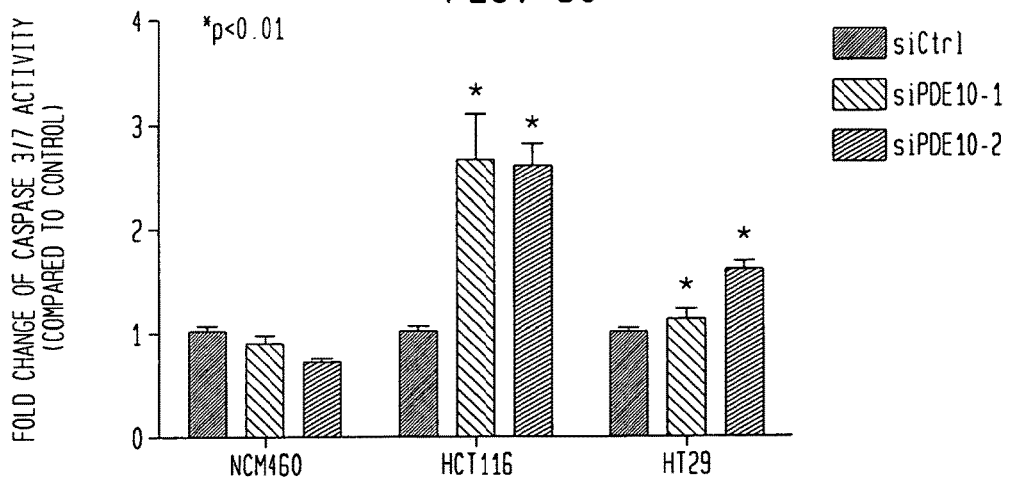

To determine the role of PDE10A as an anticancer target, a genetic approach involving siRNA technology was used to suppress PDE10A levels in normal human colonocytes (NCM460) and two human colon tumor cell lines (HCT116 and HT29). Two sequences of PDE10A siRNA, siPDE10-1 and siPDE10-2 (i.e., SEQ ID NOS:1 and 2), were used to exclude any off-target effects of the siRNA. Transfection with PDE10 siRNA reduced PDE10A protein levels (FIG. 8A) in all three cell lines within 72 hours as determined by Western blotting. The effects of SEQ ID NOS:1 and 2 are shown in comparison to the control scrambled siRNA (si-ctrl). As determined by CellTiter Glo cell viability assay (Promega), PDE10A siRNA caused significant growth suppression in the HCT116 and HT29 tumor cells, but the growth of normal colonocytes was unaffected by PDE10A knockdown (FIG. 8B). Similarly, as measured by the Caspase Glo apoptosis assay (Promega), PDE10A siRNA increased caspase activity in HCT116 and HT29 tumor cells, but did not affect caspase activity in normal colonocytes (FIG. 8C). These observations indicate an unexpected role of PDE10A in tumor cell growth and survival.

Figure 9A:
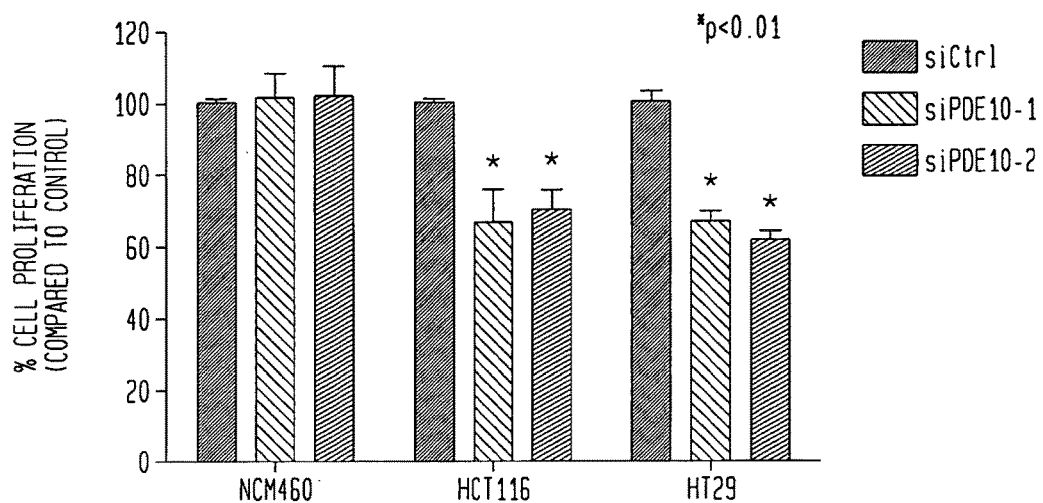
FIGS. 9A and 9B are graphs wherein 9A shows selective antiproliferative effects of PDE10A siRNA knockdown on colon tumor cells compared with normal colonocytes as measured by the EdU incorporation assay, and (B) shows cell cycle arrest by PDE10A siRNA in HT29 colon tumor cells. Cell cycle distribution was determined by flow cytometry using propidium iodide labeling. PDE10A knockdown selectively reduced the number of proliferating cells in tumor cell lines but not normal NCM460 colonocytes and caused G1 cell cycle arrest. Effects of two different PDE10A siRNA (siPDE10-1 & siPDE10-2) are shown in comparison to control scrambled siRNA (siCtrl).
Figure 9B:
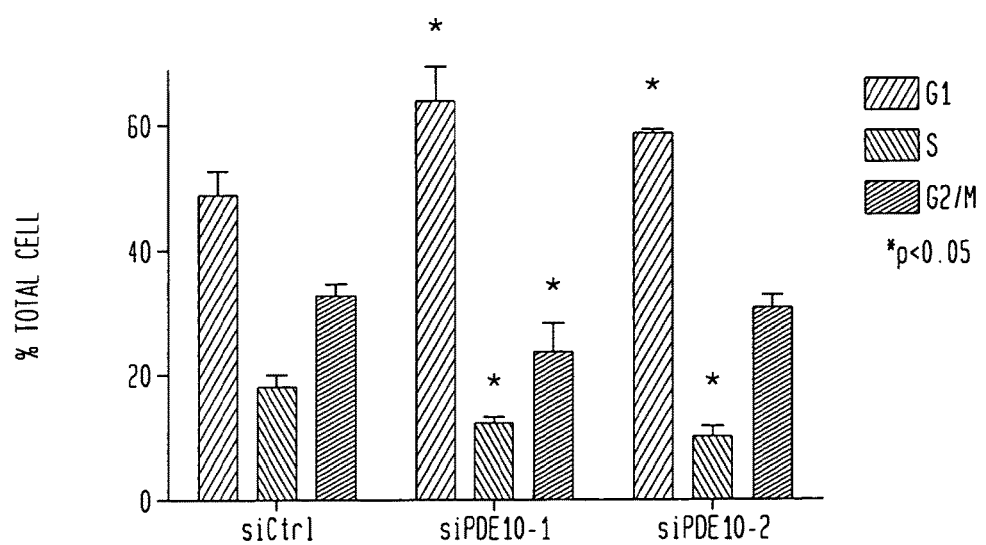

Moreover, a pronounced inhibition of proliferation in PDE10A knockdown cells by siRNA was observed in colon tumor cells, but not in normal colonocytes as measured by the Life Technologies Click-iT® EdU DNA synthesis assay (FIG. 9A). The inhibitory effect of PDE10A knockdown on cell cycle progression in human HT29 colon tumor cells transfected with PDE10 siRNA compared with scrambled control siRNA (using flow cytometry following PI labeling) is shown in FIG. 9B. Note that there was a significant increase in the percentage of cells in the G1 phase of the cell cycle and a corresponding decrease in cells in the S phase of the cell cycle in PDE10A knockdown HT29 cells compared with control cells, indicating that the suppression of PDE10A can cause cell cycle arrest in the G0-G1 phase of the cell cycle. Normal colonocytes were insensitive to the growth inhibitory, anti-proliferative, and pro-apoptotic effects that result from suppressing PDE10A levels, which is a desirable property for an anticancer drug that reflects potential for a wide therapeutic window with low toxicity and high efficacy.

EXAMPLE 6

Figure 10A:
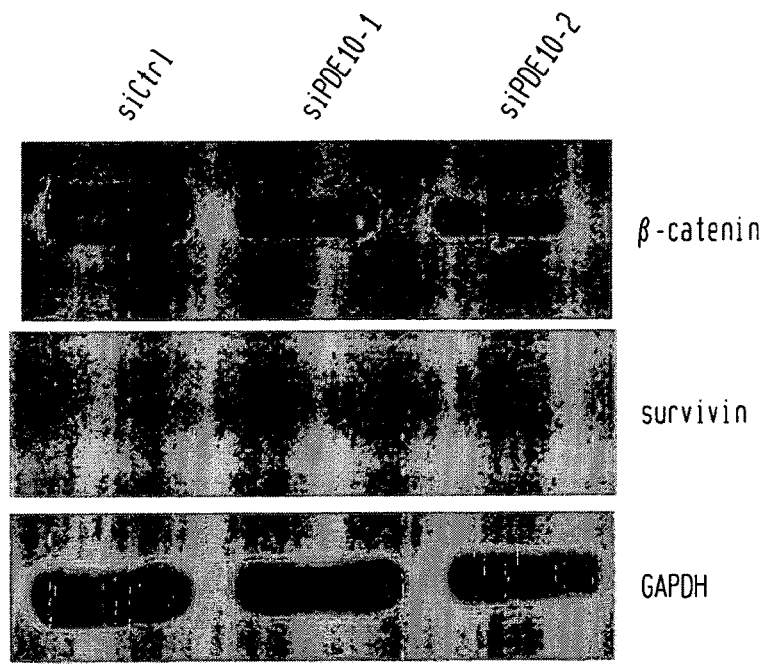
FIG. 10A is a Western blot and FIG. 10B is a graph wherein 10A shows suppression of β-catenin and survivin protein levels in human HCT116 colon tumor cells by PDE10A knockdown using siRNA, and (B) shows suppression of β-catenin-dependent TCF/LEF transcriptional activity in HCT116 and HT29 colon tumor cells by PDE10A siRNA knockdown. β-catenin and survivin are regulated by β-catenin-dependent TCF/LEF transcriptional activity and are known oncogenic proteins. The effects of two different PDE10A siRNA (siPDE10-1 & siPDE10-2) are shown in comparison to control scrambled siRNA (siCtrl).
Figure 10B:
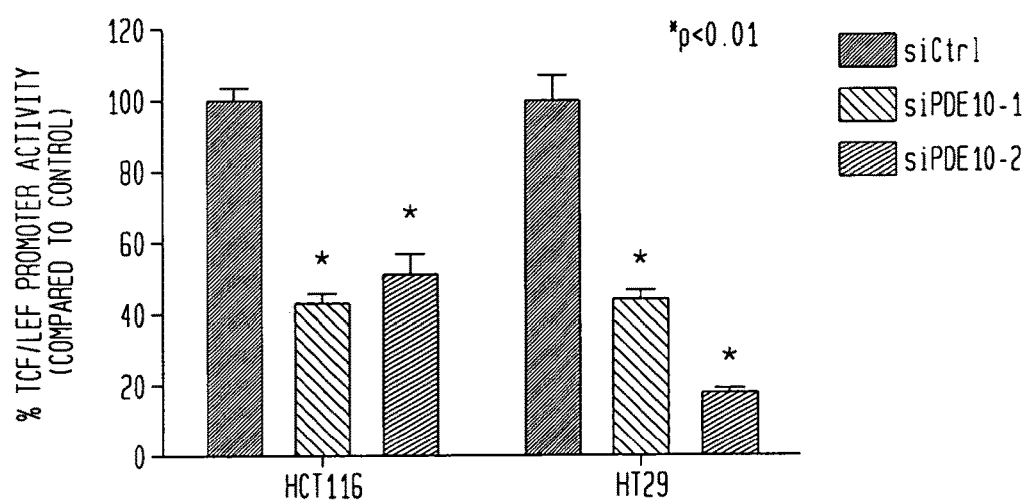

Tumor Cell Growth-inhibitory Activity of PDE10 Inhibition is Associated with Suppression of β-catenin/Tcf Mediated Transcriptional Activity To determine if PDE10A knockdown by siRNA can inhibit the Wnt/β-catenin signaling pathway, which is known to be an important oncogenic pathway involved in colorectal cancer progression and other cancers, the effect of PDE10A knockdown by siRNA on the level of β-catenin as well as β-catenin-dependent TCF/LEF transcriptional activity were measured. Levels of the tumor cell survival protein, survivin, which is known to be regulated by β-catenin-dependent TCF/LEF transcriptional activity, were also measured. PDE10A siRNA reduced levels of β-catenin and survivin in HCT116 colon tumor cells (FIG. 10A) which points to an unexpected activity of PDE10 suppression to inhibit an important oncogenic pathway. In addition, PDE10A siRNA suppressed TCF/LEF transcriptional activity as determined using a Topflash TCF luciferase reporter construct following transient transfection of HCT116 and HT29 colon tumor cells (FIG. 10B). These data are consistent with a mechanism of tumor cell growth inhibition and death by PDE10A knockdown involving the suppression of β-catenin-mediated transcription of genes that regulate tumor cell proliferation and survival.

EXAMPLE 7

PDE10A Inhibitors Selectively Inhibit Colon Tumor Cell Growth

Figure 11A:
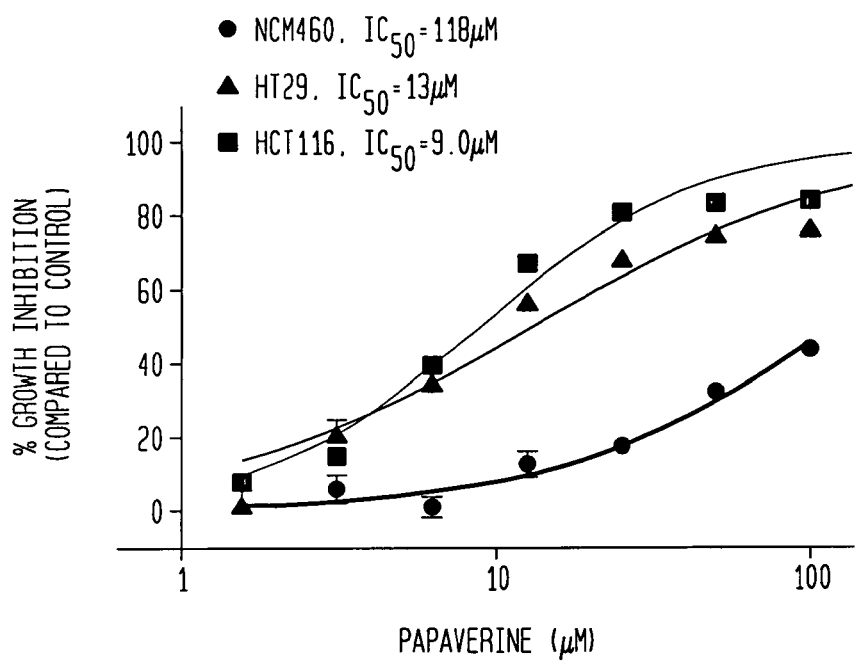
FIGS. 11A-D are graphs showing that the PDE10A inhibitor, papaverine, selectively inhibits the growth of human colon tumor cell lines, HCT116, SW480, and HT29, compared with normal colonocytes, NCM460 (A); papaverine inhibited HCT116 colon tumor cell growth and cGMP PDE activity in lysates from the same cell line within the same concentration range, indicating that it growth inhibitory activity involves PDE10A inhibition (B); and the PDE10A inhibitors, PQ-10 and Pf-2545920, potently and selectively inhibit colon tumor cell growth (C) and (D). Cell growth was measured by the Cell Titer Glo cell viability assay (Promega) following 72 hours of treatment, while cGMP PDE activity was measuring using the IMAP fluorescence polarization PDE assay (Molecular Devises).
Figure 11B:
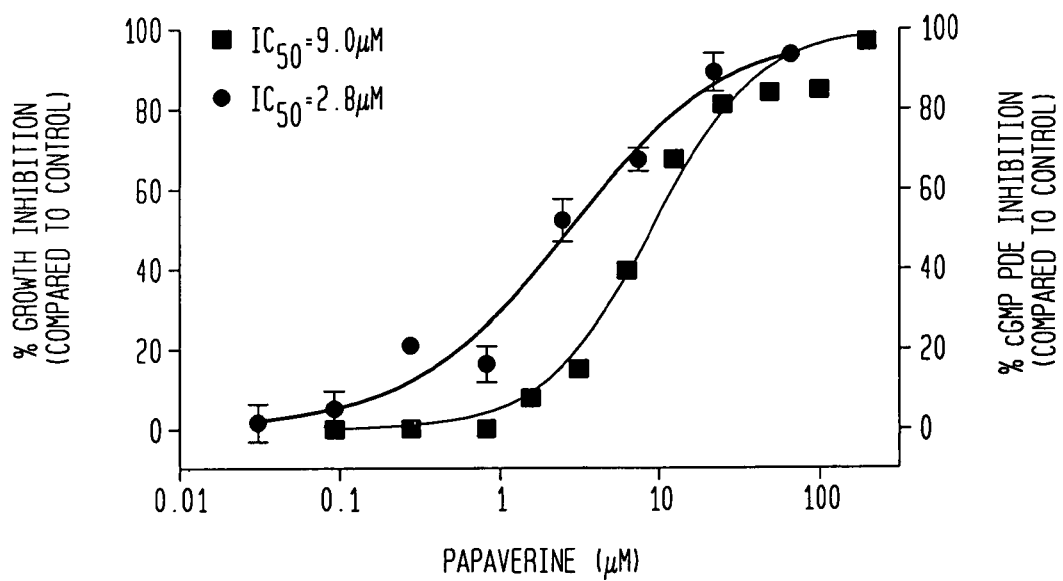
Figure 11C:
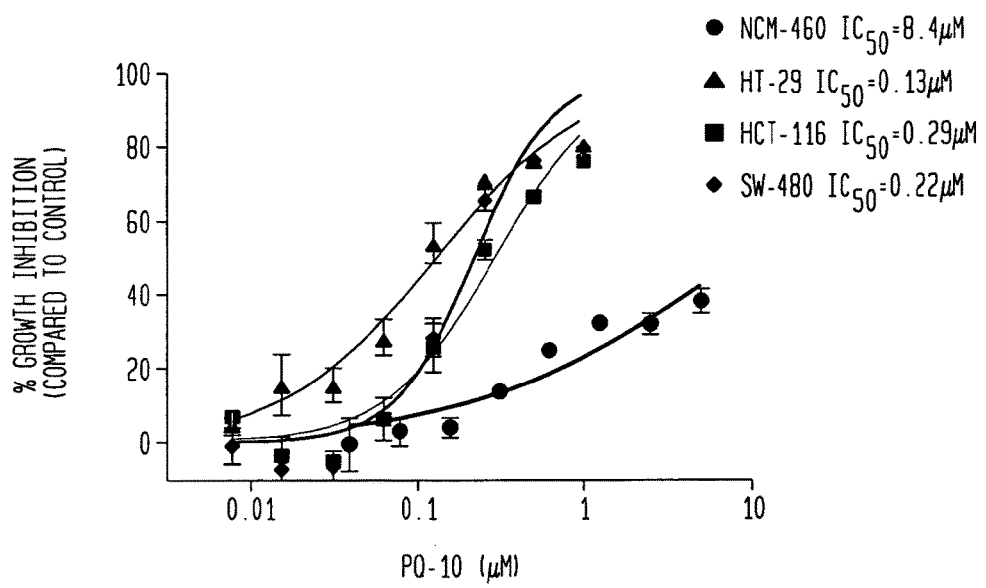
Figure 11D:
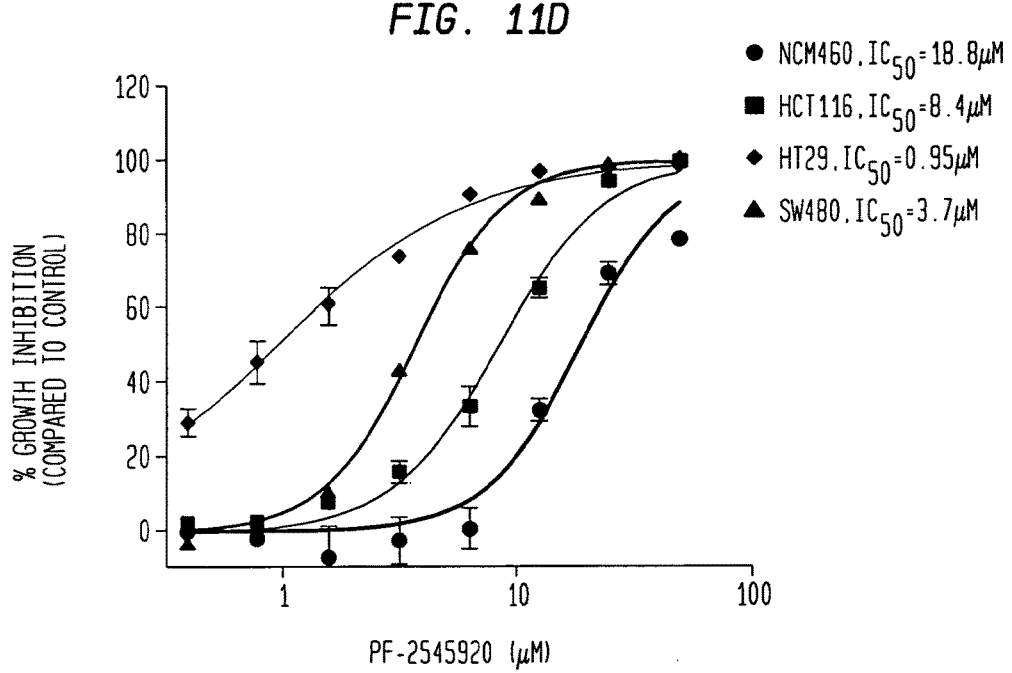

The anticancer activity of the PDE10A inhibitors, papaverine PQ-10, and PF-2545920 on the growth of cultured human colon tumor cells was determined using the Cell Titer Glo Cell Viability Assay (Promega) following 72 hours of treatment. As shown in FIG. 11A, papaverine inhibited the growth of human HCT116 and HT29 colon tumor cell lines with $IC_{50}$ values of 9 μM and 13 μM, respectively. By comparison, normal colonocytes (NCM460) were approximately 11-fold less sensitive with an $IC_{50}$ value of 118 μM. Levels of cGMP hydrolysis in lysates from HCT116 cells were confirmed to be inhibited by papaverine at concentrations that were comparable to those required for growth inhibition (FIG. 11B). Compared to papaverine, a nonselective PDE10 inhibitor, PQ-10, a more potent and specific PDE10 inhibitor, more potently inhibited the growth of human HCT116, SW-480 and HT29 colon tumor cell lines with $IC_{50}$ values of 0.29 μM, 0.22 μM and 0.13 μM, respectively (FIG. 11C). In addition, normal colonocytes (NCM460) were approximately 40 times less sensitive to treatment with PQ-10 in which an $IC_{50}$ value of 8.4 μM was calculated. Similarly, another potent and selective PDE10A inhibitor, PF-2545920, potently inhibited colon tumor cell growth and was appreciably less effective in normal colonocytes (FIG. 11D). These data show that PQ-10 and PF-2545920 are highly selective and potent inhibitors of human colon tumor cell growth, which is a property not shared by conventional chemotherapeutic drugs and many other anticancer agents.

EXAMPLE 8

PDE5A and PDE10A Inhibitors Suppress Colon Tumor Cell Growth

Effect of various PDE isozyme inhibitors on the growth of human colon tumor cells HCT116 and HT29 was determined using the Cell Titer Glo Cell Viability Assay (Promega) following 72 hours of treatment. The results are shown in the Table below.

| PDE Inhibitor | PDE Selectivity | Growth Inhibition (IC50/μM) | |
|---|---|---|---|
| | | HCT116 | HT29 |
| 8-MeoM-IBMX | PDE1 | Inactive | Inactive |
| EHNA | PDE2 | Inactive | Inactive |
| Cilostazol | PDE3 | Inactive | Inactive |
| Rolipram | PDE4 | Inactive | Inactive |
| MY5445 | PDE5 | 18 | 11 |
| Tadalafil | PDE5 | 38 | ND |
| Papaverine | PDE10 | 9 | 13 |

As shown in the Table, the PDE5A and 10A inhibitors suppressed human colon tumor cell growth, while other PDE isoenyme selective inhibitors were inactive. While specific inhibitors are not readily available for PDE6-9 and 11, their lack of uniform overexpression in cancer cells, rules out the involvement of other PDE isozymes in colon tumorigenesis.

The results with PDE5 inhibitors are consistent with those reported previously toinvolve a mechanism whereby PDE5 inhibition causes the elevation of cGMP and activation of protein kinase G to inhibit β-catenin/Tcf mediated transcriptional activity. See, Thompson et al., Cancer Res. 60(13): 3338-42 (2000); Tinsley, et al., Mol. Cancer Ther. 8(12): 3331-40 (2009); Tinsley, et al., Cancer Prev. Res. (Phila) 3(10):1303-13 (2010); Whitt, et al., Cancer Prev. Res. (Phila) 5(6):822-33 (2012); Tinsley, et al., Cancer Prev. Res. (Phila) 4(8):1275-84 (2011)). The colon tumor cell growth inhibitory activity of PDE10 inhibitors, however, has not been reported in the scientific or patent literature.

EXAMPLE 9

Combined inhibition of PDE5 and PDE10 Results in Synergistic Tumor Cell Growth Inhibitory Activity.

To determine if combined inhibition of PDE5A and PDE10A results in greater tumor cell growth inhibition compared with inhibiting either isozyme alone, the effects of the PDE5 inhibitor, MY5445, and the PDE10 inhibitor, papaverine (PAP) as single agents and in combination were determined.

Figure 12A:
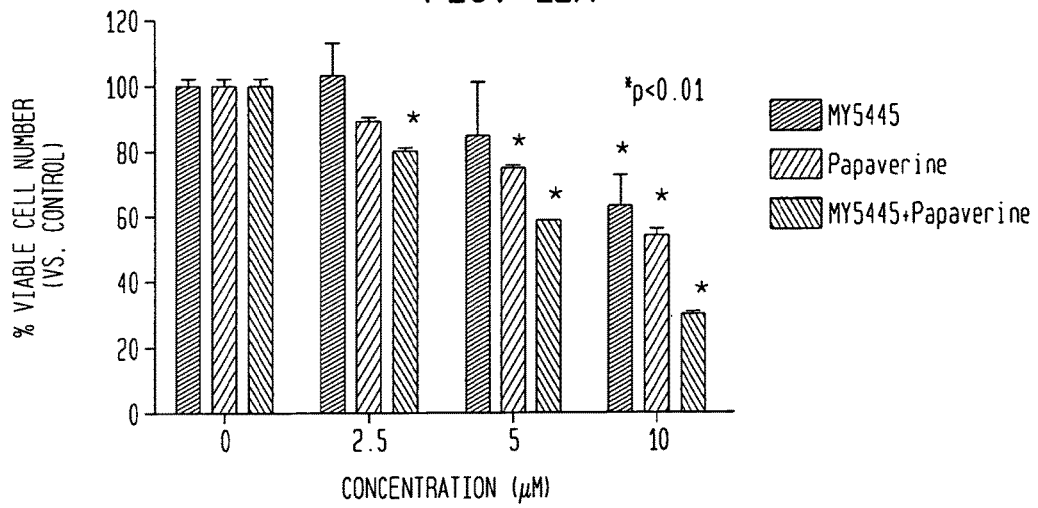
FIGS. 12A and C are graphs and FIG. 12B is a Western blot showing inhibition of colon tumor cell growth and suppression of β-catenin and survivin levels and TCF/LEF transcriptional activity in response to treatment with PDE5A and PDE10A inhibitors, MY5445 and papaverine, respectively.
Figure 12B:
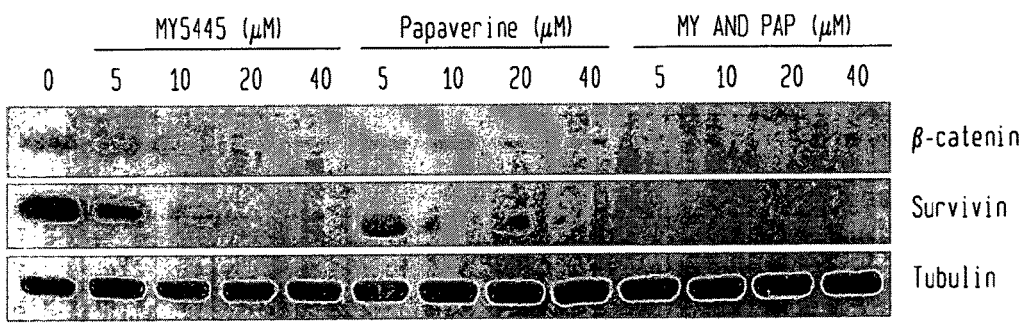
Figure 12C:
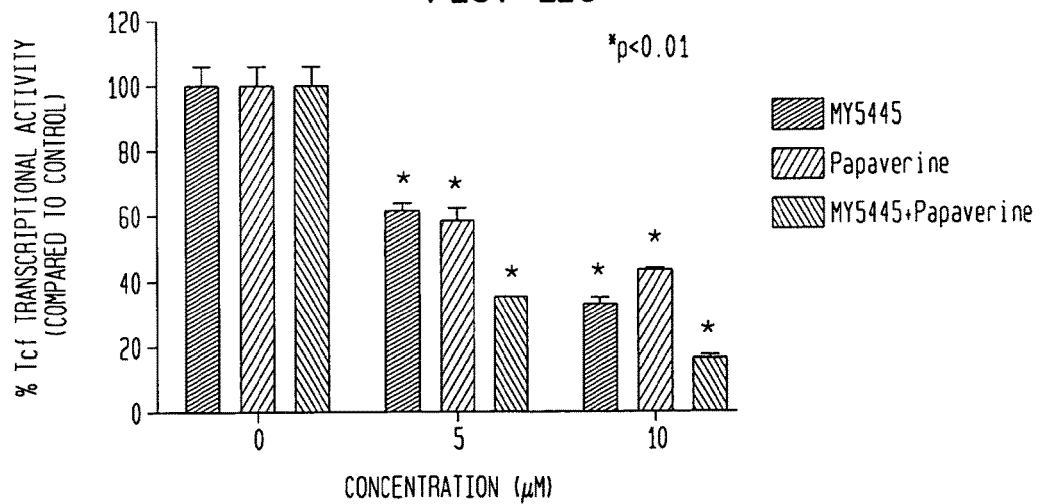

As shown in FIG. 12A, both MY5445 and papaverine suppressed HCT116 colon tumor cell growth alone, but when combined, resulted in greater growth inhibitory activity than either agent administered alone. The effects of MY5445 and papaverine on the levels of 13-catenin and survivin were also measured by Western blotting. Similar to their combined benefits for inhibiting colon tumor cell growth, MY5445 and papaverine also reduced β-catenin and survivin levels in HCT116 colon tumor cells greater when combined, compared with individual agents (FIG. 12B). Consistent with the suppression of β-catenin levels, combined treatment with MY5445 and papaverine resulted in greater suppression of TCF/LEF transcriptional activity compared with treatment with individual agents (FIG. 12C).

EXAMPLE 10

Effect of Chemically Distinct PDE10 Inhibitors on Growth of Human Colon Tumor Cells The inhibitory effect of various PDE10A inhibitors on human colon tumor cell growth was measured. The PDE10A inhibitors tested were: papaverine, PQ-10 ((R)-6,7-dimethoxy-4-{3-(quinoxalin-2-yloxy)pyrrolidin-1-yl}quinazoline), PF-2545920, (E)-2-{4-(1H-pyrazol-1-yl)phenyl}-N'-(4-bromo-3,5-dimethoxybenzylidene)-2-methoxyacetohydrazide (compound no. 4); 2-{(9-bromo-2-methyl-[1,2,4]triazolo[1,5-c]quinazolin-5-yl)thio}acetonitrile (compound no. 5); {2-(6hloropyridin-3-yl)-4-(2-methoxyethoxy)-7,8-dihydropyrido[4,3-d]pyrimidin-6 (5H)-yl)(1-neio-1H-imidazol-4-yl)}methanone (compound no. 6); and 8,9-dimethoxy-1-(pyridin-3-yl)-5,6-dihydroimidazo[5,1-a]isoquinoline (compound no. 7). With the exceptions of papaverine and PF-2545920 which were obtained commercially, the other PDE10A inhibitors were synthesized as follows:

The synthesis of PQ-10 was performed using the Mitsunobu reaction of (S)-3-hydroxy-1-Boc-pyrrolidine (1) with 2-quinoxalinol (2) to give intermediate 3, which underwent Boc-deprotection with trifluoroacetic acid (TFA) followed by coupling with 4-chloro-6,7-dimethoxyquinazoline (4) to afford PQ-10 (Scheme 1). See, Chappie, et al., *J. Med. Chem.* 50:182-185 (2007).

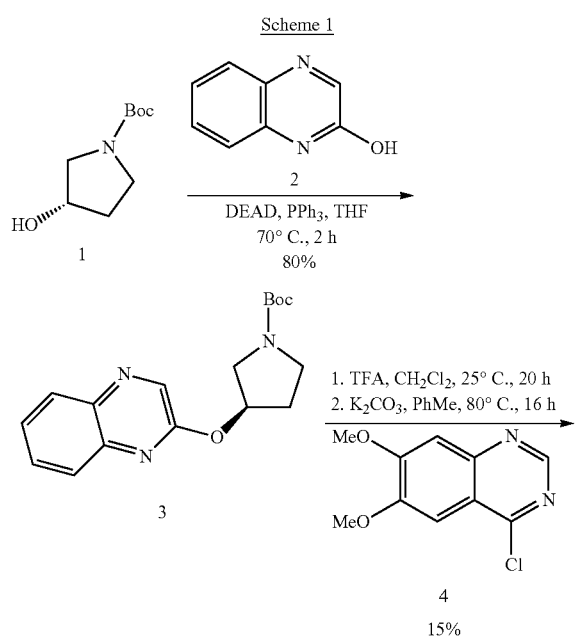

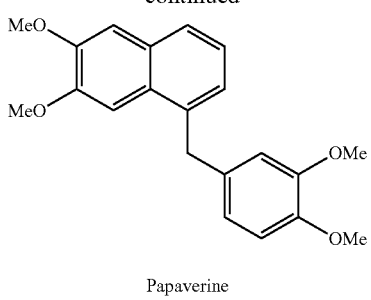

Papaverine

The synthesis of (E)-2-{4-(1H-pyrazol-1-yl)phenyl}-N'-(4-bromo-3,5-dimethoxybenzylidene)-2-methoxyacetohydrazide (compound no. 4) is outlined in Scheme 2. See, Cutshall, et al., *Bioorg. Med. Chem. Lett.* 22:5595-5599 (2012). 4-(1H-Pyrazolyl)benzaldehyde (5) was subjected to bromoform and potassium hydroxide in methanol/dioxane to give a methoxy phenylacetic acid derivative 6. Esterification of carboxylate 6 afforded the methyl ester 7. Treatment of the methyl ester 7 with hydrazine provided coupling partner acyl hydrazide 8, which was reacted with 4-bromo-3,5-dimethoxybenzaldehyde (9) to deliver the compound.

PF-2545920 and papaverine were obtained from commercial suppliers.

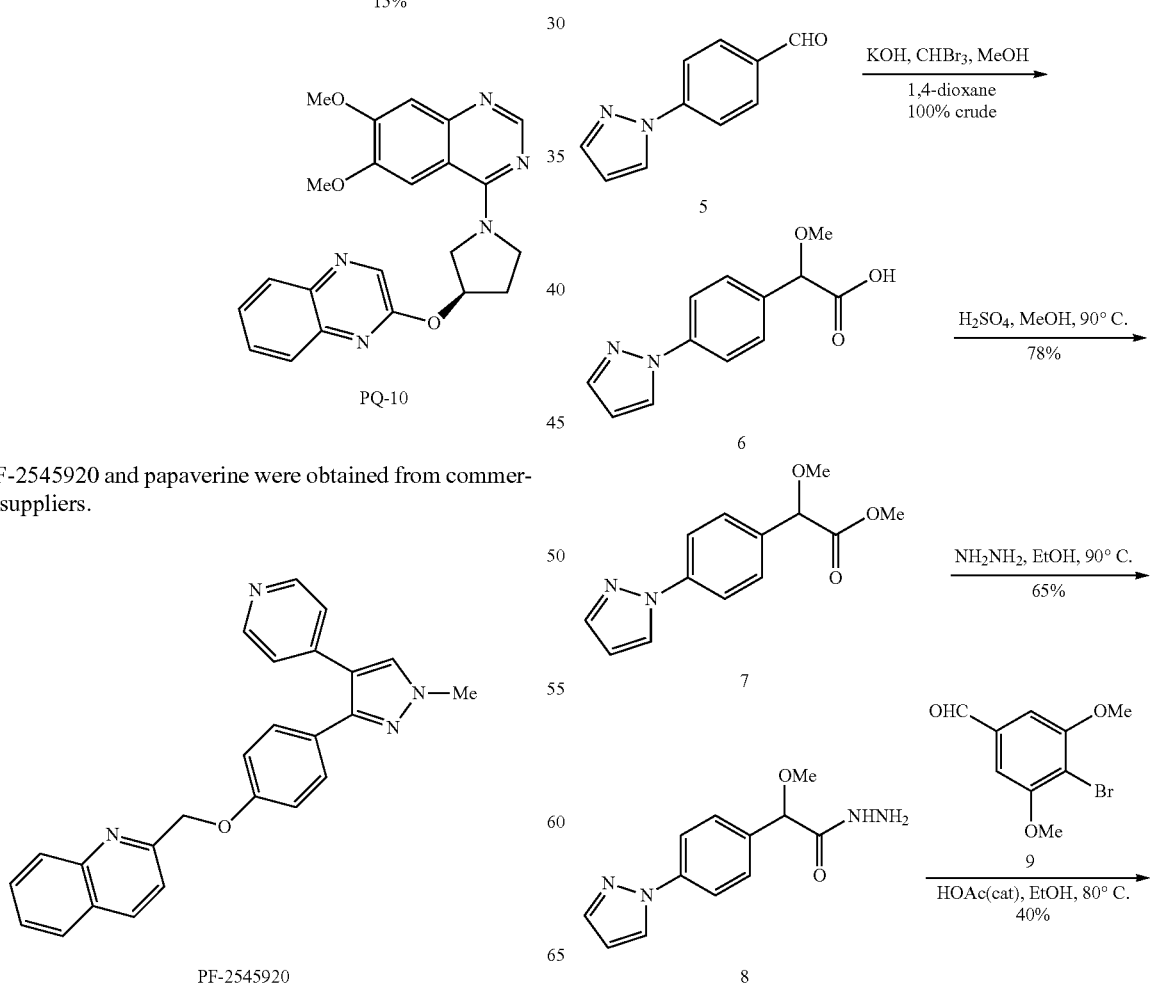

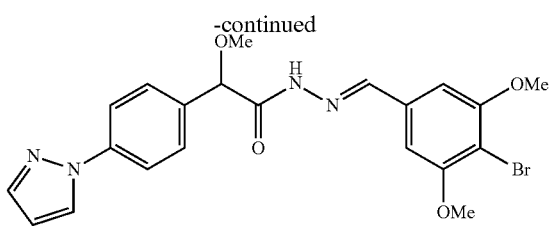

The synthesis of 2-{(9-bromo-2-methyl-[1,2,4]triazolo[1,5-c]quinazolin-5-yl)thio}acetonitrile (compound no. 5), outlined in scheme 3, began with the treatment of 2-amino-5-bromobenzonitrile (9) with thiophosgene in methylene chloride to give isothiocyanate 10, which upon addition of acethydrazide in refluxing ethanol afforded 6H-[1,2,4]triazolo-[1,5-c]quinazoline-5-thione 11 (Scheme 3). See, Kehler, et al., Bioorg. Med. Chem. Lett. 21:3738-3742 (2011). The sulfur group of 11 was selectively alkylated with bromoacetonitrile to deliver the compound.

Scheme 3:

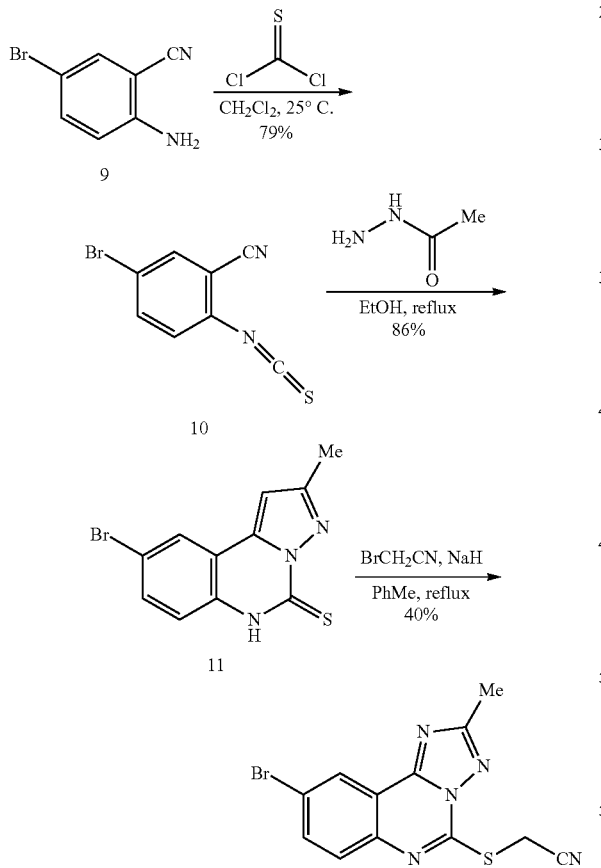

Synthesis of {2-(6-chloropyridin-3-yl)-4-(2-methoxyethoxy)-7,8-dihydropyrido[4,3-d]pyrimidin-6(5H)-yl)(1-neio-1H-imidazol-4-yl)}methanone (compound no. 6) is shown in scheme 4. 1-Tert-butyl-3-ethyl-4-oxopiperidine-1,3-dicarboxylate (12) underwent a facile three-component condensation with 6-chloropyridine-3-carboximidamide hydrochloride (13) and 2-bromoethyl methyl ether followed by Boc- deprotection to afford advanced an intermediate 14, which was coupled with 1-methyl-1H-imidazole-4-carboxylic acid (15) (Scheme 4). See, Raheem, et al., Bioorg. Med. Chem. Lett. 22:5903-5908 (2012).

Scheme 4:

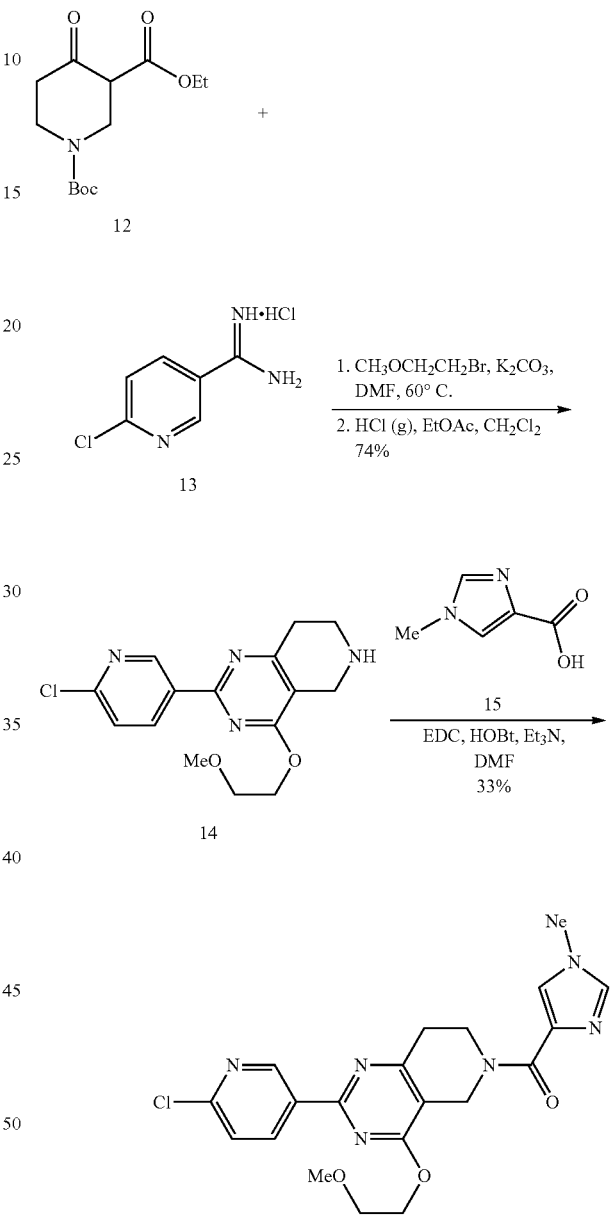

Synthesis of 8,9-dimethoxy-1-(pyridin-3-yl)-5,6-dihydroimidazo[5,1-a]isoquinoline (compound no. 7) is shown in scheme 5. 3,4-Dimethoxyphenethylamine (16) was transformed to formamide 17 in the presence of ethyl formate, then to isonitrile 18 with phosphorus oxychloride (Scheme 5). See, Ho, et al., Bioorg. Med. Chem. Lett. 22:2585-2589 (2012). An Ugi coupling with 3-pyridinecarboxaldehyde in the presence of ammonium formate provided precursor 19, which was subjected to Bischler-Napieralski cyclization to provide 8,9-dimethoxy-1-(pyridin-3-yl)-5,6-dihydroimidazo[5,1-a]isoquinoline.

Scheme 5:

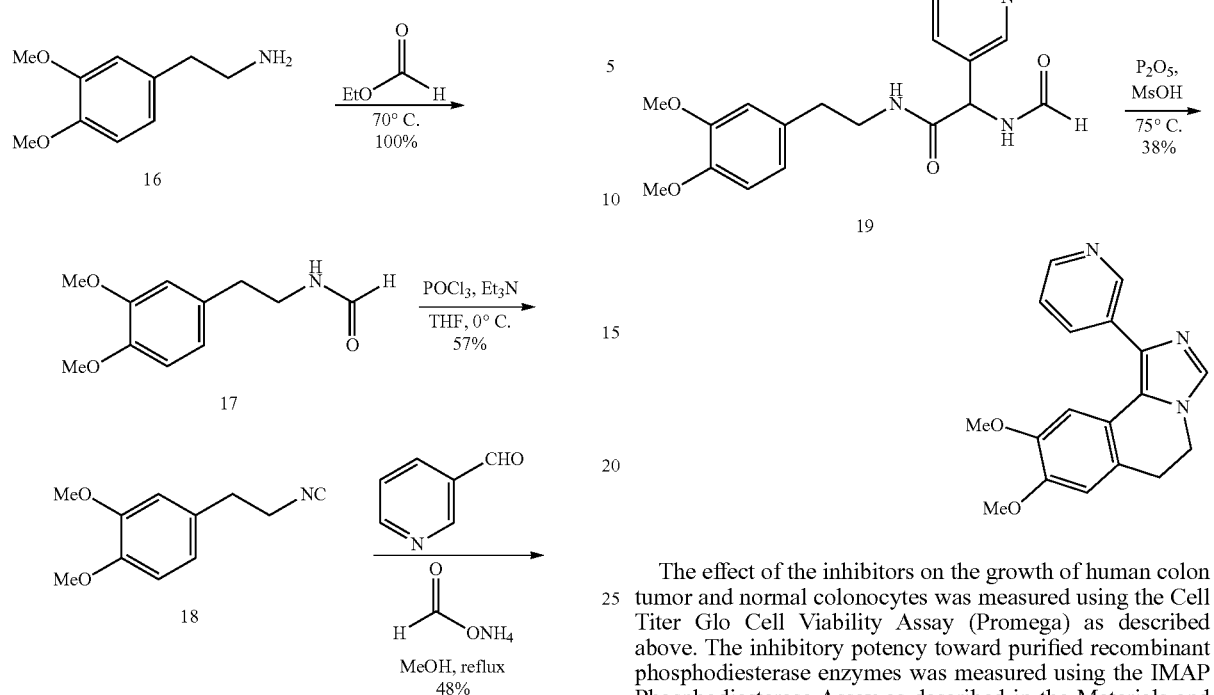

The effect of the inhibitors on the growth of human colon tumor and normal colonocytes was measured using the Cell Titer Glo Cell Viability Assay (Promega) as described above. The inhibitory potency toward purified recombinant phosphodiesterase enzymes was measured using the IMAP Phosphodiesterase Assay as described in the Materials and Methods section. The results are shown in the Table below.

| PDE10 Inhibitors | | | | | |
|---|---|---|---|---|---|
| | | Phosphodiesterase Inhibition | | Growth Inhibition | |
| Compound | Structure | Isozyme | cGMP $IC_{50}$ | cAMP $IC_{50}$ | Cell Line | $IC_{50}$ |
| Papaverine | | PDE10A | 22 nM | 0.101 μM | HT-29 | 24.5 μM |
| | | | | | HCT-116 | 6.7 μM |
| | | | | | SW-480 | 11.2 μM |
| | | | | | NCM-460 | >100 μM |
| PQ-10 | | PDE1A | 8.8 μM | 29.2 μM | HT-29 | 0.197 μM |
| | | PDE2A | 3.7 μM | 7 μM | HCT-116 | 0.201 μM |
| | | PDE3A | 211 nM | 470 nM | SW-480 | 0.199 μM |
| | | PDE3B | 273 nM | N/A | NCM-460 | >5 μM |
| | | PDE4B | N/A | 17.8 μM | | |
| | | PDE5A | 1.8 μM | N/A | | |
| | | PDE9A | >200 μM | N/A | | |
| | | PDE10A | 3.88 nM | 5.38 nM | | |
| | | PDE11A | 13.2 μM | 30.1 μM | | |

-continued

| | | PDE10 Inhibitors | | | | |
|---|---|---|---|---|---|---|
| | | | Phosphodiesterase Inhibition | | Growth Inhibition | |
| Compound | Structure | Isozyme | cGMP $IC_{50}$ | cAMP $IC_{50}$ | Cell Line | $IC_{50}$ |
| PF-2545920 | 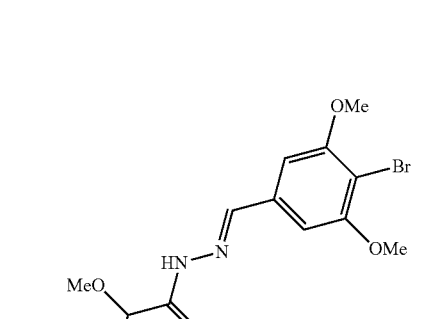 | PDE10A<br>PDE5<br>*all others reported @ >1000X selectivity | 0.496 nM<br>>50 μM | 0.329 nM<br>N/A | HCT-116<br>NCM-460<br>HT29<br>SE480 | 8.4 μM<br>18.8 μM<br>0.95 uM<br>3.7 uM |
| Compound no. 4 | 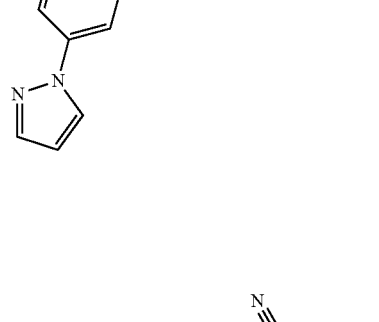 | PDE10A<br>Reported >300x selective | 1.47 nM | 2.02 nM | HCT-116 | 3.128 μM |
| Compound no. 5 | 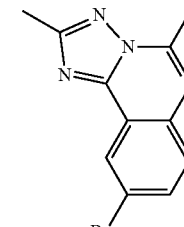 | PDE10A<br>PDE4d6<br>PDE5A | 8.90 nM<br>2200 nM<br>(reported)<br>5700 nM<br>(reported) | 8.66 nM | HCT-116 | 9.93 μM |

-continued

| | | PDE10 Inhibitors | | | | |
|---|---|---|---|---|---|---|
| | | | Phosphodiesterase Inhibition | | Growth Inhibition | |
| Compound | Structure | Isozyme | cGMP $IC_{50}$ | cAMP $IC_{50}$ | Cell Line | $IC_{50}$ |
| Compound no. 6 | | PDE10A | 3.44 nM | 11.43 nM | HCT-116 | >50 μM |
| Compound no. 7 | | PDE10A<br>PDE3A<br>PDE7A1<br>Others | 29 nM (reported)<br>449 nM (reported)<br>45% @ 3 μM (reported)<br>>4 μM (reported) | | HT-29<br>HCT-116<br>SW-480 | >50 μM<br>>50 μM<br>>50 μM |

The data show that several highly potent PDE10A inhibitors with various degrees of PDE10A isozyme specificity can effectively inhibit colon tumor cell growth.

Example 11

Inhibitory Effect of PF-245920 on the Growth of a NCI-60 Cancer Cell Line Panel

Figure 13:
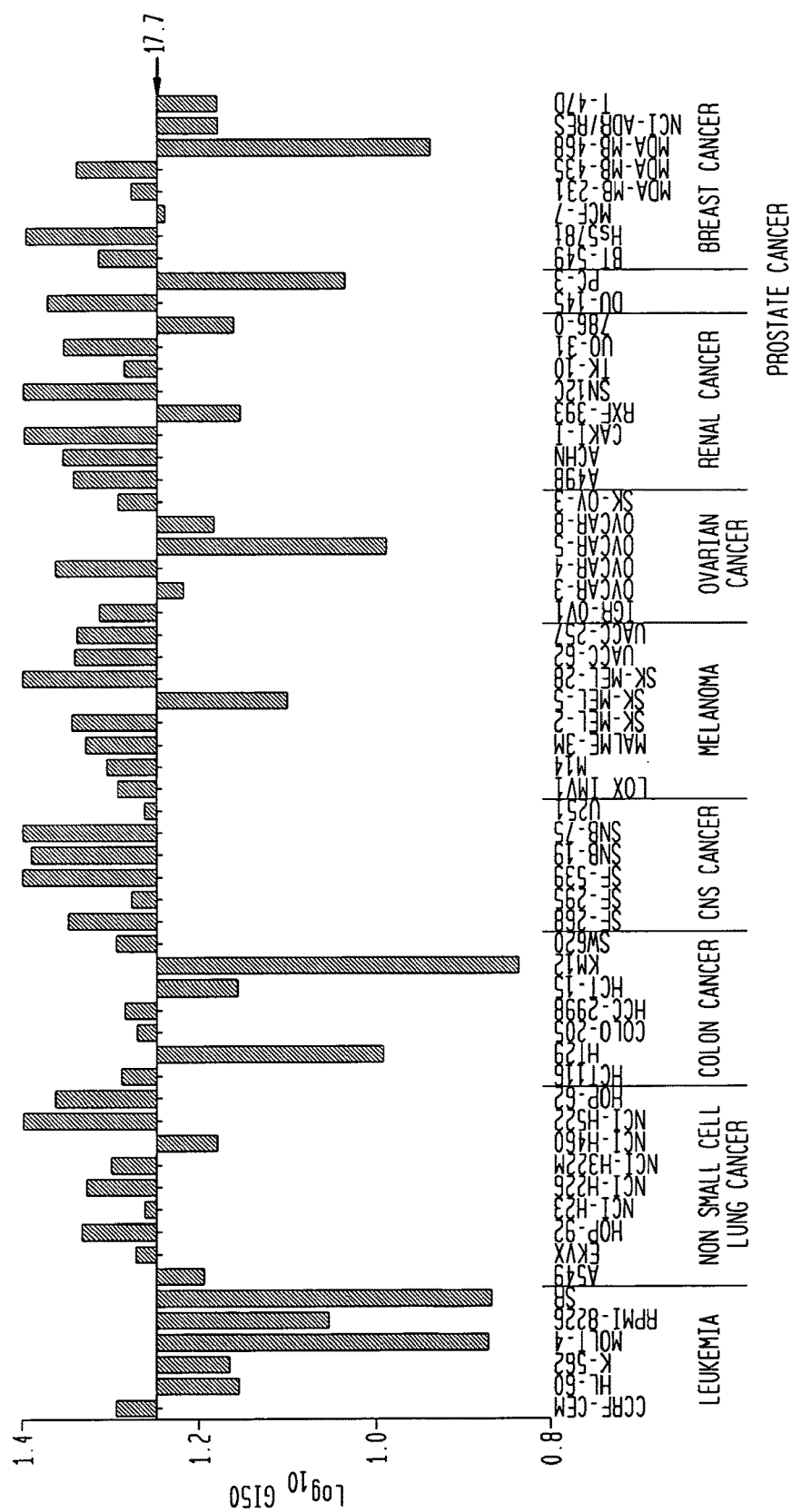
FIG. 13 is a graph showing broad spectrum tumor cell growth inhibitory activity of the PDE10A inhibitor, PF-2545920, against multiple human tumor cell lines in the "NCI60 cancer cell line panel". Tumor growth inhibitory activity was measured using a cell viability assay following 72 hours of treatment. Potency values ($GI_{50}$) as measured in each tumor cell line are shown on the y axis. The average $GI_{50}$ value was calculated to be 17.7 μM.

The Promega Cell TiterGlo Cell Viability Assay as described above was used to determine the spectrum anticancer activity of the selective PDE10A inhibitor, PF-2545920 using a panel of histologically diverse human tumor cell lines. As shown in FIG. 13, PF-2545920 exhibited a broad range of tumor cell growth inhibitory activity in the NCI-60 cancer cell line panel, which includes cell lines derived from leukemia, lung, colon, melanoma, ovarian, renal, prostate, breast and CNS tumors. Tumor cell lines derived from hematological malignancies tended to be the most sensitive to treatment with PF-2545920, but all other tumor cell lines derived from solid tumors were also sensitive.

EXAMPLE 12

Figure 14:
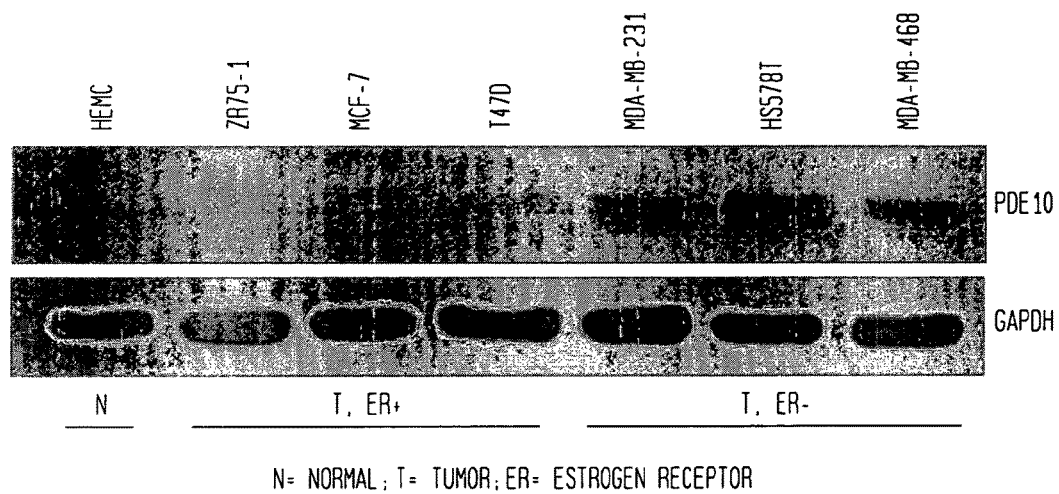
FIG. 14 is a Western blot showing PDE10A expression in a panel of human breast tumor cell lines compared with normal human mammary epithelial cells (HMEC). The MCF7, T47D, ZR75 breast tumor cell lines are classified as estrogen receptor positive, while the MDA-MB-231, HS578T, and MDA-MB-468 lines are classified as estrogen receptor-negative. PDE10A levels were elevated in all six beast tumor cell lines compared with normal mammary epithelial cell, but those breast tumor cell lines with the estrogen receptor phenotype showed appreciably higher levels. PDE10A levels were detected by Western blotting using a PDE10A specific antibody. Levels of GAPDH were used as a loading control.
Figure 15:
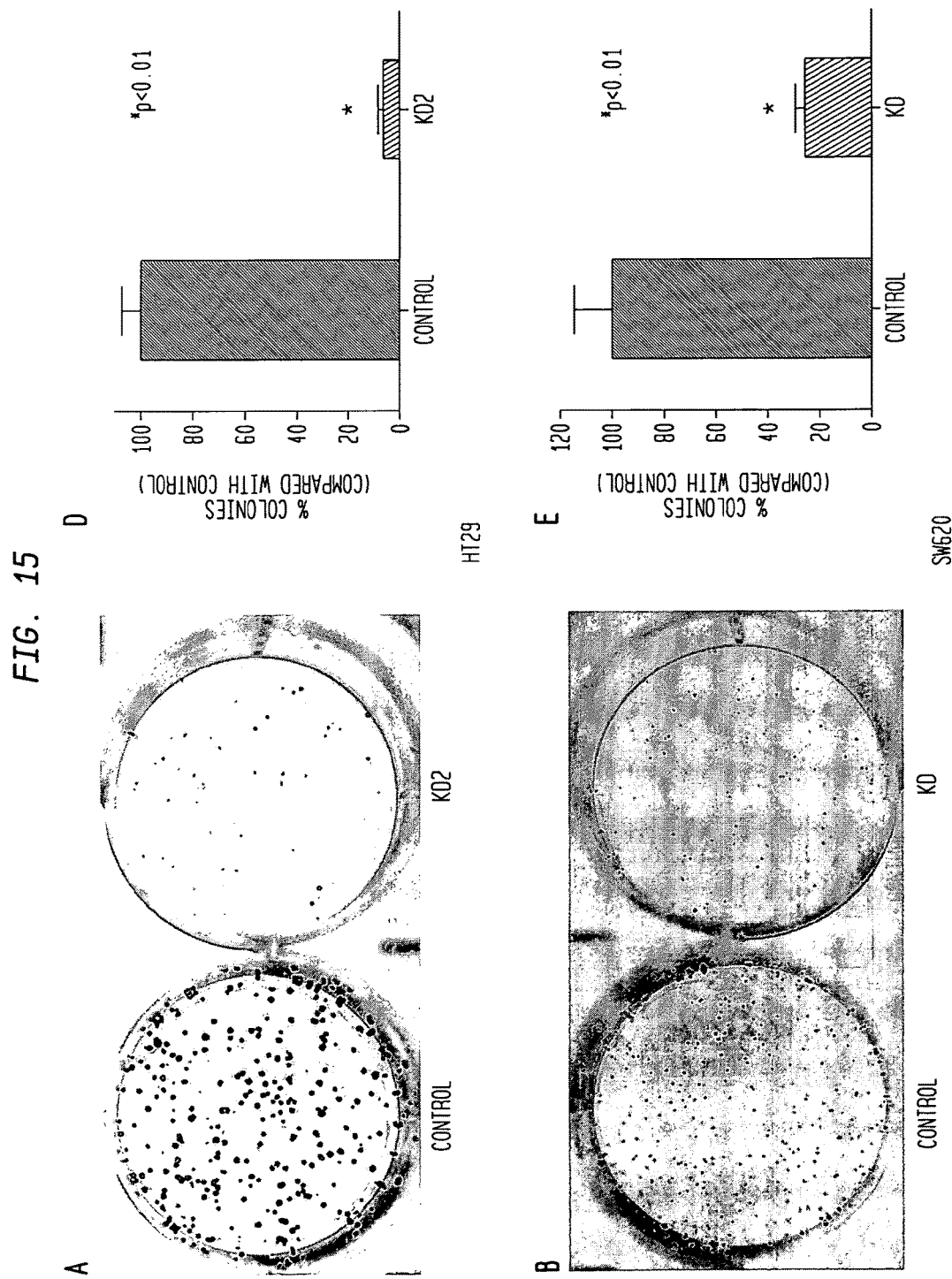
FIGS. 15A-C are photographs and D-F are graphs that show stable knockdown of PDE10A by shRNA can suppress colony formation of colon tumor cell. The effect of PDE10 knockdown on anchorage-dependent colony formation in HT29 cells (A and D) and SW620 colon tumor cells (B and E). Stable PDE10 knockdown or control cells were grown in liquid culture for 14 days followed by stained with crystal violet. Representative images are shown on the left panels (A and B), and statistical analysis is shown on the right panels (D and E). Figs C and F show that PDE10 knockdown leads to a decrease of anchorage-independent colony formation in HT29 cells. Cells were grown in soft agar for 21 days then stained and counted. Images from a representative experiment are shown.

Human Breast Tumor Cells Overexpress PDE10A Compared with Normal Mammary Epithelial Cells Western blotting of whole cell lysates from normal mammary epithelial cells (HMEC) and six breast tumor cell lines showed that PDE10A levels were generally elevated in tumor cells compared with normal mammary epithelial cells (FIG. 14A). Unexpectedly, breast tumor cell lines that display the estrogen receptor negative phenotype (MDA-MB-231, HS578T, and MDA-M-468) expressed appreciably higher levels of PDE10A compared with breast tumor cell lines that express estrogen receptors (MCF7, T47D, ZR75). Patients with estrogen receptor negative disease have no or few estrogen receptors on their breast cancer cells and cannot be treated with hormonal therapy. Estrogen receptor negative disease also tends to be more aggressive compared with estrogen receptor positive disease. The involvement of PDE10 in tumorigenesis is evident by PDE10 knockdown colon tumor cell lines showing significantly reduced ability to form colonies compared with vector control cells, regardless of whether the cells were grown in liquid culture or soft agar (FIG. 15).

All patent publications and non-patent publications are indicative of the level of knowledge of those skilled in the art to which this invention pertains. All such publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of treating colorectal cancer, a colorectal adenoma or a colorectal polyp comprising administering to a subject diagnosed with colorectal cancer, a colorectal adenoma or a colorectal polyp a therapeutically effective amount of the PDE10A inhibitor 2-[4-(1-methyl-4-pyridin-4-yl-1H-pyrazol-3-yl)-phenoxym]-quinoline, or a pharmaceutically acceptable salt thereof.

2. The method of claim 1, wherein the colorectal cancer is colon cancer.

3. The method of claim 2, wherein the PDE10A inhibitor is co-administered with a PDE5 inhibitor.

4. The method of claim 1, wherein the subject is a human.

5. The method of claim 1, wherein the subject who has colorectal cancer, a colorectal adenoma or a colorectal polyp has familial or sporadic adenomatous polyposis, HNPCC, or inflammatory bowel disease.

6. The method of claim 1, wherein the subject has a mutated APC gene.

7. The method of claim 1, further comprising administering to the subject a therapeutically effective amount of another active agent.

8. The method of claim 7, wherein the active agent is a PDE5 inhibitor.

* * * * *

UNITED STATES PATENT AND TRADEMARK OFFICE
CERTIFICATE OF CORRECTION

| | |
|---|---|
| PATENT NO. | : 10,039,764 B2 |
| APPLICATION NO. | : 14/904632 |
| DATED | : August 7, 2018 |
| INVENTOR(S) | : Gary A. Piazza |

It is certified that error appears in the above-identified patent and that said Letters Patent is hereby corrected as shown below:

In the Specification

In Column 1, Line 19, after the "STATEMENT REGARDING FEDERALLY SPONSORED RESEARCH OR DEVELOPMENT" and directly above "BACKGROUND OF THE INVENTION," delete:
"The invention was made with support under NCI Grant Nos. CA 155638 and 1R01CA148817. Therefore, the Government has certain rights in the invention."

Replace with the following statement:
--This invention was made with government support under R01 CA148817, and R01 CA155638 awarded by the National Institutes of Health. The government has certain rights in the invention.--

Signed and Sealed this
Twenty-third Day of April, 2024

Katherine Kelly Vidal
*Director of the United States Patent and Trademark Office*